(12) United States Patent
Miller et al.

(10) Patent No.: US 11,389,112 B1
(45) Date of Patent: Jul. 19, 2022

(54) PHYSICAL STRUCTURE OF WEARABLE DEVICE

(71) Applicant: Tula Health, Inc., Kaysville, UT (US)

(72) Inventors: David R. Miller, Morgan, UT (US); Jeffrey Lee, Morgan, UT (US); Federico Calero, Plymouth, MI (US); Trevor Calero, Plymouth, MI (US); Devin W. Miller, Morgan, UT (US)

(*) Notice: Subject to any disclaimer, the term of this patent is extended or adjusted under 35 U.S.C. 154(b) by 89 days.

(21) Appl. No.: 16/543,355

(22) Filed: Aug. 16, 2019

Related U.S. Application Data

(63) Continuation of application No. 14/985,245, filed on Dec. 30, 2015, now Pat. No. 10,485,475.

(60) Provisional application No. 62/192,935, filed on Jul. 15, 2015, provisional application No. 62/117,282, filed on Feb. 17, 2015.

(51) Int. Cl.
*A61B 5/145* (2006.01)
*A61B 5/00* (2006.01)
*A61B 5/0537* (2021.01)
*A61B 5/1455* (2006.01)

(52) U.S. Cl.
CPC .......... *A61B 5/4875* (2013.01); *A61B 5/0059* (2013.01); *A61B 5/0537* (2013.01); *A61B 5/1455* (2013.01); *A61B 5/681* (2013.01); *A61B 5/6801* (2013.01); *A61B 5/6843* (2013.01); *A61B 5/6844* (2013.01); *A61B 5/742* (2013.01); *A61B 2562/00* (2013.01); *A61B 2562/0261* (2013.01)

(58) Field of Classification Search
CPC ... A61B 5/145; A61B 5/14546; A61B 5/1455; A61B 5/14552; A61B 5/7221
See application file for complete search history.

(56) References Cited

U.S. PATENT DOCUMENTS

| 3,785,142 A | 1/1974 | Soguel |
| 8,174,482 B1 | 5/2012 | Yeung |
| 2002/0007126 A1 | 1/2002 | Nissila |
| (Continued) | | |

FOREIGN PATENT DOCUMENTS

EP    2124731 B1 *  6/2012  ......... G08B 21/0453

OTHER PUBLICATIONS

Espacenet Translation of EP 2124731 retrieved on Jun. 29, 2021 (Year: 2012).*

(Continued)

*Primary Examiner* — Eric F Winakur
(74) *Attorney, Agent, or Firm* — Miller IP Law LLC

(57) ABSTRACT

An electronic device is described herein that may include various components, including a band, a physiological sensor, a feedback sensor, a processor, a display, or a power source. The band may be shaped to fit around at least a portion of a body part of a user. The physiological sensor may include two separated by a fixed distance such that at least a portion of a signal transmitted by a first sensor is transmitted through a muscular-walled tube of the body part before being received by a second sensor. The processor may be operable to determine a physiological condition based on the signal received by the second physiological sensor. The physiological sensor may be embedded in the band. The band may be comprised of a flexible material. The feedback sensor may measure a pressure at which the band is held against the body part.

20 Claims, 34 Drawing Sheets

(56) References Cited

U.S. PATENT DOCUMENTS

| | | |
|---|---|---|
| 2004/0015058 A1 | 1/2004 | Besson |
| 2008/0033315 A1 | 2/2008 | Kim |
| 2012/0253153 A1* | 10/2012 | Trumble ............ A61B 5/14551 |
| | | 600/324 |
| 2012/0271121 A1 | 10/2012 | Della Torre |
| 2013/0027205 A1* | 1/2013 | Hansen ................ A61B 5/0205 |
| | | 340/573.1 |
| 2013/0119255 A1 | 5/2013 | Dickinson |
| 2013/0310700 A1* | 11/2013 | Wiard .................... A61B 5/742 |
| | | 600/485 |
| 2013/0317333 A1 | 11/2013 | Yang |
| 2014/0135602 A1* | 5/2014 | Lemke ................ A61B 5/0205 |
| | | 600/324 |
| 2014/0296720 A1* | 10/2014 | Lamego ............... A61B 5/6826 |
| | | 600/479 |
| 2014/0316305 A1 | 10/2014 | Venkatraman |
| 2014/0336493 A1 | 11/2014 | Kulach |
| 2014/0361147 A1 | 12/2014 | Fei |
| 2015/0157219 A1* | 6/2015 | Lee .................... A61B 5/02055 |
| | | 600/393 |
| 2016/0192716 A1 | 7/2016 | Lee |

OTHER PUBLICATIONS

Maattala et al., "Optimum Place for Measuring Pulse Oximeter Signal in Wireless Sensor-Belt or Wrist-Band", IEEE ICCIT, 2007, pp. 1856-1861.

\* cited by examiner

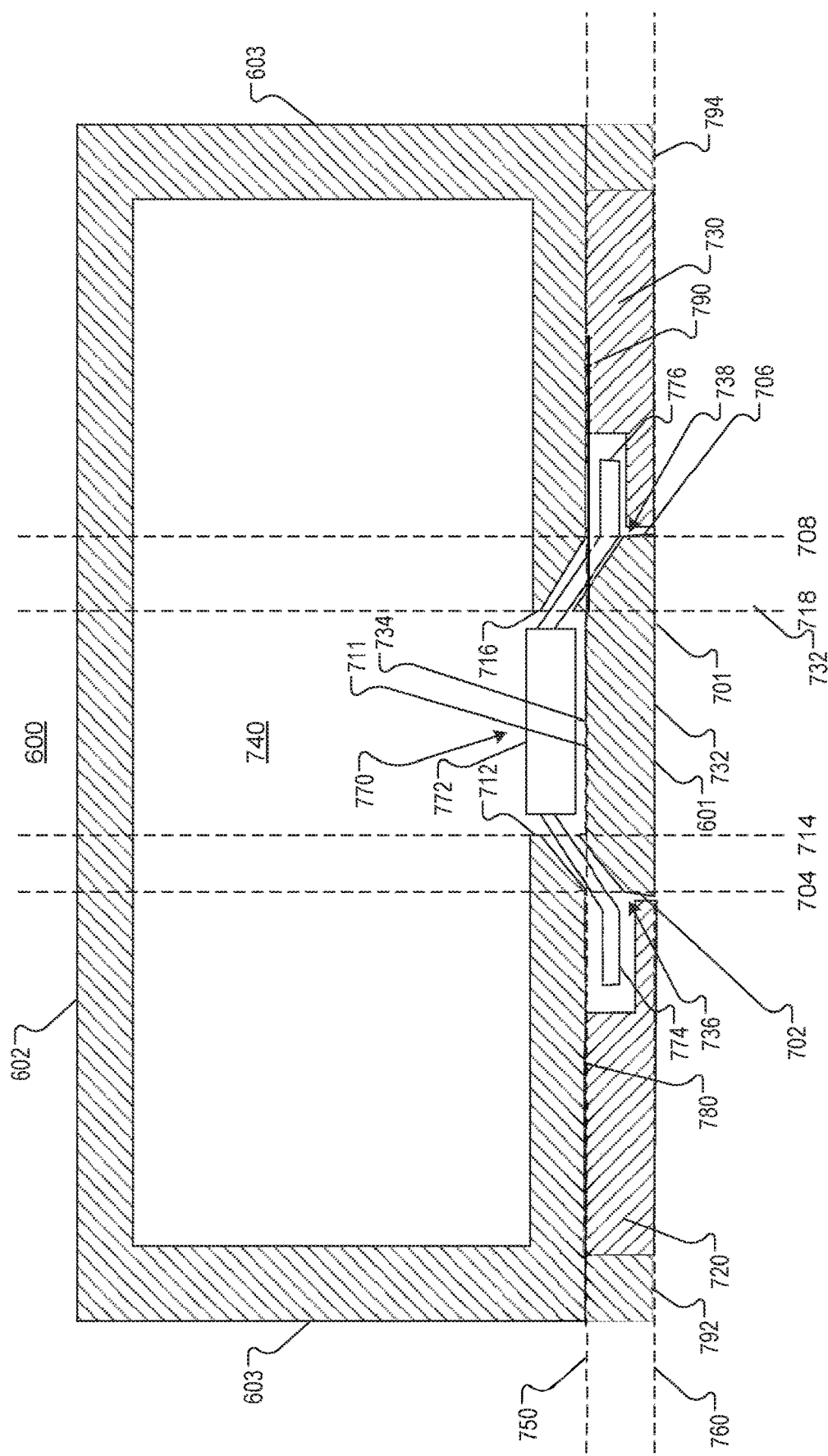

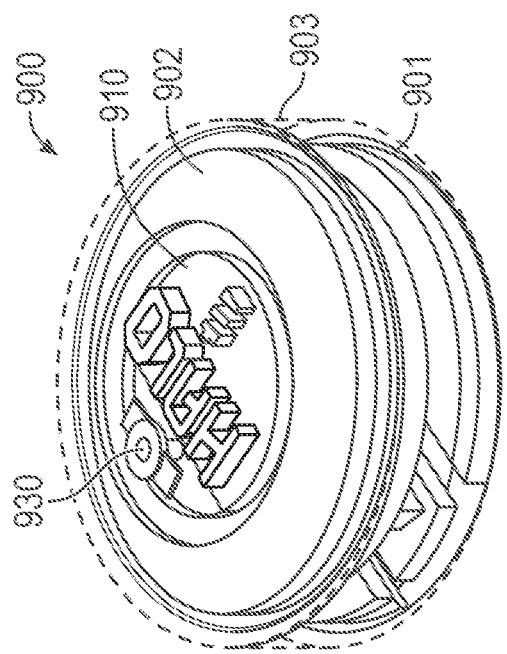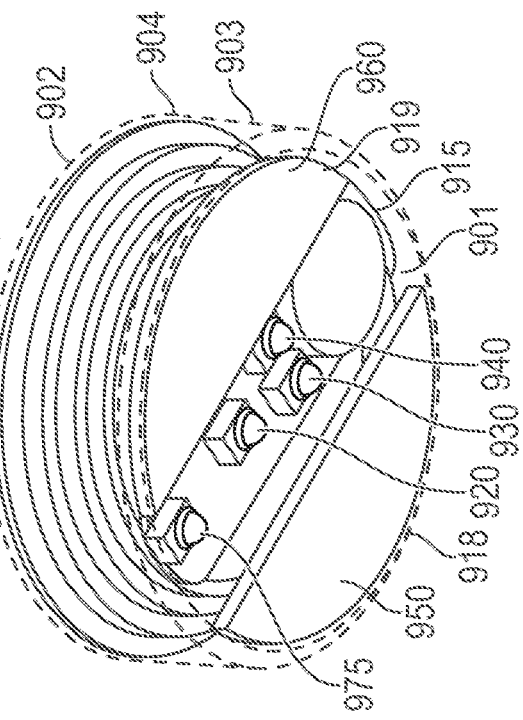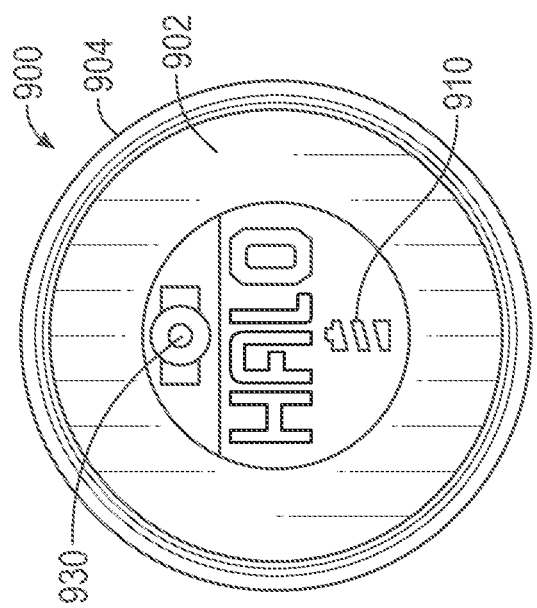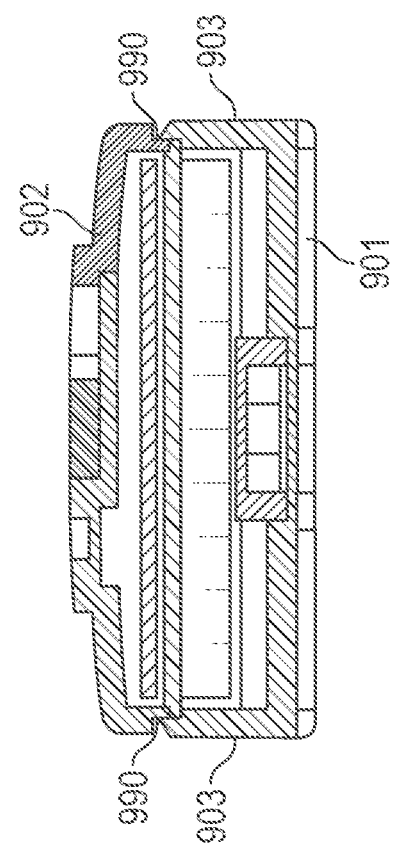
FIG. 9B
FIG. 9D
FIG. 9A
FIG. 9C

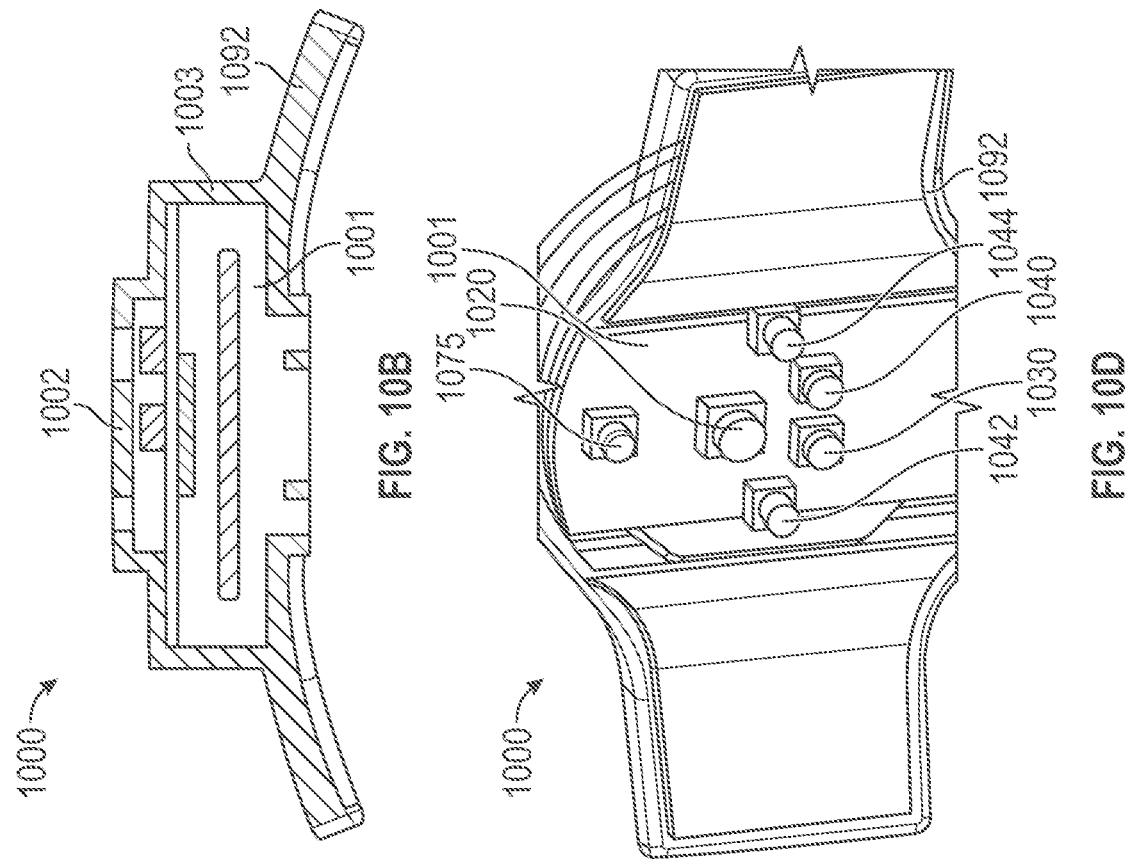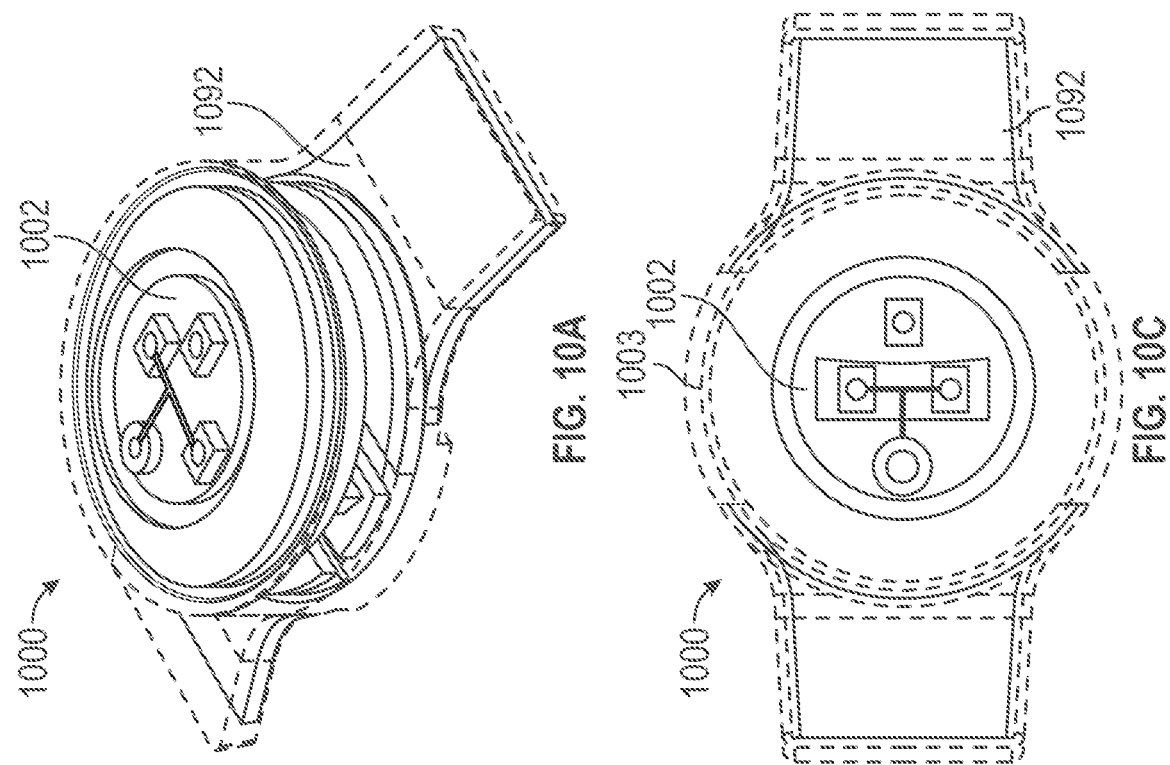

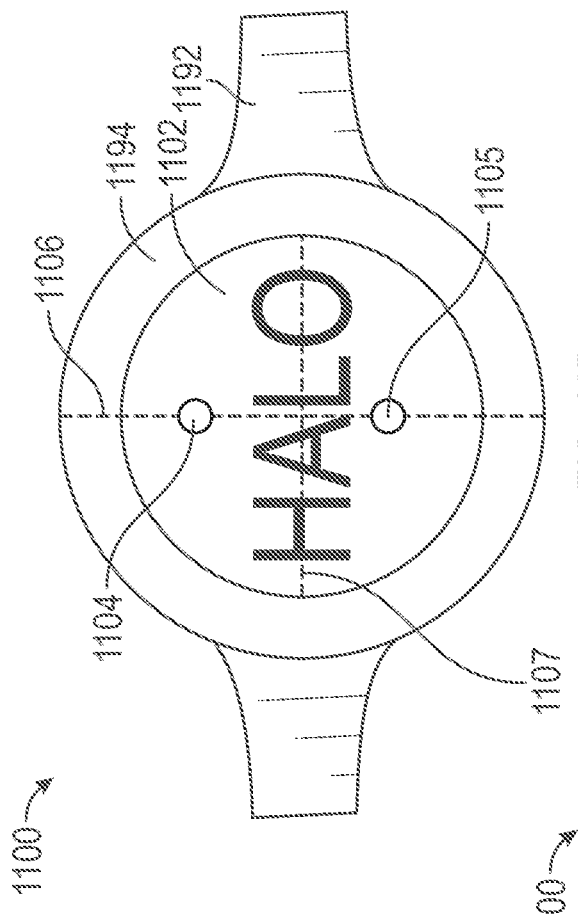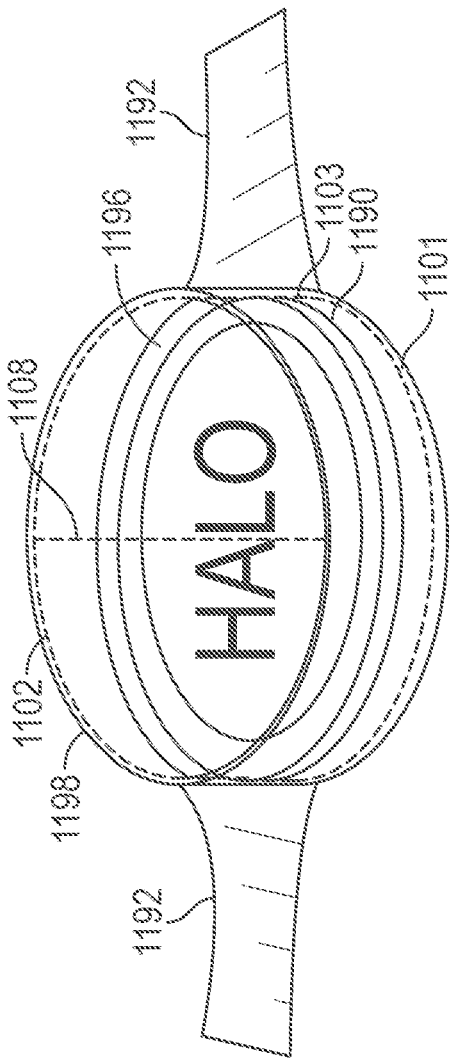

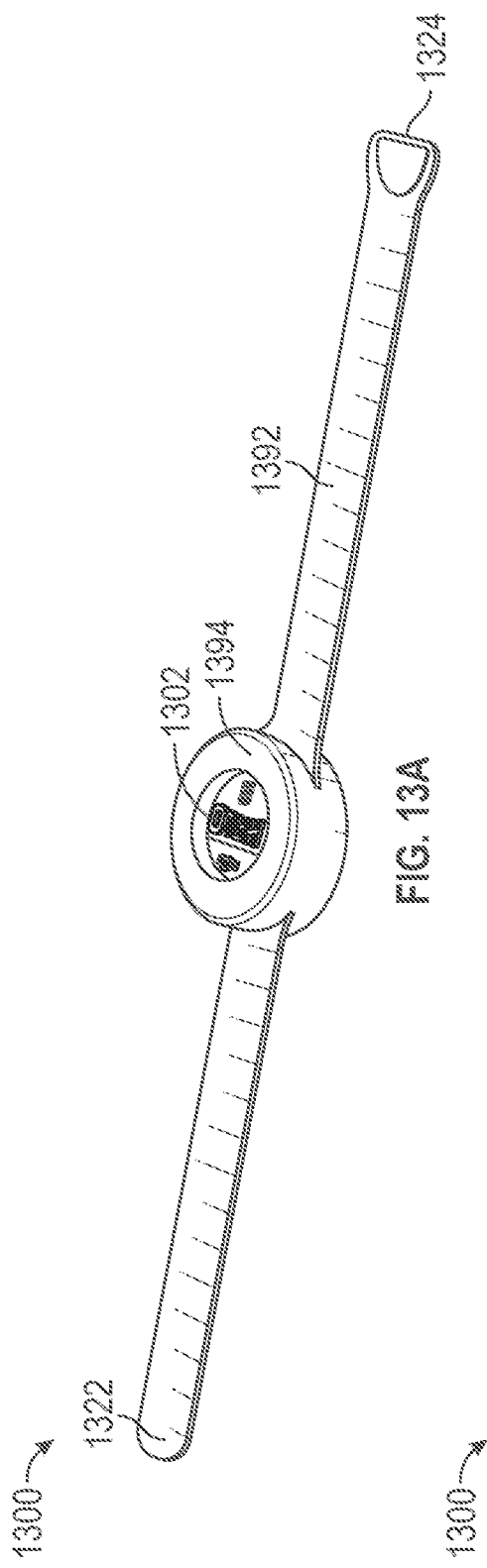
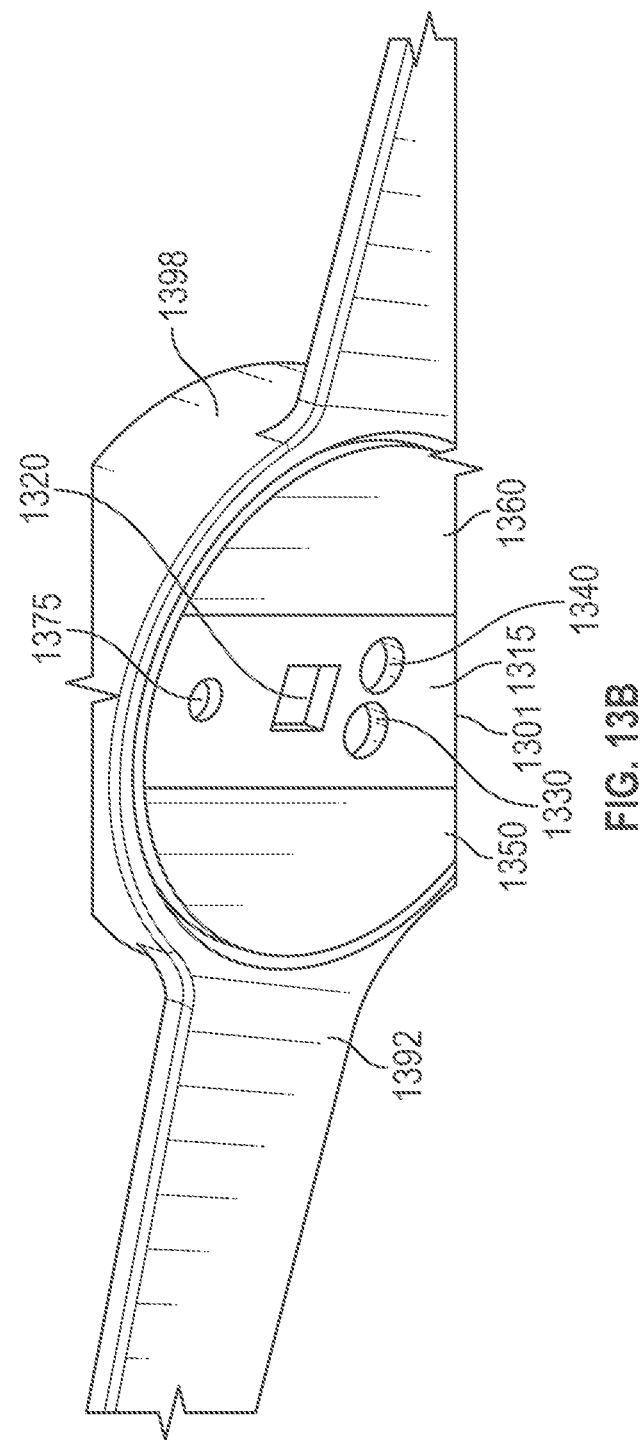

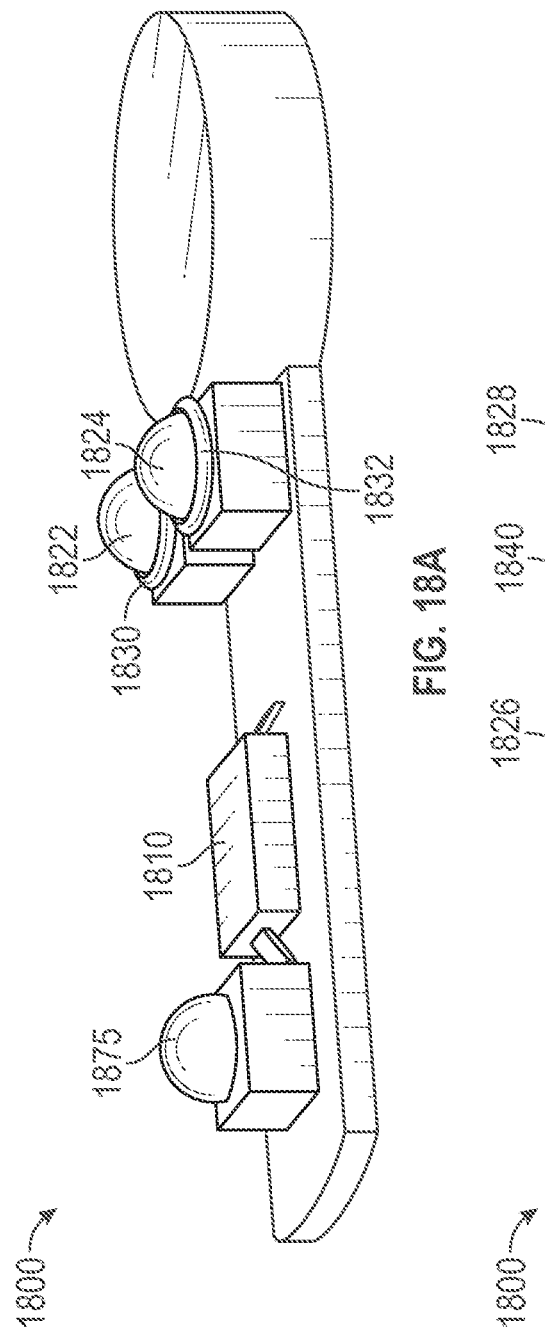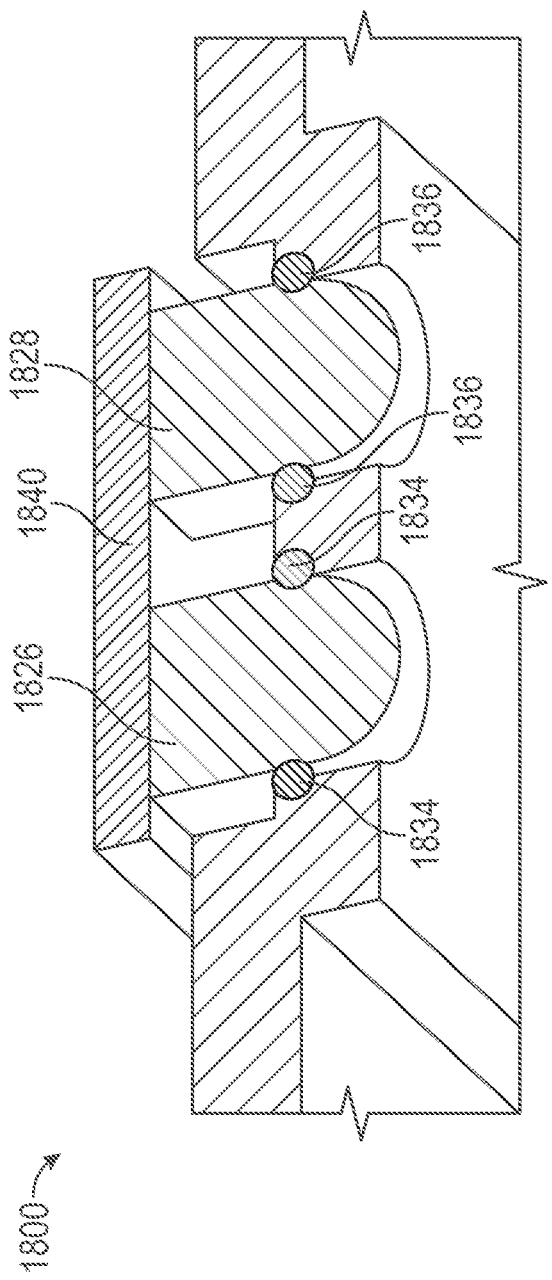
FIG. 18A
FIG. 18B

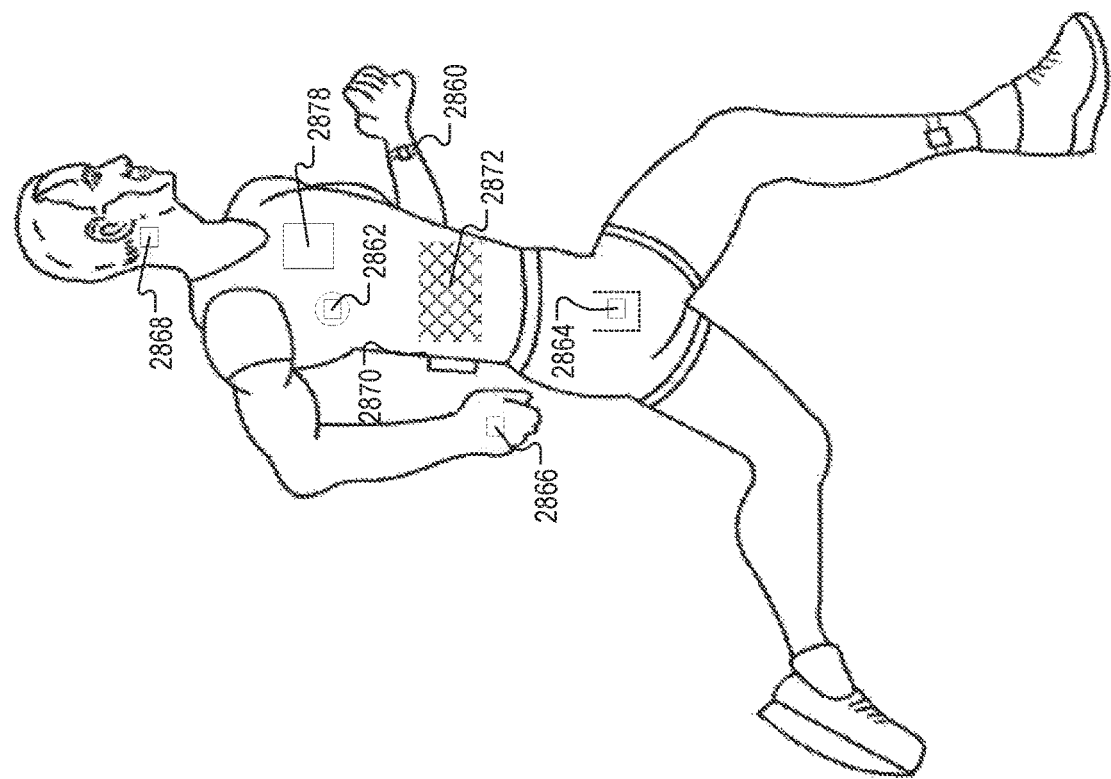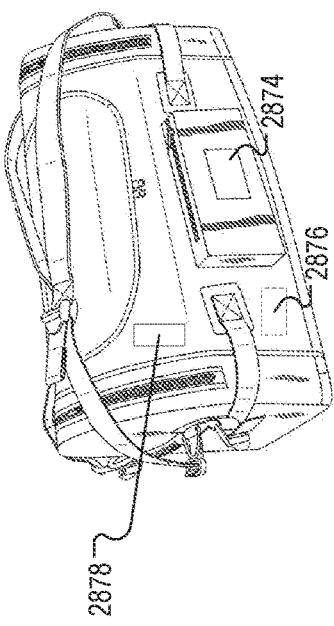
FIG. 28

PHYSICAL STRUCTURE OF WEARABLE DEVICE

RELATED APPLICATIONS

This application is a continuation of U.S. patent application Ser. No. 14/985,245 filed Dec. 20, 2015, which claims the benefit of U.S. Provisional Application No. 62/117,282, filed Feb. 17, 2015 and U.S. Provisional Application No. 62/192,932, filed Jul. 15, 2015. The entire contents of the foregoing referenced applications are incorporated herein by reference.

BACKGROUND

Dehydration is a condition in which water in a living body decreases below the individual's normal functioning level. Dehydration often occurs when an individual is exercising for extended periods of time, an individual intakes little or no water, or the temperature rises to a point where an individual cannot excrete enough sweat to maintain their normal body temperature. Persons that regularly exert themselves in low humidity and/or high temperature conditions and/or for extended periods of time are prone to experience dehydration or dehydration symptoms. Elderly persons and children are also especially prone to experience dehydration or dehydration symptoms.

BRIEF DESCRIPTION OF THE DRAWINGS

The disclosure will be understood more fully from the detailed description given below and from the accompanying drawings of various embodiments of the disclosure. The drawings, however, should not be taken to limit the disclosure to the specific embodiments, but are for explanation and understanding only.

FIG. 7B illustrates a section view of an electronic device, according to another embodiment.

FIG. 9A illustrates a top view of an electronic device, according to one embodiment.

FIG. 9B illustrates a side view of an electronic device, according to one embodiment.

FIG. 9C illustrates a perspective view of an electronic device, according to one embodiment.

FIG. 9D illustrates a perspective view of an electronic device, according to one embodiment.

FIG. 10A illustrates a top perspective view of an electronic device, according to one embodiment.

FIG. 10B illustrates a top view of an electronic device, according to one embodiment.

FIG. 10C illustrates a side view of an electronic device, according to one embodiment.

FIG. 10D illustrates a bottom perspective view of an electronic device, according to one embodiment.

FIG. 11A illustrates a side view of an electronic device, according to one embodiment.

FIG. 11B illustrates a top view of an electronic device, according to one embodiment.

FIG. 11C illustrates a view of the bottom surface of an electronic device, according to one embodiment.

FIG. 13A illustrates a view of the top surface of an electronic device, according to one embodiment.

FIG. 13B illustrates a view of the bottom surface of an electronic device, according to one embodiment.

FIG. 18A illustrates an optical sensor and multiple light sources, according to one embodiment.

FIG. 18B illustrates multiple light sources embedded into a bottom wall of an electronic device, according to one embodiment.

FIG. 28 illustrates body area network (BAN) devices communicating using a BAN, according to one embodiment

DESCRIPTION OF EMBODIMENTS

Figure 1:
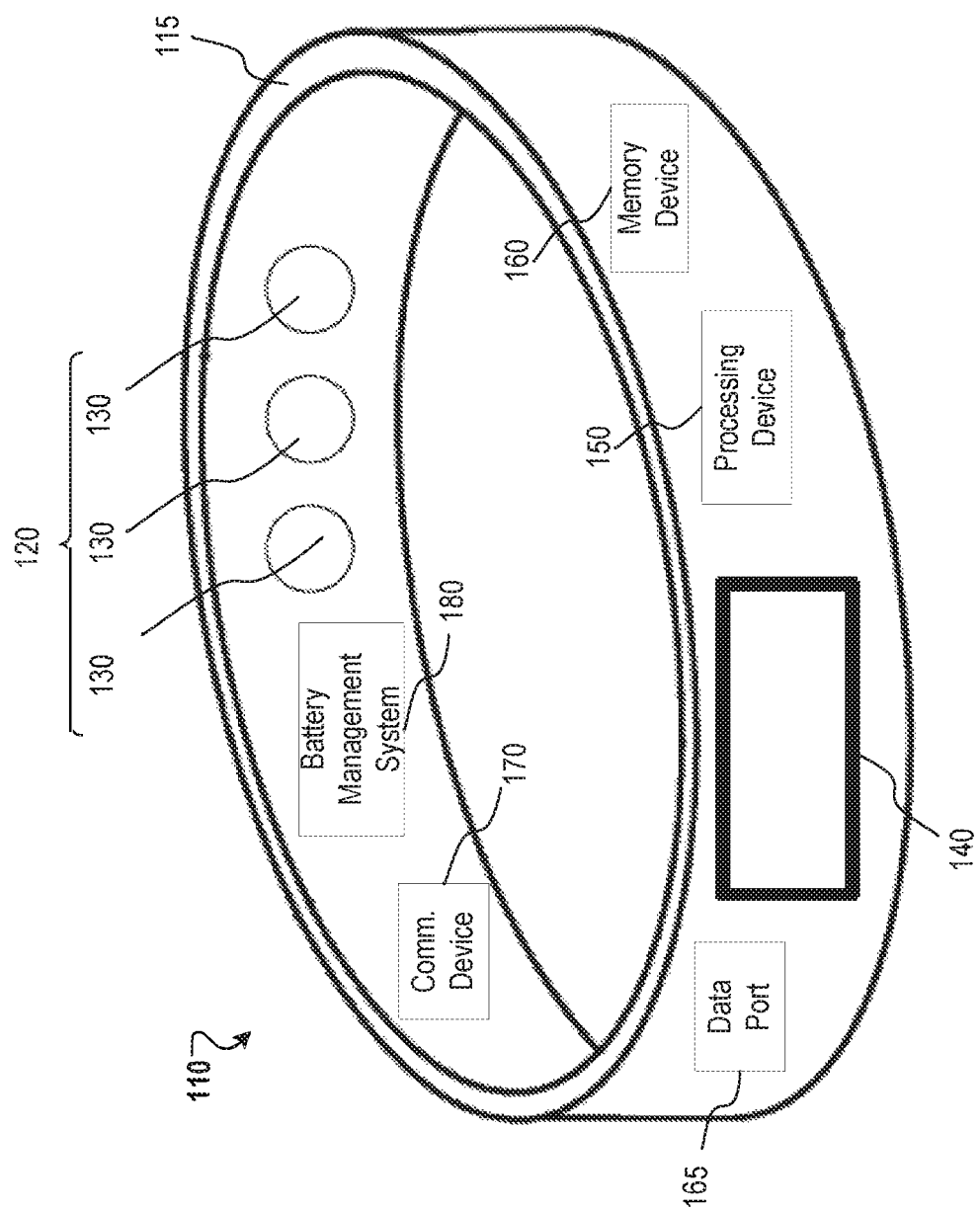
FIG. 1 illustrates an electronic device, according to one embodiment.

When a person experiences a dehydrated condition, the individual's ability to perform tasks will begin to deteriorate. For example, in the case of long distance endurance athletes, an individual that becomes dehydrated by loss of as little as 2% body weight may begin to have their performance impaired. Losses in excess of 5% of body weight can decrease the capacity of an individual to perform a task by as much as 30%.

Conventionally, an individual's hydration level is determined by different tests. One test is a body mass test where an individual is periodically weighed on a scale. Another test is a blood test where blood is drawn periodically to test hemoglobin concentration and hematocrit, sodium concentration, or osmolality. Another test is a urine test where urine is sampled periodically such as a 24-hour urine collection to test osmolality, specific gravity, conductivity, color, volume, or frequency. Another test is a saliva test where saliva is periodically tested for flow rate, osmolality, or composition. One or more of these tests may be performed in a clinic or in a research lab. One or more of the tests may be performed at home over time with periodic measurements and observations. The conventional tests take time, calculations, measurements, and record keeping and in some cases are invasive to the individual and require a laboratory. The conventional tests may also increase a potential biohazard risk as various people have differing involvement with each of these processes. For example, a person may take a urine or saliva sample and then not properly dispose of the sample. There is a need for devices and methods to monitor an individual's hydration condition regularly in a non-invasive manner.

Methods and devices to measure a hydration condition are disclosed herein. A hydration condition may be a current hydration condition or a future hydration condition. The hydration condition may be in the form of a score or index (e.g., Halo score, Halo index, and so forth). In one embodiment, an individual's hydration level is monitored regularly and any change in hydration is detected in the early stage before an individual's performance levels are impacted or they reach a serious hydration condition. A hydration condition can be determined by a measurement of tissue water through impedance spectroscopy. A hydration condition can be determined by a measurement of the circulating blood structure through light emission and optics. A hydration condition can be determined by a total body weight change (TBWC) measurement through sweat rate measurements. A hydration condition can be determined by a measurement of an ambient condition (e.g., one or more of ambient temperature, ambient humidity, and airflow, and so forth) and skin temperature. A hydration condition may be determined by any one or a combination of the abovementioned measurements.

A device may perform one or more of the measurements to determine a hydration condition. The device may combine two or more measurements to determine a more precise hydration condition (e.g., a reduction in an error range, a reduction in a number of errors, an increase in accuracy, and so forth). The device may be a wearable device, an implanted device, and so forth.

An electronic device may have a housing with an inner cavity to house electronic components as discussed below. The housing can include a top wall, a bottom wall, and a perimeter wall that form the inner cavity. A wall (e.g., top wall, bottom wall, perimeter wall, and so forth) of the housing may be a barrier, a layer, a composite, an area, and so forth. An external surface of the bottom wall may have a projection and an inner surface of the bottom wall may have a channel. In one embodiment, a flexible circuit board may have a first portion disposed in the channel, a second portion that extends through a first side wall of the channel to a first recess in the external surface of the bottom wall, and a third portion that extends through a second side wall of the channel to a second recess in the external surface of the bottom wall.

In one embodiment, the electronic device may have a first impedance pad on the second portion in the first recess and a second impedance pad may be on the third portion in the second recess. The electronic device may determine a hydration condition with the first impedance pad and the second impedance pad through bioelectric impedance. Bioelectric impedance measures the resistance of body tissues to the flow of an electric signal. Electric signals flow more easily through parts of the body that have high concentrations of water such as blood, urine, and muscle. Moreover, as skin becomes wet, electric signals begin to flow more easily through the skin. Under dry conditions skin of the human body can have a resistance of up to 100,000 ohms. Conversely, wet or broken skin may drop the skin's resistance to 1,000 ohms.

The human skin is composed of multiple skin layers. The top layer of skin, the epidermis, is responsible for making new skin cells, giving skin its color and protecting the body. Under the epidermis layer is the dermis layer. The dermis layer among other functions produces sweat. Sweat is developed in the dermis layer and travels through skin pores to reach the surface of the body. In one example, an electric signal traveling through dermis layer will encounter less impedance as the body perspires because sweat, a conductive substance, will allow the electric signal to flow more easily. Thus, by measuring the impedance of an electric signal that has traveled through the dermis layer, a hydration condition can be determined. Alternatively, an impedance measurement can be taken in the epidermis or other layer of the skin where sweat is also present.

The electronic device may determine a hydration condition from an impedance measurement. The first impedance pad may transmit an electric current into a body and the second impedance pad may detect a portion of the electric current from the body at a depth below a surface of the body to determine an impedance measurement to determine a hydration condition.

In another embodiment, the electronic device may have an optic sensor and one or more light sources to determine a hydration condition through spectrophotometry. Spectrophotometry is used to measure how much a substance absorbs light by measuring the intensity of a beam of light after the beam of light passes through a sample of the substance. Light can either be absorbed into a substance or it can be reflected by the substance. The presence of certain substances determines which wavelengths are reflected and which are absorbed. Hemoglobin, potassium, and sodium absorb wavelengths of light at specific frequencies. For example, sodium may absorb wavelengths between 535 nanometers and 735 nanometers. In another example, potassium may absorb wavelengths between 680 nanometers and 880 nanometers. In another example, hemoglobin absorbs wavelengths of light that are approximately 660 nanometers, 940 nanometers, and 1320 nanometers. Thus, by emitting light with a specific wavelength corresponding to a substance and measuring the intensity of the light at the specific wavelength after it has passed through the substance, it is possible to determine how much of the salt or compound exists in a given sample.

In one example, measuring the level of a key substance in the human body may indicate a hydration condition of the body. For example, the level of electrolytes in a living body may operate as an indicator to the hydration condition of the living body. Electrolytes are salts carrying an electric charge that reside in the blood stream and other body fluids. Electrolytes affect the amount of water in the body, acidity of the blood (pH), muscle function, and other important processes. These electrolytes are lost when the body perspires. Specifically, when a person becomes dehydrated, the skin pulls fluid from the blood causing the blood to become more concentrated with substances such as sodium and potassium. Two key electrolytes, potassium and sodium, help regulate the water balance in the blood and other bodily tissue. Potassium is an important body salt that is important to both cellular and electrical functions in the body. Additionally, potassium is one of the main salt in the blood considered to be an "electrolyte", along with sodium and chloride. Sodium and potassium regulate the water balance in the blood stream and other bodily tissues.

The electronic device may determine a hydration condition from backscatter measurements. In one example, light reflected by bodily tissue is referred to as backscatter. The electronic device may have an optic sensor and one or more light sources may be disposed on the first portion of the flexible circuit board. The light sources may extend through the projection in the bottom wall of the electronic device and the optical sensor may be disposed adjacent to a transparent material in an opening in the projection in the bottom wall of the hydration. A first light source may emit light at a first wavelength into the body and a second light source may be operable to emit light at a second wavelength into the body. The optical sensor may measure the backscatter of the light reflected by a structure of the body, such as a muscular-walled tube of the body at a depth below the surface of the body to determine an individual's hydration level. In one embodiment, the reflection is a mirrored reflection. In another embodiment, the reflection is a diffused reflection. The preceding examples are not intended to be limiting. The number of light sources is not limited the first and second light source. In other embodiments, the electronic device can include one or a plurality of light sources. Additionally, the number of optical sensors and the distance between the optical sensors is not intended to be limiting. The electronic device can include a one or a plurality of optical sensors at various distances between the optical sensors and the various light sources.

In another embodiment, the electronic device may have a first humidity sensor, second humidity sensor, first temperature sensor, and second temperature sensor to determine a hydration condition by determining the individual's sweat rate. Sweat rate measurements over time can indicate how much water an individual has lost. In one example, a first humidity measurement and a first temperature measurement of an individual may be measured. A first vapor pressure measurement of the individual may be calculated from the first humidity measurement and the first temperature measurement. A second humidity measurement and a second temperature measurement of an individual may be measured. A second vapor pressure measurement of the individual may be calculated from the second humidity measurement and the second temperature measurement. The individual's sweat rate may be determined from the first vapor pressure measurement and the second vapor pressure measurement.

The electronic device may determine a hydration condition from a sweat rate measurement. The electronic device may have a flume extending from the bottom wall to the top wall. A first humidity sensor, second humidity sensor, first temperature sensor, and second temperature sensor may be located in the flume to provide a first humidity, second humidity, first temperature, and second temperature measurements to calculate a first vapor pressure measurement and a second vapor pressure measurement. The first and second humidity sensors may be spaced far enough apart to be able to measure a difference in humidity between the two sensors, but close enough together to fit within the electronic device and to not be affected by ambient humidity. Spacing for the temperature sensors should also be spaced far enough apart to be able to measure a difference in temperature between the two sensors, but close enough together to fit within the electronic device and to not be affected by ambient temperature. A sweat rate may be calculated from the first and second vapor pressure measurements to determine a water loss. An initial hydration condition may be determined from user information. An adjusted hydration condition may be determined from the initial hydration condition and the water loss.

In one embodiment, the electronic device may have an ambient temperature sensor, an ambient humidity sensor, an airflow sensor, and a skin temperature sensor to determine an individual's hydration level through measurements of an ambient condition (e.g., a combination of two or more of ambient temperature, ambient humidity, and airflow, and so forth) and skin temperature. The hydration condition of an individual can be influenced by many factors including airflow, ambient temperature, ambient humidity, and skin temperature. The hydration condition of an individual may be affected as the temperature rises and as the temperature lowers.

For example, the body temperature rises when the ambient temperature is higher than the skin temperature. The body will transport heat through sweat to the surface of the body, but heat dissipation will only occur as the sweat evaporates from the body. If the sweat evaporation rate is lower than the sweat rate, the sweat rate may increase in an attempt to increase heat dissipation. Airflow can increase the rate of sweat evaporation. High ambient humidity can decrease the rate of sweat evaporation. The ambient temperature, skin temperature, airflow, and ambient humidity can cause an individual's sweat rate to increase and can affect the hydration condition of the individual.

In another example, as the ambient temperature lowers below skin temperature, the body temperature may decrease which may constrict blood vessels to reduce flow of blood to the skin to reduce heat loss from the skin to the environment. The constriction of blood vessels may cause an individual to incorrectly perceive that they are properly hydrated and decrease the individual's thirst response. The constriction of blood vessels may also cause blood pressure to rise and to regulate blood pressure, the kidneys may filter fluid from the blood, filling the bladder with the excess fluid, and increasing urine production. The body's decreased thirst response and increased urine production may affect the body's hydration condition. Airflow can make the apparent temperature feel cooler as the airflow wicks heat away from the body through convection, thereby affecting the body's hydration condition. High humidity can make the apparent temperature feel cooler because the water in the humid air has a higher specific heat than air, therefore cold air with a higher humidity may transfer heat from a body at a higher rate than cold air at a lower humidity, thereby affecting the body's hydration condition. The ambient temperature, skin temperature, airflow, and ambient humidity can cause an individual's blood vessels to constrict and can affect the hydration condition of the individual.

The electronic device may determine a hydration condition from at least one of an ambient condition, a skin temperature, and one or more physiological measurements. The electronic device may have an ambient temperature sensor, an ambient humidity sensor, an airflow sensor, and a skin temperature sensor. An ambient condition may be determined from an ambient temperature measurement, an ambient humidity measurement, and an airflow measurement. An adjusted hydration condition may be determined from the ambient condition and the skin temperature. The adjusted hydration condition may be a current hydration condition, a predicted future hydration condition, and so forth.

The embodiments described herein are directed to devices and methods to determine a hydration condition of an individual by different types of measurements. The measurements may include measuring an individual's hydration level through bio-impedance spectroscopy by measuring the individual's sweat rate, and/or by measurements of an ambient condition (e.g., ambient temperature, ambient humidity, and airflow, and so forth) and skin temperature. The hydration condition of the individual can include a hypo-hydrated level (dehydrated or under hydrated condition), a euhydrated level (normal hydration condition), or a hyper-hydrated level (over hydrated condition). In one embodiment, a measurement may indicate that the individual is trending towards a dehydrated condition. In another embodiment, a measurement may indicate a user is trending towards a normal hydration condition. In another embodiment, a measurement may indicate that the individual is trending towards an over hydrated condition.

FIG. 1 illustrates an electronic device 110, according to one embodiment. FIG. 1 illustrates that the electronic device 110 can be a wristband, a headband, an armband, a chest band, a leg band, an ankle band, a strap, a garment or piece of clothing (such as a hardhat or shirt), an accessory, or other object that can be shaped to attach or couple to a user. The electronic device 110 can also be integrated into other wearable objects such as a hard hat, a safety harness, a safety lock out, shoes, a bag, and so forth.

In one example, the electronic device 100 can be located in an area that is comfortable for the user to wear the electronic device 110 for an extended period of time, such as a 24-hour period. For example, as many individuals are accustomed to wearing wristwatches, a comfortable location for the individual to wear the electronic device 110 for an extended period of time is a wrist location. In another example, the electronic device may be located at a location on the user that will provide highest measurement accuracy level, such as a location on the user that is the most sensitive to a selected physiological measurement. For example, the chest, wrist, tip of the finger, or earlobe may be locations that provide a high level of accuracy to take physiological measurements compared to other locations on the body of the user and the electronic device 110 can be shaped to attach to the user at chest, wrist, tip of the finger, or earlobe locations.

In one embodiment, the electronic device 110 may include a housing 115 with one or more inner cavities. The one or more cavities can include space to house: a sensor array 120, a sensor 130, a display 140, a processing device 150, a memory device 160, a communication device 170, and/or a battery management system (BMS) 180. In one embodiment, the housing 115 can be hermetically sealed, e.g., airtight, waterproof, sweat proof, dust proof, and so forth. In another example, the housing can be a unibody (e.g., a single unit), where components such as the sensor 130 can be sealed within the unibody. In another embodiment, the housing 115 can include multiple pieces, such as a first housing piece and a second housing piece, that are sealed together to form a hermetically sealed housing 115. In another embodiment, the housing 115 can include multiple pieces, such as a first housing piece and a second housing piece that are coupled by at least one of induction connection or electrical connection.

In one example, the electronic device 110 can be an invasive device attachable to (or implantable within) a body of a user to obtain an invasive physiological measurement from the user. In another example, the electronic device 110 can be a non-invasive device attachable to the body of the user to obtain non-invasive measurements from the user.

The electronic device 110 can include a sensor 130 or sensor array 120 that can be integrated into the electronic device 110. In another example, the sensor 130 or the sensor array 120 can be coupled to the processing device 150 of the electronic device 110. In one example, the sensor 130 can be a physiological sensor. The physiological sensor can include an impedance sensor, an optical sensor, an electrocardiography (ECG) sensor, a fluid level sensor, an oxygen saturation sensor, a body temperature sensor (skin temperature or core temperature), a plethysmographic sensor, a respiration sensor, a breath rate sensor, a cardiac sensor, a bioimpedance sensor, a spectrometer, a heart rate sensor, a blood pressure sensor, a pulse oximeter, or other physiological sensors. In another example, the sensor 130 can be a Newtonian sensor. The Newtonian sensor can include: a two-dimensional (2D) accelerometer, a three-dimensional (3D) accelerometer, a gyroscope, a magnetometer, a vibration sensor, a force sensor, a pedometer, a strain gauge, and so forth. In another example, the sensor 130 can be a location sensor. The location sensor can include: a global positioning system (GPS); a triangulation system; and so forth. In another example, the sensor 130 can be an environmental sensor. The environmental sensor can include: a humidity sensor, an ambient temperature sensor, an altitude sensor, a barometer, a weather sensor, and so forth. In one embodiment, the sensor 130 can be a non-invasive sensor. In one embodiment, one or more of the physiological sensors, the Newtonian sensors, or the environmental sensors can be integrated into the electronic device 110 or physically coupled to the electronic device 110. In another example, one or more of the physiological sensors, the Newtonian sensors, or the environmental sensors can be physically separate from the electronic device 110 and can be communicate data with the electronic device, either directly or indirectly as discussed herein.

In one embodiment, the electronic device 110 can include a display 140 to show information to a user or a third party based on the measurements from the sensor 130 or the sensor array 120. In one embodiment, the display 140 can show the time, e.g., a clock. In another embodiment, the information shown on the display 140 may include measurement information, such as: a light backscatter measurement, a heart rate of a user, a breathing rate of the user, a blood pressure of the user, and so forth. In another example, the information shown on the display 140 may include recommendations, such as: a recommendation to take a break; a recommendation to go home; a recommendation to go to a hospital; or other recommendations. In another example, the information shown on the display 140 may include alerts, such as: an alert that a user may be experiencing a dehydration condition; an alert to take medication; an alert that an environment may not be safe; an alert that the user has fallen down; or other alerts. In another example, the information shown on the display 140 may include: hydration information, health status information, and other information.

In another embodiment, the display 140 can display information to a user or a third party based on information from other devices in communication with the electronic device 110. For example, the electronic device 110 can receive information from an automobile or a smart home device of a user or a third party. In this example, the information from the automobile or the smart home device can include ambient temperatures, humidity information, weather information, and so forth. The electronic device 110 can display the information from the automobile or the smart home device or use it in combination with measurements taken using the sensor 130 or the sensor array 120 to determine and display other information, such as a hydration level of the user.

In another embodiment, the processing logic of the electronic device 110 can determine an error with the sensor 130 or the sensor array 120 and display the error to the user or the third party using the display 140. For example, the processing logic can determine that the sensor 130 or the sensor array 120 is not interfacing with the user properly and the processing logic can use the display 140 to display an error message to the user. In one embodiment, the sensor 130 or the sensor array 120 is not interfacing with the user properly when the sensor 130 or the sensor array 120 is only partially contacting the body of the user or is not completely contacting the body of the user. In another embodiment, the sensor 130 or the sensor array 120 is not interfacing with the user properly when an object or particle is interfering with processing logic using the sensor 130 or the sensor array 120 to take physiological measurements of the user, environmental measurements, or other measurements. In one example, processing logic can determine that object or particle is interfering with taking measurements when measurement information is outside a defined measurement range or there is a discontinuity in the measurement information that exceeds a threshold level for the discontinuity. For example, when dirt comes between the sensor 130 or the sensor array 120 and the body of the user, the dirt can cause a discontinuity in the measurement information. When the processing logic determines the discontinuity in the measurement information, the processing logic can use the display 140 to display an error message associated with the discontinuity.

In another embodiment, the sensor 130 or the sensor array 120 is not interfacing with the user properly when the electronic device 110, the sensor 130, or the sensor array 120 has become dislocated or displaced. For example, measurements taken using the sensor 130 or the sensor array 120 with a first orientation can have a higher accuracy level than measurements taken using the sensor 130 or the sensor array 120 with a second orientation. In one example, the first orientation is an orientation where the user is wearing the electronic device 110 in a correct orientation and the second orientation is an orientation when the electronic device 110 has slipped or shifted to a different orientation. When the electronic device 110 has slipped or shifted the second orientation, the processing logic identifies that a measurement is outside a defined measurement range or there is a discontinuity in measurement information and uses the display 140 to display an error message associated with slippage or shifting.

In one example, the display 140 can be a touch screen display, such as a capacitive touch screen or a resistive touch screen. In another example, the display 140 can display a graphical user interface (GUI) to receive information. In another example, the electronic device 110 can include a data port 165, such as a universal serial bus (USB) port, a mini-USB port, a micro-USB port, a LIGHTNING® port, and so forth. In another example, the electronic device 110 can include a wireless communications device 170 (as discussed in the proceeding paragraphs) to send or receive information. The electronic device 110 can include a processor or processing device 150 to analyze or process measurements, received information, user input data, and/or other types of data.

In one example, the electronic device 110 can monitor stress on a respiratory system of the user. For example, the electronic device 110 can use the sensor 130, such as an oxygen saturation sensor, to monitor the stress on a respiratory system of the user.

In another example, the electronic device 110 can use one or more sensors 130 in the sensor array 120 to monitor stress on one or more systems of a user, such as a biological system or a body system. The biological system may include a respiratory system, a cardiovascular system, a nervous system, an integumentary system, a urinary system, an excretory system, a digestive system, an immune system, an endocrine system, a lymphatic system, a muscular system, a skeletal system, a reproductive system, and other systems. The body system may include two or more organs working together in the execution of a specific bodily function, e.g., a neuroendocrine system, a musculoskeletal system, and so forth. For example, the electronic device 110 can monitor stress on the cardiac system of a user using a blood pressure sensor of the sensor array 120 and can monitor the stress on the respiratory system of the user using an oxygen saturation sensor of the sensor array 120.

In another example, the electronic device 110 can monitor biological systems, organs, body parts, body system, or other areas of a user. In another example, the electronic device 110 can monitor or aggregate stress measurements from the sensors of the sensor array with other measurements, such as a lung capacity of a user, a hematocrit (HCT), an oxygen saturation level, and/or or other medical measurements. In another example, the electronic device 110 can analyze the aggregated measurements to determine stress on one or more biological systems, organs, body parts, and/or body system and use the aggregated measurements to determine medical, health, and/or safety conditions.

In one example, the electronic device 110 can use the sensor array 120 to monitor a medical condition of a user, such as a cardiac condition, under various environments or conditions for continuous, semi-continuous, or a periodic period of time on a long-term or protracted basis. In one example, sensor measurements can be collected using the sensor 130 in the sensor array 120 of the electronic device 110. In another example, the sensor measurements can be stored on a non-tangible computer readable medium device 160 (e.g., a memory device) coupled to the electronic device 110 or in communication with the electronic device 110.

In one embodiment, the battery management system (BMS) 180 can include: one or more batteries (such as a rechargeable battery), a charger, and a management device. The one or more batteries may be located in the housing 115, in a band coupled to the housing, and so forth. The management device can manage and control power, e.g., power to and from the one or more batteries or regulate power of the electronic device 110. For example, the management device can direct power received from an external power source, such as wall outlet, via the data port 165 (e.g., a USB port) and can recharge the one or more batteries. In another example, the BMS 180 can include a wireless power system with a wireless power coil to receive power. In this example, the management device can direct power received via the wireless power system to the one or more batteries. In another example, the management device can direct power to components or systems of the electronic device 110, such as the sensor array 120, the sensor 130, the display 140, the processing device 150, the memory device 160, and/or the communication device 170. In one example, the management device can be a processor or another processing device, independent of the processing device 150, that can manage and control the power. In another example, the management device can be software executed by the processing device 150 or processing logic to manage the power.

In one embodiment, the BMS 180 can determine when a charge level the one or more batteries is below a threshold amount and can send a notification to the user indicating that the electronic device 110 needs to be charged. In one example, the electronic device can send the notification to the user using a sensory device such as a vibrator, a speaker, a display, and so forth.

Figure 2B:
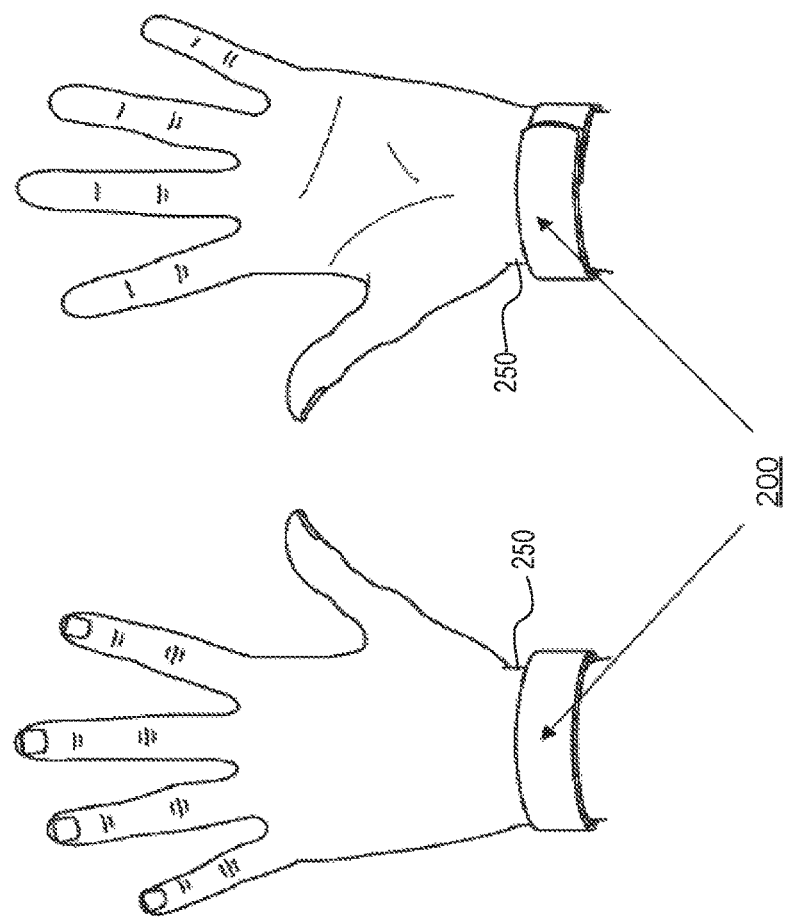
FIG. 2B illustrates a top and a bottom perspective of an electronic device attached to a wrist of a user, according to one embodiment.
Figure 2A:
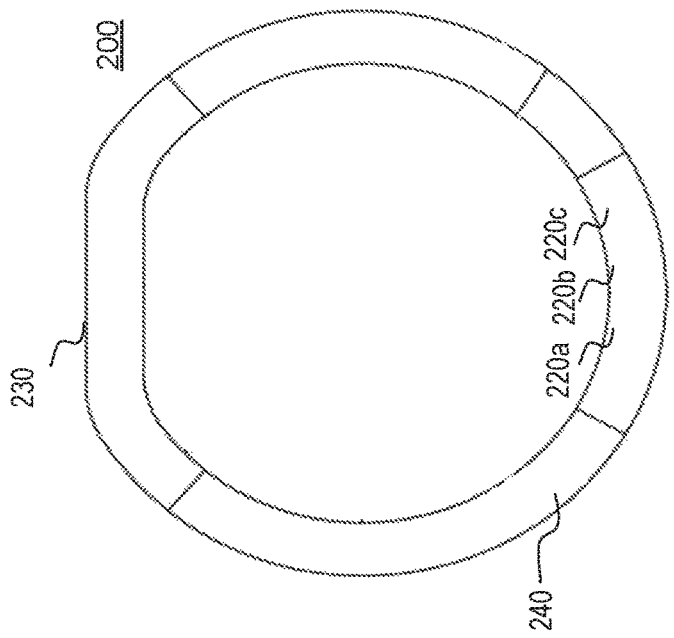
FIG. 2A illustrates a side view of an electronic device, according to one embodiment.

FIG. 2A illustrates a side view of an electronic device 200, according to one embodiment. The electronic device 200 can include one or more integrated sensors 220. In one exemplary embodiment, the electronic device 200 can have a flat top portion 230 and a circular remaining portion 240 to fit to the contour or shape of a wrist on a user. The electronic device 200 may be disposed on the contours of the wrist to align the sensors 220 of the electronic device 200 with a specific location on the wrist of the user (such as a bottom, side, or top of the wrist). The electronic device 200 fitting to contours of the wrist can be to provide and/or maintain proper contact between the sensor 220 of the electronic device 200 and a body of the user. The location of the sensors 220 is not intended to be limiting. The sensor 220 can be located at different locations on the electronic device 200. Additionally, a shape of the electronic device 200 is not intended to be limiting. The electronic device 200 can be a variety of different shapes, such as oval, circular, rectangular, and so forth.

FIG. 2B illustrates a top and a bottom perspective of an electronic device 200 attached to a wrist 250 of a user, according to one embodiment. The reference numbers in FIG. 2B can have the same numbers as in FIG. 2A to indicate the same or similar features or components as shown in FIG. 2A. However, the features or components of FIG. 2A are not intended to be limiting and other features or components can be used. The electronic device 200 may be located on the wrist of a user and may take one or more measurements at the wrist location. In one example, the electronic device 200 can cover or wrap around the circumference of the wrist 250 of the user.

Figure 3:
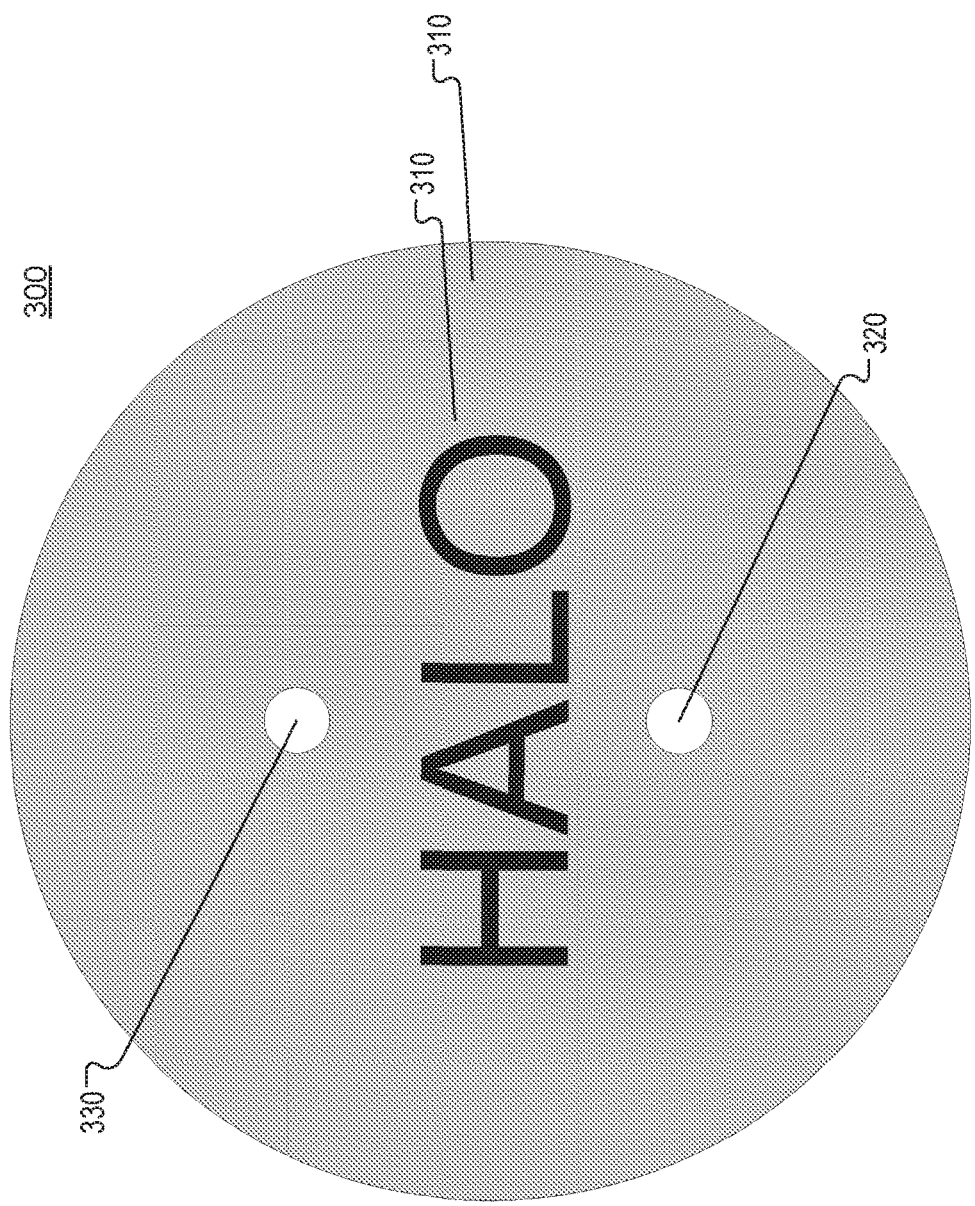
FIG. 3 illustrates a top view of an electronic device, according to one embodiment.

FIG. 3 illustrates a top view of an electronic device 300, according to one embodiment. The electronic device 300 may have a top wall 302 that includes a display 310 on the exterior surface of the top wall 302. The top wall 302 may have a perimeter 304. The display 310 may provide information to a user such as indicating the user's hydration condition, temporal information such as the user's hydration condition over time, a time and date, and any information about a user's physiological state. In one embodiment, the display 310 may be a graphical user interface (GUI) that allows a user to interact with the device. In another embodiment, the display may be located on an external device, such as a cellular telephone, a personal computer, or other mobile device. The electronic device 300 may further include a power and charging indicator 320 to indicate a state of the electronic device 300. In another embodiment, the electronic device 300 may include one or more ports such as a humidity, airflow, and/or temperature sensor port 330. In another embodiment, the electronic device 300 may include one or more sensors such as humidity, airflow, and/or temperature sensors which may be located on the surface (e.g., exterior surface of a perimeter wall, top wall 302, or bottom wall, and so forth) of the electronic device 300 or inside the humidity, airflow, and/or temperature sensor port 330. In one embodiment, a humidity sensor may detect the humidity level of the user's environment or a sweat rate of a user. A temperature sensor may detect the temperature of the user's environment or a surface temperature of a user. An airflow sensor may detect one or more measurements (e.g., first and second pressure measurements, first and second temperature measurements, and so forth) from which the airflow rate of the user's environment may be calculated.

Figure 4:
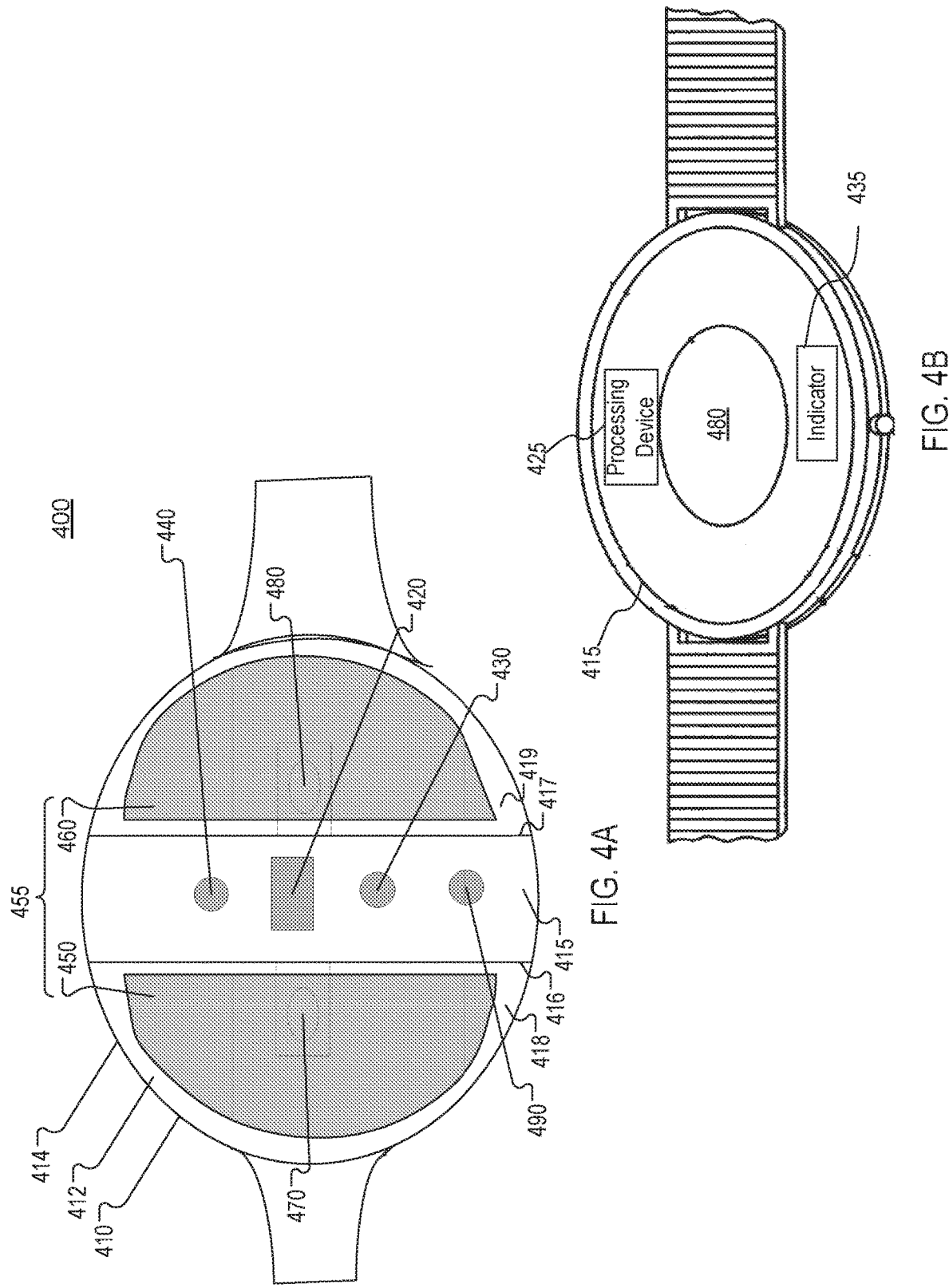
FIG. 4A illustrates bottom surface of an electronic device, according to one embodiment.
FIG. 4B illustrates a view of a bottom surface of an electronic device, according to one embodiment.

FIG. 4A illustrates a bottom view of an electronic device 400, according to one embodiment. The electronic device 400 includes a housing 410, an optical sensor 420, light sources 430 and 440, an impedance sensor 455 having impedance pads or contact terminals 450 and 460, contact wings 470 and 480, and one or more ports such as a humidity, airflow, and/or temperature sensor port 490. The port 490 may be an inlet to a flume.

The housing 410 of the electronic device 400 may have a bottom wall 412 that has a perimeter 414. A perimeter wall may be disposed around perimeter 414 of the housing 410. The perimeter wall may be disposed between the bottom wall 414 and the top wall. The top wall, bottom wall 414, and the perimeter wall may form an inner cavity. The housing 410 may be cylindrical. The bottom wall 412 may include a section that projects out from a first plane to a second plane to form a projection 415 on an external surface of the bottom wall 412 and a channel on an internal surface of the bottom wall 412. The bottom wall 412 may form a first recess 418 on a first side of the projection 415 between a first and second planes and the external surface of the bottom wall 412 in the first plane. The bottom wall 412 may form a second recess 419 on a second side of the projection 415 between the first and second planes and the external surface of the bottom wall 412 in the first plane.

In one embodiment, the electronic device 400 includes impedance sensor 455 having impedance pads 450 and 460. A first portion of a flexible circuit board may be disposed on the channel in the inner cavity. Contact wing 470 may be a second portion of the flexible circuit board and contact wing 480 may be a third portion of the flexible circuit board. Contact wing 470 may extend from the first portion of the flexible circuit board in the inner cavity of the housing 410, through a first opening through a first side wall 416 of the projection 415 and may affix to the surface of the first recess 418. Contact wing 480 may extend from the first portion of the flexible circuit board in the inner cavity of the housing 410, through a second opening through a second side wall 417 of the projection 415 and may affix to the surface of the second recess 419. Impedance pad 450 may be located on contact wing 470 in the first recess 418 and impedance pad 460 may be located on contact wing 480 in the second recess 419. Impedance pad 450, impedance pad 460, and projection 415 may be substantially coplanar in the second plane. Impedance sensor 455 may cause impedance pad 450 to send an electrical signal into a body. The impedance pad 460 may detect at least a portion of the electrical signal in the body. In one embodiment, the impedance sensor 455 can detect a change in the impedance of the body. The change in the impedance of the body can indicate that a change in a hydration condition of the body has changed. For example, as a level of the impedance increases, the hydration condition of the body may increase in dehydration. In another example, as a level of the impedance decreases, the hydration condition of the body may increase in hydration. The impedance sensor 455 may be coupled to a processing device and a sensor interface through contact wings 470, 480.

The housing 410 of the electronic device 400 may be shaped to affix to the wrist, head, arm, chest, leg, ankle, earlobe, fingertip, or other surface of the body to determine a hydration 1 condition of the body. In one embodiment, one or more components of the electronic device 400 may be located adjacent or pass through a wall (e.g., the bottom wall 412, perimeter wall, top wall, and so forth) of housing 410. The sensor components such as the optical sensor 420, light sources 430 and 440, impedance pads 250 and 260, and one or more ports such as a humidity, airflow, and/or temperature sensor port 490 may pass through the bottom wall 412 of the housing 410 of the electronic device 400. In another embodiment, the underside of the housing 410 may be defined by a plane and one or more of the sensor components may sit flush with the plane such that when affixed to a user, the sensor components contact the skin of the user without extending beyond the plane. In another embodiment, the underside of the housing 410 may be defined by a plane and one or more of the sensor components may extend beyond the plane such that when affixed to a user, the sensor components contact the skin of the user and cause a slight indentation in the skin of the user by extending beyond the plane.

The projection 415 may have a third opening. There may be a transparent material (e.g., glass, plastic, and so forth) disposed in the third opening. There may be a sealing structure (e.g., O-ring, epoxy, etc.) disposed around the transparent material to hermetically seal the third opening to prevent fluid from passing through the third opening. The optical sensor 420 may be disposed adjacent to the transparent material. The optical sensor 420 may be substantially flush with the interior surface of the transparent material. The exterior surface of the transparent material may be substantially coplanar with the second plane, the exterior surface of the projection 415, and the impedance pads 450 and 460. The light sources 430 and 440 may be equidistant from the optical sensor 420. The light sources 430 and 440 may be located on the same side of the optical sensor 420 as shown in FIG. 9D.

The projection 415 may have one or more light source openings. Each of the light sources 430 and 440 may extend through a light source opening and a sealing structure may be disposed around each light source 430 and 440 to hermetically seal the light source opening to prevent fluid from passing through the light source opening. The end of each light source opening may be substantially coplanar with the second plane, the exterior surface of the projection 415, and the impedance pads 450 and 460. In one embodiment, maintaining the transparent material of the optical sensor 420 and light sources 430 and 440 flush with or slightly indenting into the skin of the user may help reduce light piping (e.g., the optical sensor 420 sensing light from the light sources 430 and 440 that has not entered the skin of the user). In another embodiment, opaque material is used between the optical sensor 420 and light sources 430 and 440 to reduce light piping.

The openings for the optical sensor 420, light sources 430 and 440, and so forth may be hermetically sealed (e.g., by use of at least one of a sealing structure, a gasket, an O-ring, epoxy, and so forth).

In one embodiment, the bottom wall 412 may be formed so that the channel of the bottom wall 412 in the inner cavity has a slope. In one embodiment, a ramp may be disposed in the channel of the bottom wall 412 to provide a slope. The light sources 430 and 440 may extend further out from the first portion of the flexible circuit board than the optical sensor 420. The slope may allow the light sources 430 and 440 to be flush with the external surface of the projection 415, the optical sensor 420 to be flush with the transparent material disposed in the projection 415, and the transparent material to be flush with the external surface of the projection 415. Maintaining the light sources 430 and 440, transparent material, and optical sensor 420 flush as described above may help avoid inference from light not radiating from the skin and may help radiate the light from the light sources 430 and 440 into the skin.

The housing 410 may have a central axis passing through the center of the top wall and the bottom wall 412. The optical sensor 420 and the light sources 430 and 440 may be substantially centered about the central axis.

The light sources 430 and 440 may extend further from the flexible circuit board than the optical sensor 420. A portion of the inside surface of the projection (i.e., in the inner cavity) may have a slope to allow the light sources 430 and 440 to be substantially flush with the external surface of the bottom wall 412 in the second plane and the optical sensor 420 to be substantially flush with the inside surface of the transparent material (i.e., in the inner cavity). The exterior surface of the transparent material may be substantially coplanar with the external surface of the bottom wall 412.

In one embodiment, the optical sensor 420 and the light sources 430 and 440 may be located in or adjacent in the bottom wall 412 located between impedance pads 450 and 460. In one embodiment, the light sources 430 and 440 are light emitting diodes (LEDs). In another embodiment, light sources 430 and 440 may include incandescent light sources, halogen light sources, or the like. In one embodiment, light sources 430 and 440 may emit full spectrum of light into a body. In another embodiment, the light sources 430 and 440 may emit discrete wavelengths of light into a body. The discrete wavelengths may correspond to measurements of potassium, sodium, hemoglobin, or other substances in the blood stream or other bodily tissue.

In one embodiment, optical sensor 420 is to detect an intensity of one or more wavelengths of light reflected by bodily tissue of a user. The optical sensor 420 may be coupled to a processing device and a sensor interface. The sensor interface may receive the detected light from the optical sensor 420 and measure the amount of light received as a specific wavelength that has been detected. In one embodiment, the optical sensor 420 is used in concert with other components (e.g., impedance sensors, temperature sensors, humidity sensors, airflow sensors, and so forth) of the electronic device 400 to determine a hydration condition of the body of a user. The determination can be made by measuring the concentration levels of substances, such as electrolytes, in the body. For example, when the sensor interface measures a decrease in backscatter (e.g., light reflected by bodily tissue, and so forth) of wavelength, compared to a previous measurement, corresponding to sodium in a muscular walled tube of the body of a user, the sensor interface may determine that the user's sodium level in the blood stream is increasing and the hydration condition of a user is declining. In one embodiment, the GUI or display may inform the user that they are becoming dehydrated. In one embodiment, the measurement is taken from a muscular-walled tube of the body such as a vein, artery, or the like. The measurement can be taken from other bodily tissues as well.

In one embodiment, the electronic device 400 includes one or more ports such as a humidity, airflow, and/or temperature sensor port 490. In one example, the humidity and/or temperature sensors in the humidity and/or temperature sensor port 490 may perform measurements to determine an amount the body is perspiring. In another example, the humidity and/or temperature sensors in the humidity and/or temperature sensor port 490 may perform a surface temperature measurement of the skin. In one example, a first humidity measurement and a first temperature measurement of an individual may be measured. A first vapor pressure measurement of the individual may be calculated from the first humidity measurement and the first temperature measurement. A second humidity measurement and a second temperature measurement of an individual may be measured. A second vapor pressure measurement of the individual may be calculated from the second humidity measurement and the second temperature measurement. The individual's sweat rate may be determined from the first vapor pressure measurement and the second vapor pressure measurement.

In one embodiment, the electronic device 400 includes one or more ports such as a humidity, airflow, and/or temperature sensor port 490. The humidity, airflow, and/or temperature sensors may perform measurements to determine an adjusted hydration condition. An airflow measurement may be determined from one or more measurements (e.g., first and second pressure measurements, first and second temperature measurements, and so forth) of the airflow sensor. An ambient temperature may be measured by an ambient temperature sensor. An ambient humidity may be measured by an ambient humidity sensor. A skin temperature may be measured by a temperature sensor. An adjusted baseline may be determined from the ambient temperature, the ambient humidity, and the airflow measurements. An adjusted hydration condition may be determined in view of the adjusted baseline, the skin temperature, and one or more physiological measurements.

In another embodiment, the electronic device 400 may also include a pulse oximeter to measure a user's blood oxygen level.

FIG. 4B illustrates a view of the bottom surface of an electronic device 400, according to one embodiment. The electronic device 400 may include a processing device 425 coupled to the sensors 420, 455, and sensors in port 490 to take selected measurements. The processing device 425 may receive measurement information from the one or more sensors 420, 455, and sensors in one or more ports such as port 490 and analyze the measurement information to determine selected information, such as a hydration condition, physiological information, medical information, and so forth. In one example, the selected information can be hydration condition information, cardiac information (e.g., blood pressure or heart rate), blood oxygen level information, skin luminosity information, or other user information.

The electronic device 400 may also include one or more indicators 435 used to alert the user of the electronic device 400 of a hydration condition change. The indicator 435 may be on the top or the bottom of the electronic device 400 based on a type of the indicator 435. For example, the indicator 435 can be a display or light may be on the top of the electronic device 400. In another example, the indicator 435 can be a vibrator on the bottom of the electronic device 410. The vibrator may be located with a distance from the sensors to avoid interference with the sensor measurements. In another example, the indicator 435 can be a speaker. The speaker may be located proximate the top wall and/or perimeter wall of the electronic device 400. The volume of the speaker may be higher if it is completely encapsulated. The volume of the speaker may be lower if located in a port with a membrane.

Figure 5:
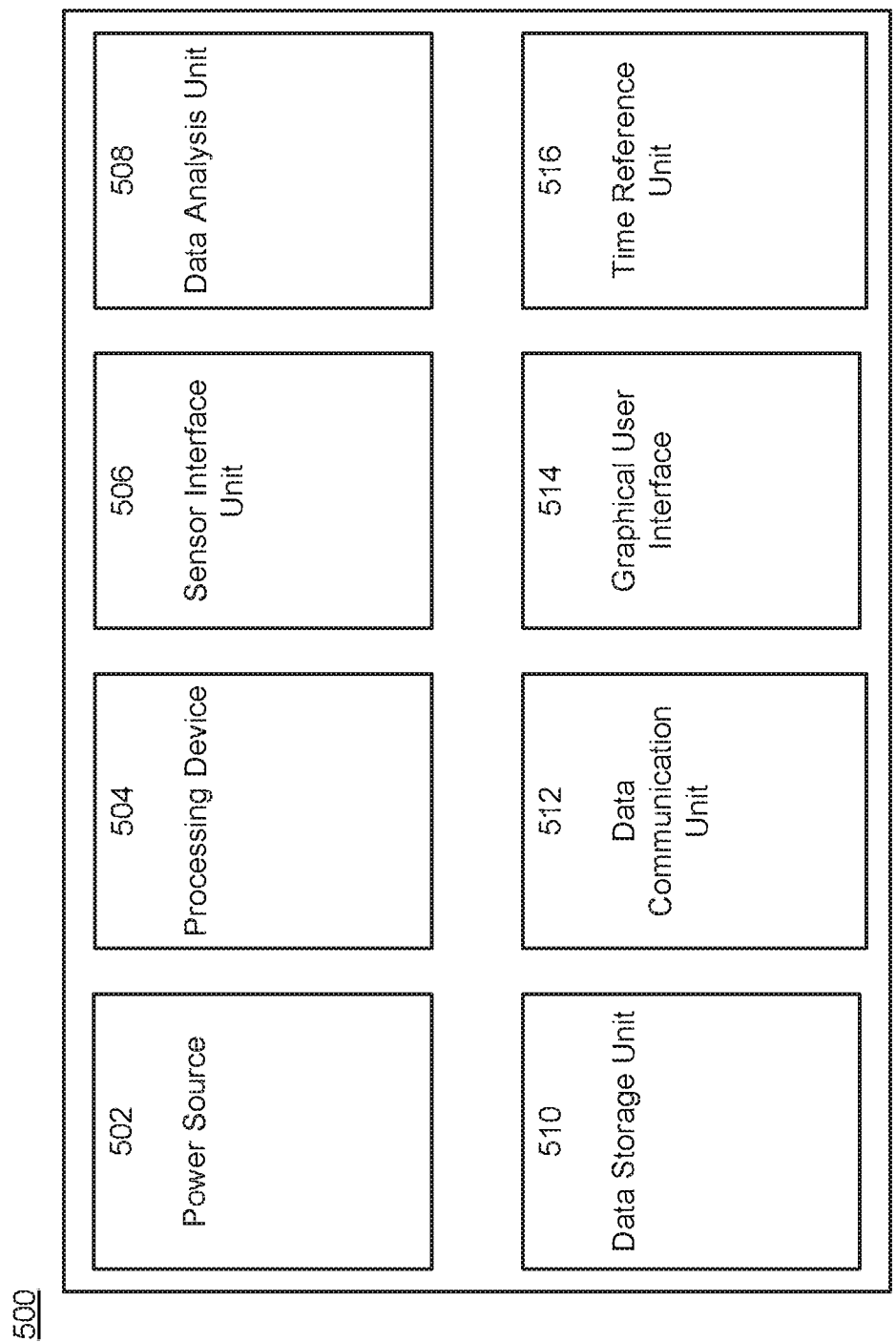
FIG. 5 illustrates a block diagram of an electronic device, according to one embodiment.

FIG. 5 illustrates a block diagram of an electronic device 500, according to one embodiment. The electronic device 500 may include a power source 502, a processing device 504, a sensor interface unit 506, a data analysis unit 508, a data storage unit 510, a data communication unit 512, a graphical user interface 514, and a time reference unit 516.

In one embodiment, the electronic device 500 includes a power unit 502 that supplies power to components of the electronic device 500. The power unit 502 may include a battery to supply power and a charging unit that charges the battery. Alternatively, electronic device 500 is connectable to an energy source that powers the electronic device 500. In one embodiment, a charger may be used to recharge a battery or other energy source of the power unit 502. In one embodiment, an external battery (e.g., located in the band, and so forth) is coupled to the power unit 502.

In one embodiment, the electronic device 500 includes a processing device 504. The processing device 504 may include a central processor to process the data and/or information of the other components that include the electronic device 500 or other units, interfaces, and/or devices attached to or in communication with the electronic device 500.

In another embodiment, the electronic device 500 may include a sensor interface unit 506. The sensor interface unit 506 may be coupled to one or more sensors, such as the optical sensor, the impedance sensor, or the humidity and/or temperature sensors, and may perform one or more measurements relating to a physiological condition of a body using one or more of the sensors. In one embodiment, the sensor interface 506 and the processing device 504 may be the same component. In another embodiment, the sensor interface 506 may be coupled to the processing device 504. The sensor interface 506 can use the one or more sensors to take measurements relating to a hydration condition of a body, an impedance measurement, a backscatter measurement, a temperature measurement of a body or of an environment, a humidity measurement of a body or of an environment, an airflow measurement (e.g., temperature measurements, pressure measurements, and so forth) of the environment, or another physiological state or environment condition measurement. In one example, the sensor interface 506 may be coupled to the processing device 504 and the ambient humidity, airflow, skin temperature, and/or ambient temperature sensors. In this example, the sensor interface 506 may receive data from the ambient humidity, airflow, skin temperature, and/or ambient temperature sensors relating to the ambient humidity, airflow, skin temperature, and ambient temperature at the location of the electronic device 500. In one example, the sensor interface 506 may be communicatively coupled to the processing device 504 and the optical sensor. In this example, the sensor interface unit 506 may receive data from the optical sensor relating to a portion of light that was reflected off an artery or other muscular-walled tube. Alternatively, the sensor interface 506 and the processing device 504 may be the same component. The sensor interface unit 506 may measure the backscatter of one or more wavelengths that have been reflected off a vein, artery, or other muscular-walled tube using the portion of light. In one example, the sensor interface 506 may be communicatively coupled to the processing device 504 and the impedance sensor. In this example, the sensor interface 506 may receive data from the impedance sensor relating to detection portion of an electric current. In one example, the sensor interface 506 may be communicatively coupled to the processing device 504 and a first humidity sensor, a second humidity sensor, a first temperature sensor, and a second temperature sensor. In this example, the sensor interface 506 may receive data from the humidity and temperature sensors relating to the humidity and temperature of the user at the location of the electronic device 500.

In another embodiment, the electronic device 500 may include a time reference unit 516 that generates time reference data usable to control the time at which data is collected from the sensor interface unit 506. The time reference unit 516 may also be used to calculate spatial and/or temporal derivatives between information received from the sensor interface unit 506. In one embodiment of the disclosure, the time reference unit 516 may keep track of the calendar time, such as a clock. Alternatively, the time reference unit 516 may act as a timer, keeping track of a lapsed time or decrementing from a defined time to zero. The timer of the time reference unit 516 may be used to collect information or data from the sensor interface 506 for a defined period of time or to record how long the sensor interface 506 collects data.

In another embodiment, the electronic device 500 includes a data analysis unit 508. The data analysis unit 508 may be communicatively coupled to the processing device 504, sensor interface unit 506, time reference unit 516, and other components of the electronic device 500. The data analysis unit 508 may determine that a hydration condition has changed for a user by comparing temporal data from the time reference unit 516 to measurement data from the sensor interface unit 506. The data analysis unit 508 may communicate the hydration condition to a user through the graphical user interface (GUI) 514.

In another embodiment, the electronic device 500 includes a GUI 514. The graphical user interface may be a monitor screen, liquid crystal display (LCD), light emitting diode (LED) display, or the like. In embodiment, the GUI may present information such as a hydration condition to the user. In another embodiment, the user may be able to interact with the electronic device though inputs or icons on the GUI.

Figure 6:
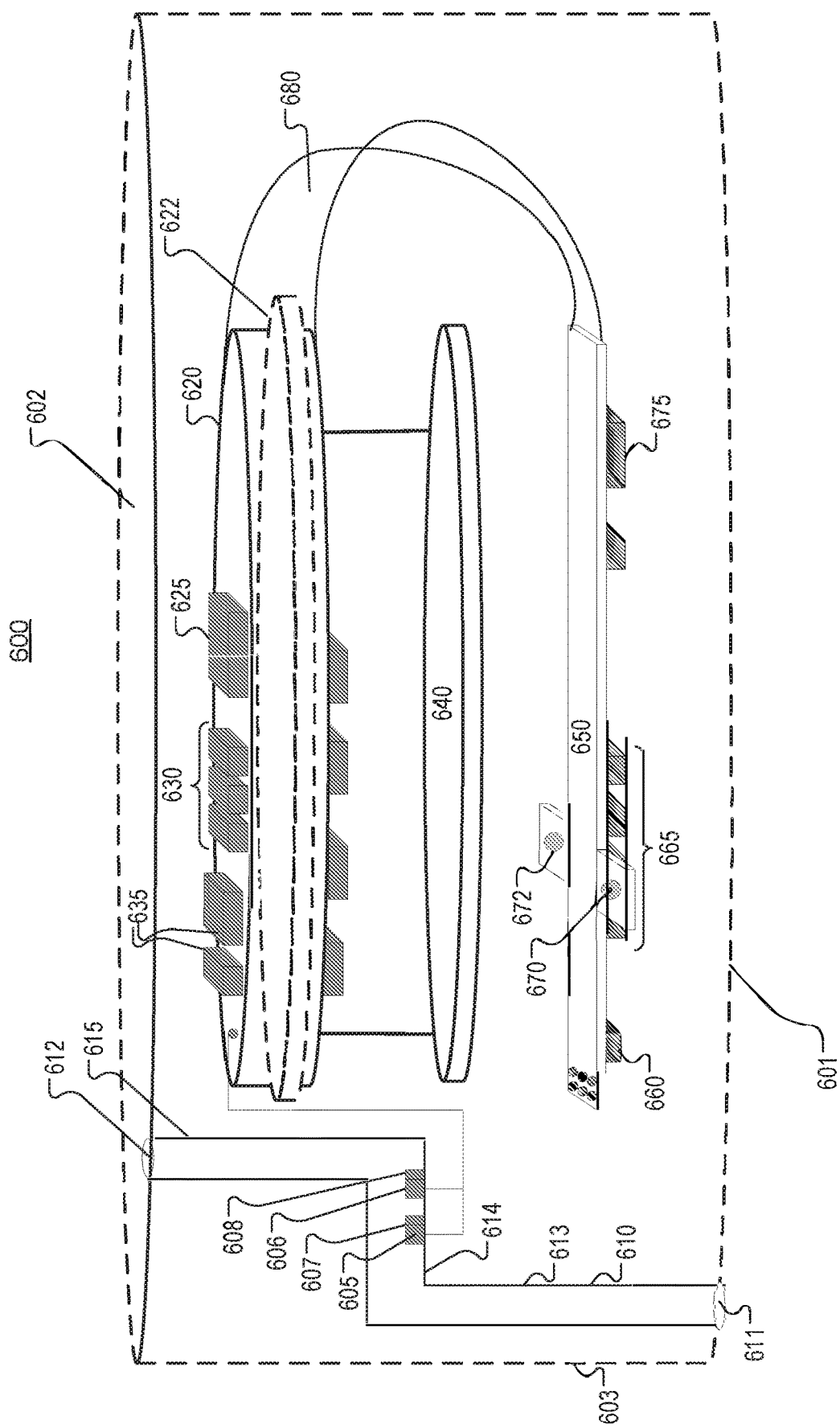
FIG. 6 illustrates an interior view of an electronic device, according to one embodiment.

FIG. 6 illustrates an interior view of an electronic device 600, according to one embodiment. The electronic device 600 may be in the form of a cylinder, a polyhedron, a tetrahedron, a hexahedron (e.g., cube, parallelepiped, rectangular prism, and so forth), an octagonal prism, an ellipsoid, or some other shape. The electronic device 600 may include a bottom wall 601, a top wall 602, and a perimeter wall 603. A wall (e.g., bottom wall 601, top wall 602, perimeter wall 603, and so forth) of the housing may be a barrier, a layer, a composite, an area, and so forth. The perimeter wall 603 may be disposed around a perimeter of the electronic device 600 between the top wall 602 and the bottom wall 601. The top wall 602, the bottom wall 601, and the perimeter wall 603 may form an inner cavity. The exterior side of the bottom wall 601 may be shaped to affix to a user. For example, the exterior side of the bottom wall 601 may contact a body surface of the user. The top wall 602 may be opposite the exterior side of the bottom wall 601. In one example, the exterior side of the top wall 602 may face away from the body surface of the user and not directly contact the user when affixed to the user.

In one embodiment, the electronic device 600 may have a circuit board that includes a first portion 650, a second portion 670, a third portion 672, and a fourth portion 620. The circuit board may flip up or curl up adjacent to the flume 610 or perimeter wall 603 if it is too long to fit along the interior surface of the bottom wall 601. The first portion 650 can be a sensor board. The first portion 650 may be disposed adjacent the bottom wall 601. The second portion 670 can be a first contact wing 670. The third portion can be a second contact wing 672. The fourth portion 620 can be a main circuit board. The fourth portion may be located adjacent the top wall 602. In one embodiment, the sensor board 650 can be a flexible circuit board. In another embodiment, the main circuit board 620 can be a printed circuit board (PCB) on a substrate, such as a fiberglass or glass-reinforced plastic substrate with copper traces. The contact wings 670 and 672 may be a foldable or flexible. The sensor board 650 may be coupled to the main circuit board 620 by a flexible connector 680. One or more components may be coupled to the sensor board 650. The components can include a vibrator 660, contact wings 670 and 672 (e.g., impedance sensor contacts, and so forth), optical components 665 (e.g., optical sensor, first light source, second light source, and so forth), and a thermistor 675. In one embodiment, the vibrator 660 may be activated to inform the user when a hydration condition has changed or to provide additional information to the user. The main PCB 620 may have double sided mounting and may include a motion processing unit (MPU) 625, display light emitting diodes (LEDs) or graphical user interface (GUI) 630, one or more communication components 635, such as a personal area network component (e.g., BLUETOOTH® Low Energy (BLE) component, cellular antenna, and so forth), an induction coil 622, and so forth. The components on the flexible circuit board may be layered. In one embodiment, the MPU 625 may detect movement of the electronic device and relay motion information to the sensor interface unit 506 (FIG. 5). Additionally, the display LEDs or the GUI 630 may be used to inform the user of a hydration condition. The communication components 635 may be located on the main PCB 625 to reduce or eliminate interference.

In another embodiment, a conductive material (e.g., a piece of copper, and so forth) is attached to the circuit board. A first portion of the conductive material may be disposed in the inner cavity adjacent to the bottom wall 601. A second portion of the conductive material may go through an opening to the exterior surface of the bottom wall. A third portion of the conductive material may go through another opening in the external surface of the bottom wall.

The LEDs 630 may be located adjacent to the top wall 602. A portion of the top wall 602 may include a light diffusing material. The light diffusing material and LEDs 630 may provide backlighting. The processing device 504 (FIG. 5) may turn on the LEDs 630 in response to an activation event. The activation event may include tapping the top wall 602 to wake up the electronic device 600, raising the electronic device 600 (e.g., raising the electronic device 600 up to the face of the user, and so forth), tilting the electronic device 600 (e.g., tilting the electronic device 600 towards the eyes of the user, and so forth).

In one embodiment, the electronic device 600 may include a flume 610. The flume 610 may be different geometries. For example, the flume 610 may be an s-shape. For example, the flume 610 may include a first portion 613 extending from a first opening 611 at the bottom wall 601 along a first axis that is parallel to the perimeter wall 603 of the electronic device 600. The flume 610 can include a second portion 614 that is connected to a first portion 613. The second portion 614 extends along a second axis that is at a defined angle from the first axis. In one example, the defined angle is approximately 90 degrees. The second portion 614 can include humidity sensors 605 and 606 and temperature sensors 607 and 608. In one embodiment, the sensors 605, 606, 607, and 608 can be located on the second portion 614. An advantage of the sensors 605, 606, 607, and 608 being located at the second portion 614 may decrease the amount of outside influences on the measurements. The outside influences can include interference from a temperature, a humidity, or an airflow that is exterior to the device. In one example, the temperature, the humidity, or the airflow that is exterior to the device can be an outdoor temperature, humidity, or airflow. In another example, the temperature, the humidity, or the airflow that is exterior to the device can be an indoor temperature, humidity, or airflow that enters the flume 610 when the user is moving. The second portion 614 should be long enough to allow locating the humidity sensors 605 and 606 far enough apart to measure a change in humidity and to allow locating the temperature sensors 607 and 608 far enough apart to measure a change in temperature to then be able to measure a change in vapor pressure from the change in humidity and change in temperature. The sensitivity of the humidity sensors 605 and 606 may determine how far apart the sensors 605 and 606 need to be to be able to measure a difference in humidity. For example, the more sensitive the humidity sensors 605 and 606 are, the closer the humidity sensors 605 and 606 can be located and still measure a difference in humidity. The sensors should be close enough together to minimize the size of the flume and the electric device 600. The flume 610 may include a third portion 615 that is connected to the second portion 614. The third portion 615 extends along a third axis that is parallel to the first axis. The third portion 615 extends to a second opening 612 at the top wall 602. The flume may be insulated to avoid interference of the sensors inside the flume from heat from the electronics in the electronic device 600, environmental temperature, and so forth. The flume may reduce and/or remove condensation from the flume. In one embodiment, the flume may reduce condensation by insulating the flume from ambient temperature (e.g., insulate from cold outside temperature). In another embodiment, the flume may reduce condensation by heating a portion of the flume 610 proximate the second opening 612 (e.g., not insulating the portion of the flume 610 proximate the second opening 612 from heat from electronics inside the electronic device 600). In another embodiment, the flume may remove condensation by having a lining that wicks the condensation to the exterior of the electronic device 600. In another embodiment, the flume may remove condensation by a condensation pathway to the exterior of the electronic device 600. In another embodiment, the flume may remove condensation capturing and reheating the condensation so that it leaves the electronic device 600 as vapor.

In another embodiment, the flume 610 may be at least one of inclined or u-shaped. The flume may extend from a first opening 611 at the bottom wall 601 to a second opening 612 at the top wall 602. The flume 610 may extend from the bottom wall 601 to the top wall 602. A membrane may be disposed proximate the first opening 611 and/or the second opening 612 to filter fluid and dirt particles, as discussed in greater detail in the proceeding paragraphs.

The flume 610 may allow humidity and/or temperature sensors 605 to measure the humidity and/or temperature proximate the skin of the user. For example, heat is radiated from the skin of the user, the heat goes up the flume 610, temperature sensor 607 takes a first temperature measurement, and temperature sensor 608 takes a second temperature measurement. In another example, as sweat evaporates from the skin of a user, the air proximate the skin of the user will have a humidity level due to the sweat evaporating from the skin as vapor. The vapor will enter the flume 610 at the first opening 611 in the bottom wall 601, humidity sensor 605 will take a first humidity measurement and humidity sensor 606 will take a second humidity measurement, and the vapor can exit the second opening 612 in the top wall 602. Humidity sensor 605 and temperature sensor 607 may be a single sensor. Humidity sensor 606 and temperature sensor 608 may be a single sensor.

In one embodiment, the electronic device 600 may have an ambient humidity sensor integrated proximate the top wall 602. In one embodiment, the ambient humidity sensor is the same as the humidity sensor 605 or 606. In another embodiment, the ambient humidity sensor may measure an environmental humidity that is not caused by vapor from the sweat evaporating from the skin of the user. The electronic device 600 may have an airflow sensor integrated into the top wall 602 or perimeter wall 603 of the electronic device. In one embodiment, the airflow sensor may include a first heating element and a second heating element. In one embodiment, the airflow sensor may include a pressure sensor (e.g., a pitot tube, a venturi tube, venturi pump, manifold absolute pressure (MAP) sensor, and so forth). The electronic device 600 may have a skin temperature sensor (e.g., thermistor, thermocouple, and so forth) integrated into the bottom wall 601. In one embodiment the skin temperature sensor may be the temperature sensor 607 or 608. The electronic device 600 may have an ambient temperature sensor located proximate the top wall 602. The ambient temperature sensor may measure an environmental temperature that is not radiating from the body. The ambient humidity sensor, ambient temperature sensor, airflow sensor, and so forth may be located in one or more flumes, recesses, cavities, and so forth.

In one embodiment, one or more sensors (e.g., impedance sensors, optical sensor, humidity sensors, temperature sensors, ambient temperature sensor, ambient humidity sensor, airflow sensor, skin temperature sensor, and so forth) may be coupled to a sensor interface unit 506 (FIG. 5). The sensor interface unit 506 (FIG. 5) may make an ambient humidity measurement using an ambient humidity sensor, one or more measurements using an airflow sensor (e.g., first and second temperature measurements, first and second pressure measurements, and so forth), a skin temperature measurement using a skin temperature sensor, an ambient temperature measurement using an ambient temperature sensor, an impedance measurement using impedance sensors, a vapor measurement using a humidity sensor and temperature sensor, and/or an amount of a wavelength of light measurement using an optical sensor.

In one embodiment, the electronic device 600 may include an information interface to receive user information from an input device such as GUI 630, or an external device such as a smart phone, a computer, and so forth. The user information may include demographic or personal information of a user including one or more of: a height of the user, a weight of the user, a gender of the user, a past hydration condition, a past event, and so forth. The processing device 504 (FIG. 5) may be coupled to the sensor interface unit 506 (FIG. 5) and the information interface.

The electronic device 600 is adapted to affix to a surface of a body. The electronic device 600 may be integrated into a band (e.g., wristband, sweatband, compression sleeve, and so forth). In one embodiment, the band may have a fastener (e.g., a loop and hook fastener, a clasp and holes, a deployment buckle, a folding clasp, and so forth). The fastener may adapt a band to different sizes of wrists. In one embodiment, the band may be made of a material that stretches. The fastener or material may be adaptable to affix the electronic device 600 to a range of sizes of users and to adapt to different surfaces of a body within a pressure range. The pressure range may maintain sensor contact with the skin and reduce or eliminate movement of the electronic device 600.

The band may be coupled to the electronic device 600 by at least one of a snap ring in band coupling with an indentation in the electronic device 600, an overlapping ring portion of the band overlapping a portion of the top wall of the electronic device 600, magnetic connection, frictional fit (e.g., the band is sized to fit around the perimeter wall 603 with a pressure to prevent the electronic device 600 from slipping from the band, the band fits around the perimeter wall 603 and over a portion of the top wall 602 to prevent the electronic device from slipping, and so forth), connector arms, and so forth.

The band may maintain the electronic device 600 affixed to a surface of a body at a pressure range. The pressure range may be measured in pounds per square inch (psi) or Pascal (Pa). The pressure range may be at least one of a substantially constant pressure, a pressure where the electronic device 600 does not slip, a pressure where the electronic device 600 does not affect the measurements (e.g., does not increase the skin temperature, does not increase the sweat rate, does not alter fluid content at the location of the electronic device 600, does not cause movement of fluid, and so forth). The pressure range may assist the electronic device 600 maintain good contact with the skin surface to avoid discontinuity of measurements. The band may be coupled to a feedback sensor that will alert the user if the electronic device 600 is affixed to a surface of a body at a pressure range. The feedback sensor may be at least one of a strain gauge, a pressure sensor, and so forth. The feedback sensor may be adjustable based on at least one of manual adjustment, user input, an algorithm, and so forth. The band may be adjustable for different types of wrists (e.g., large, skinny, wide, flat, round, male, female, and so forth). There may be interchangeable bands for different sized wrists. The circumference of a body part (e.g., wrist, and so forth) of the user may increase or decrease over time (e.g., due to heat, due to being hydrated or dehydrated, due to swelling, and so forth). In one embodiment, the band may adjust due to the change in circumference in response to a measurement of the feedback sensor. In another embodiment, the band may be made of a material that stretches in response to an increase in circumference and constricts in response to a decrease in circumference.

In one embodiment, the band may be adapted to be cut to an accurate length. In another embodiment, the band may include an integrated battery inductively coupled to a battery management system disposed in the inner cavity of the cylindrical housing. In another embodiment, the band may include an integrated communication device inductively coupled to a communication system disposed in the inner cavity of the cylindrical housing. In another embodiment, the band may include an integrated sensor inductively coupled to a sensor interface disposed in the inner cavity of the cylindrical housing. In another embodiment, the integrated battery, integrated communication device, and/or integrated sensor disposed in the band may be coupled to the electronic device 600 by an electrical connection. In another embodiment, the band may include a voltage regulator.

The electronic device 600 may include hypo-allergenic material. In one embodiment, the bottom wall 601, top wall 602, and perimeter wall 603 may be made of hypo-allergenic material. The bottom wall 601, top wall 602, and perimeter wall 603 may have a durable wall thickness and material. The components of the electronic device may be fastened to the bottom wall 601, top wall 602, and/or perimeter wall 603 by melting plastic posts and/or locating screws to avoid antenna interference.

Figure 7A:
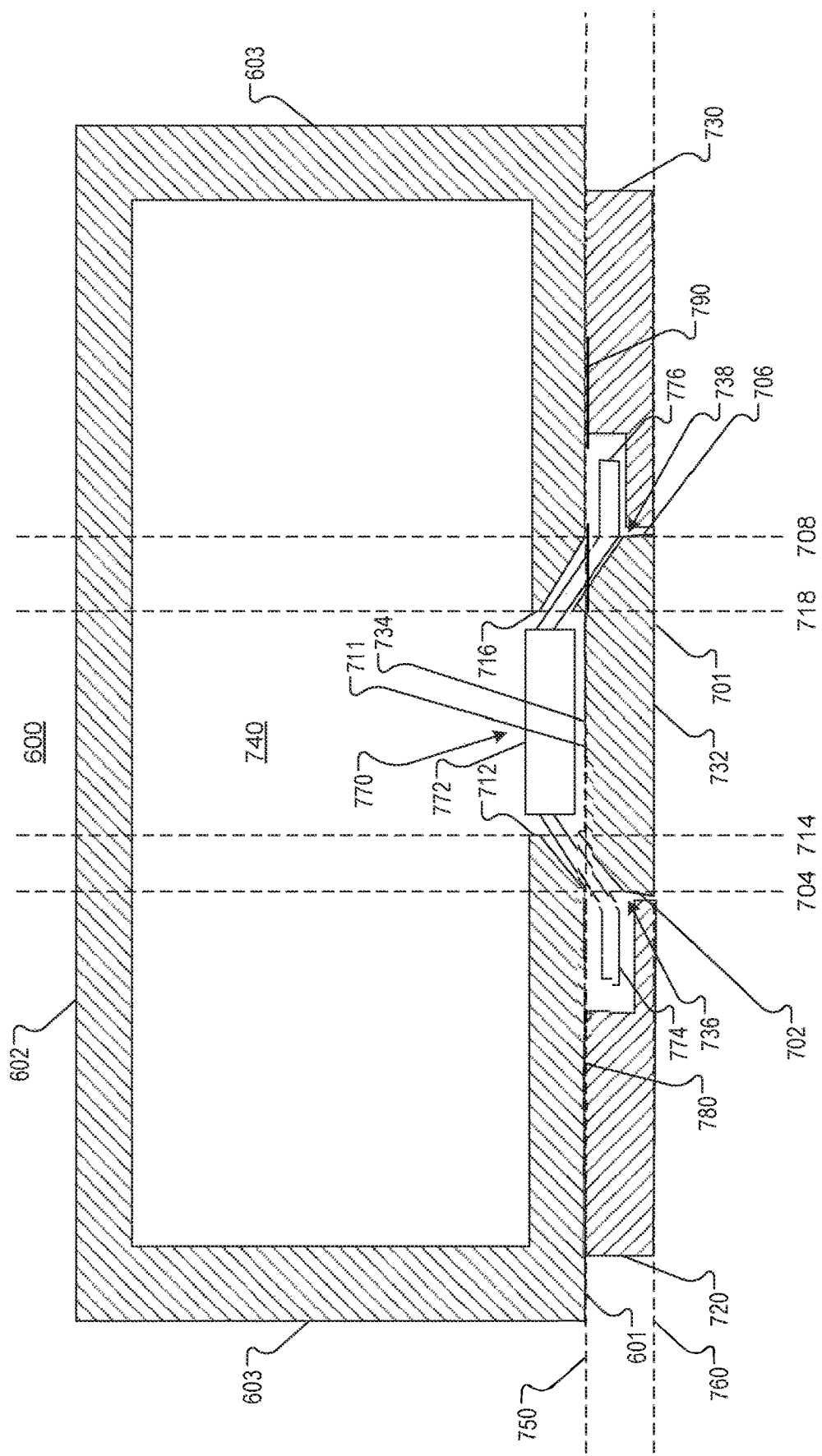
FIG. 7A illustrates a section view of an electronic device, according to one embodiment.

FIG. 7A illustrates a cross-sectional view of an electronic device 600, according to one embodiment. The electronic device 600 may include a housing with a bottom wall 601, a top wall 602, and a perimeter wall 603. A wall (e.g., bottom wall 601, top wall 602, perimeter wall 603, and so forth) of the housing may be a barrier, a layer, a composite, an area, and so forth. The perimeter wall 603 may be disposed around a perimeter of the electronic device 600 between the top wall 602 and the bottom wall 601. The top wall 602, the bottom wall 601, and the perimeter wall 603 may form an inner cavity 740.

The bottom wall 601 may be in a first plane 750. The bottom wall 601 may have a section that projects out from the first plane 750 to a second plane 760 to form a projection 732 on an external surface of the bottom wall 601 and a channel 734 in an internal surface of the bottom wall 601. The first plane 750 and the second plane 760 may be substantially parallel.

A first area 780 in the first plane 750 may be located on the external surface of the bottom wall 601 on a first side of the projection 732. A second area 790 in the first plane 750 may be located on the external surface of the bottom wall 601 on a second side of the projection 732. The first area 780 and the second area 790 may be substantially coplanar with plane 750. A substantial portion of the external surface of the bottom wall 601 may include the first area 780, the projection 732, and the second area 790.

The projection 732 may have a bottom wall surface 701 in the second plane 760, a first side wall surface 702 in third plane 704 and a second side wall surface 706 in a fourth plane 708. The third plane 704 and the fourth plane 708 may be substantially parallel. The third plane 704 and the fourth plane 708 may be substantially perpendicular to the first plane 750 and the second plane 760. The bottom wall surface 701 may adjoin the first side wall surface 702 at a 90-degree angle. The bottom wall surface 701 may adjoin the second side wall surface 706 at a 90-degree angle.

The channel 734 may have a bottom wall surface 711 in the first plane 750, a first side wall surface 712 in fifth plane 714 and a second side wall surface 716 in a sixth plane 718. The fifth plane 714 and the sixth plane 718 may be substantially parallel. The fifth plane 714 and the sixth plane 718 may be substantially parallel to the third plane 704 and the fourth plane 708. The fifth plane 714 and the sixth plane 718 may be substantially perpendicular to the first plane 750 and the second plane 760. The bottom wall surface 711 may adjoin the first side wall surface 712 at a 90-degree angle. The bottom wall surface 701 may adjoin the second side wall surface 716 at a 90-degree angle.

The electronic device 600 may include a first opening 736 from the first side wall surface 712 of the channel 734 to the first side wall surface 702 of the projection 732. The electronic device 600 may include a second opening 738 from the second side wall surface 716 of the channel 734 to the second side wall surface 706 of the projection 732.

A circuit board 770 may include a first portion 772 disposed in the channel 734 proximate the bottom surface 711, a second portion 77 that extends through the first opening 736, and a third portion 776 that extends through the second opening 738. In one embodiment, the first portion 772 can be a sensor board. In another embodiment, the second portion 774 can be a contact wing. In another embodiment, the third portion 776 can be a contact wing.

A first impedance pad 720 may be disposed on the second portion 774 in the first area 780. A second impedance pad 730 may be disposed on the third portion 776 in the second area 790. The first and second impedance pads 720 and 730 may at least one of be tinted, be made of a material, or have a protective coating to prevent corrosion. In one embodiment, the first impedance pad 720 and the second impedance pad 730 have a rectangular cross-sectional area. In another embodiment, the first impedance pad 720 and the second impedance pad 730 each have an indentation for the second portion 774 and the third portion 776 of the circuit board 770. The first impedance pad 720, the second impedance pad 730, and the bottom wall surface 701 of the projection 732 may be substantially coplanar in the second plane 760 to allow good contact of the pads with a skin surface of a user. The first impedance pad 720 may be operable to transmit an electric current into a body and the second impedance pad 730 may be operable to detect a portion of the electric current from the body at a depth below a surface of the body. The first impedance pad 720 may be located at the first area 780 of the bottom wall 601 and the second impedance pad may be located at the second area 790 of the bottom wall 601, where the first area 780 is at a fixed distance from the second area 790, to determine an impedance measurement between the first impedance pad 720 and the second impedance pad 730. An impedance measurement may be compared to one or more previous impedance measurements, a change may be determined in impedance level of the body using the impedance measurement, and a hydration condition of the body may be determined by comparing the change in impedance level from one or more impedance measurements.

FIG. 7B illustrates a cross-sectional view of an electronic device 600, according to another embodiment. The electronic device 600 may include a housing with a bottom wall 601, a top wall 602, and a perimeter wall 603. A wall (e.g., bottom wall 601, top wall 602, perimeter wall 603, and so forth) of the housing may be a barrier, a layer, a composite, an area, and so forth. The perimeter wall 603 may be disposed around a perimeter of the electronic device 600 between the top wall 602 and the bottom wall 601. The top wall 602, the bottom wall 601, and the perimeter wall 603 may form an inner cavity 740.

The bottom wall 601 may be in a first plane 750. The bottom wall 601 may have a section that projects out from the first plane 750 to a second plane 760 to form a projection 732 on an external surface of the bottom wall 601 and a channel 734 in an internal surface of the bottom wall 601. The first plane 750 and the second plane 760 may be substantially parallel.

A first recess 780 may be located on the external surface of the bottom wall 601 on a first side of the projection 732. A second recess 790 may be located on the external surface of the bottom wall 601 on a second side of the projection 732. A first lip 792 and the projection 732 may surround the first recess 780. A second lip 794 in plane 760 and the projection 732 may surround the second recess 790. The first lip 792, the second lip 794, and the projection 732 may be substantially coplanar with plane 760. In one embodiment, the first lip 792 and the second lip 794 may be substantially the same thickness as the perimeter wall 603.

The first recess 780 may be formed by the external surface of the bottom wall 601 on a first side of the projection 732 between the first plane 750 and second plane 760 and the external surface of the bottom wall 601 in the first plane 750. The second recess 790 may be formed by the external surface of the bottom wall 601 on a second side of the projection 732 between the first plane 750 and second plane 760 and the external surface of the bottom wall 601 in the first plane 750.

The projection 732 may have a bottom wall surface 701 in the second plane 760, a first side wall surface 702 in third plane 704 and a second side wall surface 706 in a fourth plane 708. The third plane 704 and the fourth plane 708 may be substantially parallel. The third plane 704 and the fourth plane 708 may be substantially perpendicular to the first plane 750 and the second plane 760. The bottom wall surface 701 may adjoin the first side wall surface 702 at a 90-degree angle. The bottom wall surface 701 may adjoin the second side wall surface 706 at a 90-degree angle.

The channel 734 may have a bottom wall surface 711 in the first plane 750, a first side wall surface 712 in fifth plane 714 and a second side wall surface 716 in a sixth plane 718. The fifth plane 714 and the sixth plane 718 may be substantially parallel. The fifth plane 714 and the sixth plane 718 may be substantially parallel to the third plane 704 and the fourth plane 708. The fifth plane 714 and the sixth plane 718 may be substantially perpendicular to the first plane 750 and the second plane 760. The bottom wall surface 711 may adjoin the first side wall surface 712 at a 90-degree angle. The bottom wall surface 701 may adjoin the second side wall surface 716 at a 90-degree angle.

The electronic device 600 may include a first opening 736 from the first side wall surface 712 of the channel 734 to the first side wall surface 702 of the projection 732. The electronic device 600 may include a second opening 738 from the second side wall surface 716 of the channel 734 to the second side wall surface 706 of the projection 732.

A circuit board 770 may include a first portion 772 disposed in the channel 734 proximate the bottom surface 711, a second portion 77 that extends through the first opening 736, and a third portion 776 that extends through the second opening 738. In one embodiment, the first portion 772 can be a sensor board. In another embodiment, the second portion 774 can be a contact wing. In another embodiment, the third portion 776 can be a contact wing.

A first impedance pad 720 may be disposed on the second portion 774 in the first recess 780. A second impedance pad 730 may be disposed on the third portion 776 in the second recess 790. In one embodiment, the first impedance pad 720 and the second impedance pad 730 have a rectangular cross-sectional area. In another embodiment, the first impedance pad 720 and the second impedance pad 730 each have an indentation for the second portion 774 and the third portion 776 of the circuit board 770. The first impedance pad 720, the second impedance pad 730, the first lip 792, the second lip 794, and the bottom wall surface 701 of the projection 732 may be substantially coplanar in the second plane 760. The first impedance pad 720 may be operable to transmit an electric current into a body and the second impedance pad 730 may be operable to detect a portion of the electric current from the body at a depth below a surface of the body. The first impedance pad 720 may be located at the first area 780 of the bottom wall 601 and the second impedance pad may be located at the second area 790 of the bottom wall 601, where the first area 780 is at a fixed distance from the second area 790, to determine an impedance measurement between the first impedance pad 720 and the second impedance pad 730. An impedance measurement may be compared to one or more previous impedance measurements, a change may be determined in impedance level of the body using the impedance measurement, and a hydration condition of the body may be determined by comparing the change in impedance level from one or more impedance measurements.

Figure 8A:
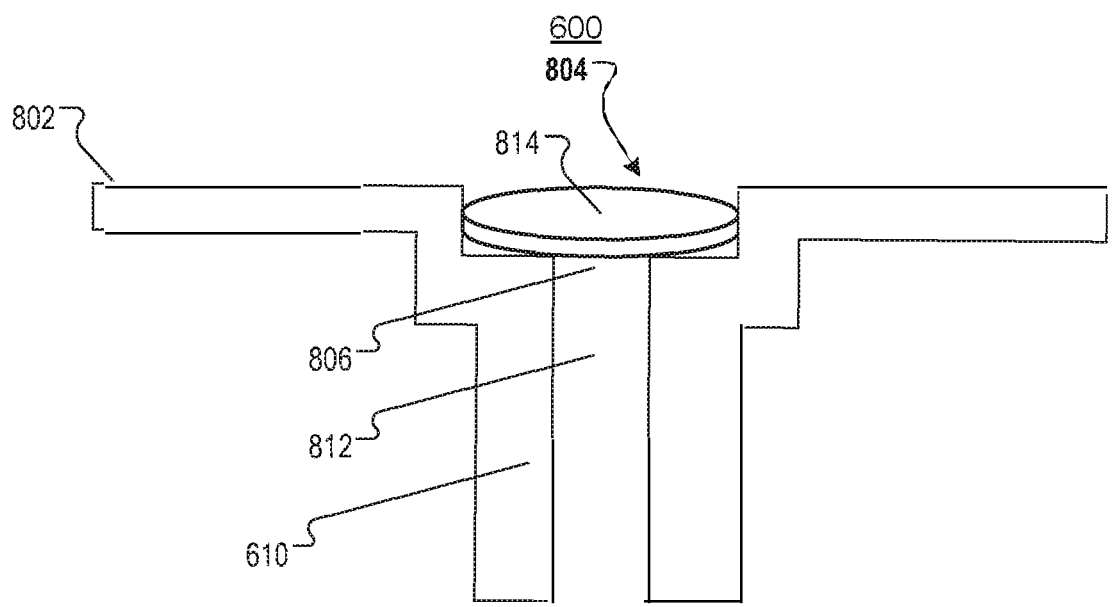
FIG. 8A illustrates a cross-sectional view of a flume of an electronic device, according to one embodiment.

FIG. 8A illustrates a cross-sectional view of a flume 610 of an electronic device 600 (FIG. 6), according to one embodiment. Some components of the electronic device 600 of FIG. 8A are similar to some components of the electronic device 600 of FIG. 6 as noted by similar reference numbers unless expressly described otherwise. The electronic device 600 (FIG. 6) may include a recess 804 in a wall 802 (e.g., perimeter wall 603, top wall 602, bottom wall 601, and so forth). The recess 804 may have an opening 806 (e.g., first opening 611, second opening 612, and so forth). In one embodiment, the electronic device 600 (FIG. 6) may have a flume 610 (FIG. 6) with a first end 812 disposed proximate the opening 806. The opening 806 may have a smaller cross-sectional area than the recess 804. The opening 806 may have substantially the same cross-sectional area as the flume 610 (FIG. 6). A membrane 814 may be disposed in the recess 804 in the wall 802 at the first end 812 of the flume 610 (FIG. 6). The membrane may include one or more materials including a semipermeable membrane, GORE-TEX®, hydrophobic filter material, expanded polytetrafluoroethylene (ePTFE), and so forth. The membrane 814 may be substantially coplanar with the external surface of the wall 802. The membrane 814 may have pores that are smaller than liquid droplets (e.g., water, sweat, and so forth) and solid particles (e.g., dirt, sand, and so forth) to prevent fluid and solid particles from entering the flume 610 (FIG. 6). In one embodiment, the membrane 814 may have nine billion pores per square inch, each pore being 20,000 times smaller than a water droplet, but large enough to allow vapor to pass through. The membrane 814 may allow at least one of vapor, airflow, and heat to exit the flume 610 (FIG. 6). The membrane 814 may allow at least one of vapor, airflow, and heat to enter the flume 610 (FIG. 6). The membrane may allow vapor and air to pass through to the flume 610 (FIG. 6) so that humidity and temperature measurements can be taken by the humidity sensors 605 and 606 and temperature sensors 607 and 608 (FIG. 6) to calculate vapor pressure measurements.

In one embodiment, the electronic device 600 (FIG. 6) may be substantially waterproof, water resistant, hermetically sealed, or in some other way protect the components from moisture damage. In one embodiment, each flume 610 of the electronic device 600 (FIG. 6) may include a membrane 814 to hermetically seal the flume 610 so that fluid cannot enter the housing 410. The electronic device 600 (FIG. 6) may be hermetically sealed, having no physical external ports that are not hermetically sealed. In one embodiment, one or more components of the electronic device 600 (FIG. 6) may have a component coating (e.g., nano-film, and so forth). In one embodiment, sealing structures (e.g., gaskets, a-rings, rubber seals, molded shapes, custom sealing devices, and so forth) and/or other components (e.g., epoxy, and so forth) may be used to seal openings into the electronic device 600 (FIG. 6). In one embodiment, the electronic device 600 (FIG. 6) does not have external data ports. The flexible circuit board may be flashed with wireless area network protocol (e.g., BLE protocol, and so forth) before sealing the electronic device 600 (FIG. 6) so that the electronic device will not require the external data ports. The flexible circuit board may include an interface to receive firmware updates (e.g., flash firmware updates, and so forth).

Figure 8B:
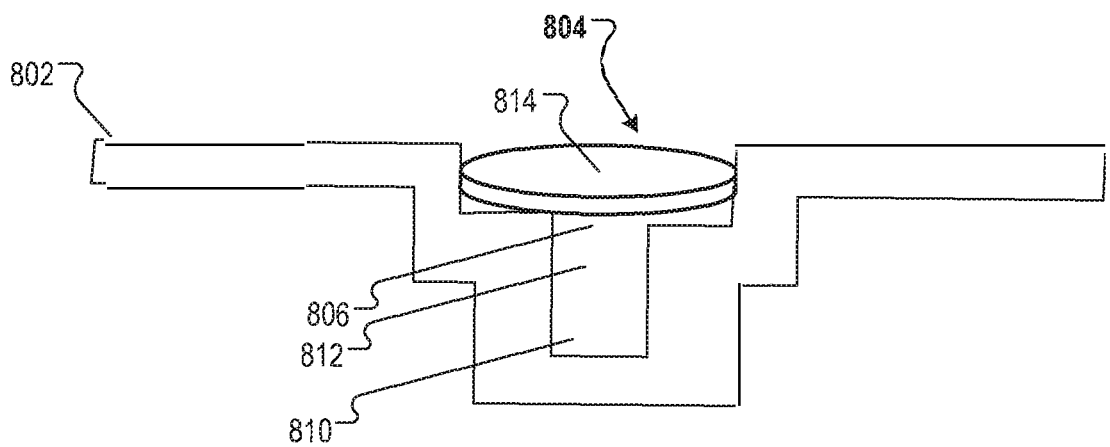
FIG. 8B illustrates a cross-sectional view of a cavity of an electronic device, according to one embodiment.

FIG. 8B illustrates a cross-sectional view of a cavity 810 of an electronic device 600, according to one embodiment. Some components of the electronic device 600 of FIG. 8B are similar to some components of the electronic device 600 of FIG. 8A as noted by similar reference numbers unless expressly described otherwise. The electronic device 600 (FIG. 6) may include a recess 804 in a wall 802 (e.g., perimeter wall 603, top wall 602, bottom wall 601, and so forth). The recess 804 may have an opening 806. In one embodiment, the electronic device 600 (FIG. 6) may have a cavity 810 with a first end 812 disposed proximate the opening 806. The opening 806 may have a smaller cross-sectional area than the recess 804. The opening 806 may have substantially the same cross-sectional area as the cavity 810. A membrane 814 may be disposed in the recess 804 in the wall 802 at the first end 812 of the cavity 810. A sensor (e.g., ambient temperature sensor, ambient humidity sensor, airflow sensor, skin temperature sensor, and so forth) may be disposed in the cavity 810. In one embodiment the membrane 814 may have small pores (e.g., nine billion pores per square inch or a different amount of pores) that reduce or prevent airflow from entering the cavity 810. In another embodiment, the membrane 814 may have larger pores that allow airflow to enter the cavity 810.

Figure 8C:
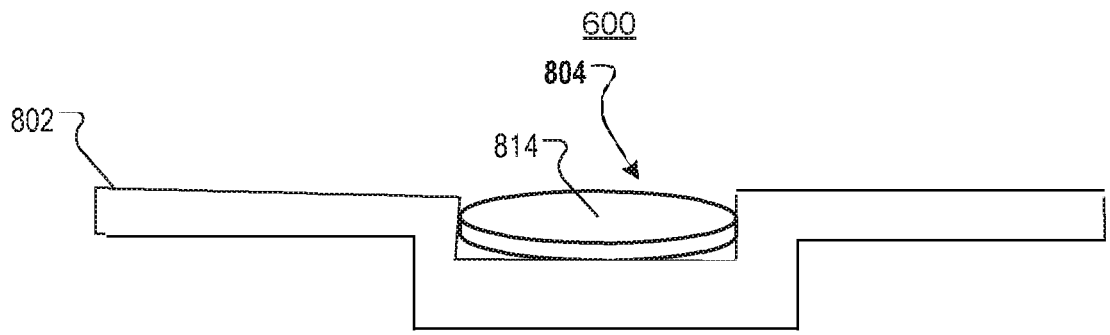
FIG. 8C illustrates a cross-sectional view of a recess of an electronic device, according to one embodiment.

FIG. 8C illustrates a cross-sectional view of a recess 804 in a wall 802 of an electronic device 600 (FIG. 6), according to one embodiment. Some components of the electronic device 600 of FIG. 8C are similar to some components of the electronic device 600 of FIG. 8A as noted by similar reference numbers unless expressly described otherwise. The electronic device 600 (FIG. 6) may include a recess 804 in a wall 802 (e.g., perimeter wall 603, top wall 602, bottom wall 601, and so forth). A membrane 814 may be disposed in the recess 804 in the wall 802. A sensor (e.g., ambient temperature sensor, ambient humidity sensor, airflow sensor, skin temperature sensor, and so forth) may be disposed in the recess 804, between the membrane 814 and the recess 804.

Figure 8D:
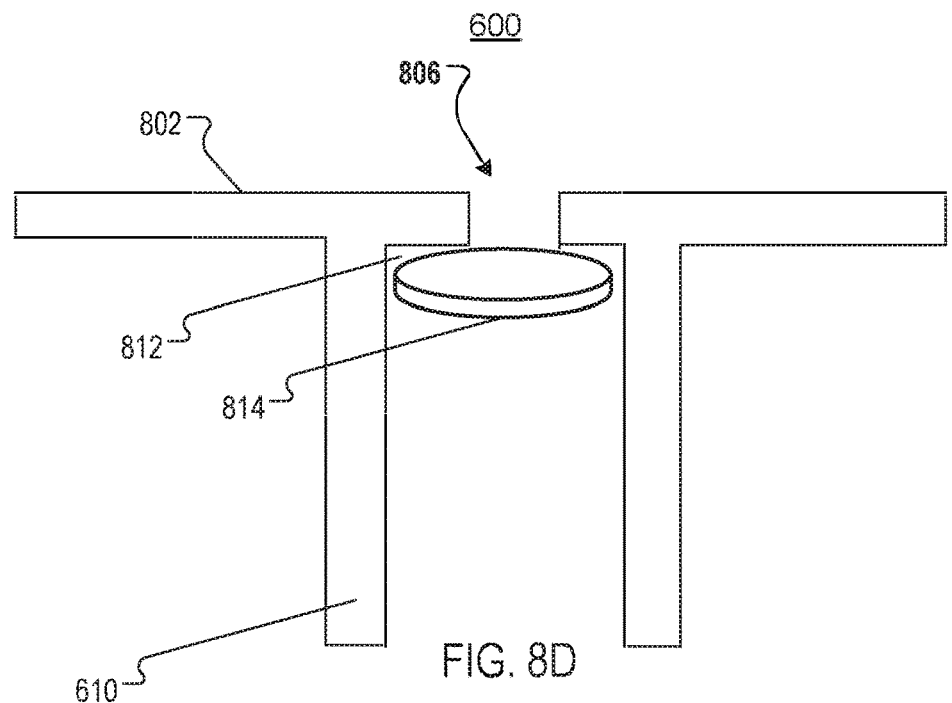
FIG. 8D illustrates a cross-sectional view of a flume of an electronic device, according to one embodiment.

FIG. 8D illustrates a cross-sectional view of a flume 610 of an electronic device 600 (FIG. 6), according to one embodiment. Some components of the electronic device 600 of FIG. 8D are similar to some components of the electronic device 600 of FIG. 8A as noted by similar reference numbers unless expressly described otherwise. The electronic device 600 (FIG. 6) may include an opening 806 (e.g., first opening 611, second opening 612, and so forth). In one embodiment, the electronic device 600 (FIG. 6) may have a flume 610 (FIG. 6) with a first end 812 disposed proximate the opening 806. The opening 806 may have a smaller cross-sectional area than the cross-sectional area of the flume 610 (FIG. 6). A membrane 814 may be disposed in the flume 610 proximate the opening 806 in the wall 802 at the first end 812 of the flume 610 (FIG. 6). Sensors may be disposed inside the flume 610 (FIG. 6) as described above.

Figure 8E:
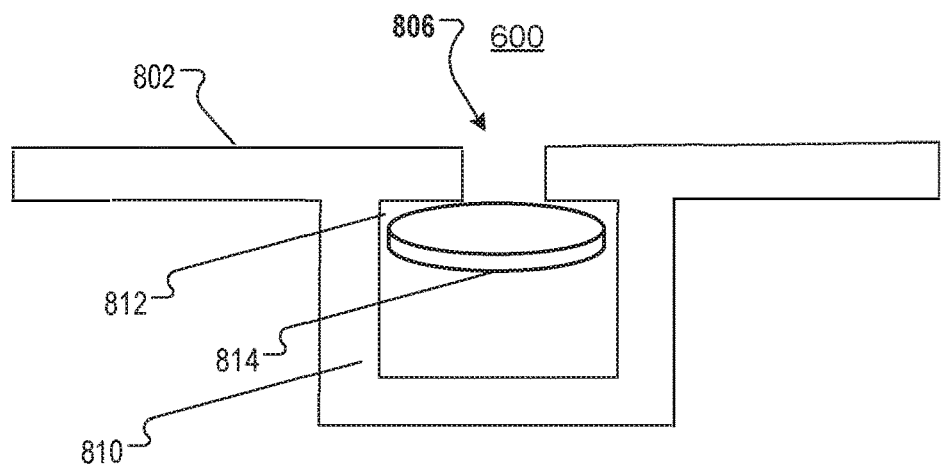
FIG. 8E illustrates a cross-sectional view of a cavity of an electronic device, according to one embodiment.

FIG. 8E illustrates a cross-sectional view of a cavity 810 of an electronic device 600 (FIG. 6), according to one embodiment. Some components of the electronic device 600 of FIG. 8E are similar to some components of the electronic device 600 of FIG. 8B as noted by similar reference numbers unless expressly described otherwise. The electronic device 600 (FIG. 6) may include a recess 804 in a wall 802 (e.g., perimeter wall 603, top wall 602, bottom wall 601, and so forth). The wall 802 may have an opening 806. In one embodiment, the electronic device 600 (FIG. 6) may have a cavity 810 with a first end 812 disposed proximate the opening 806. The opening 806 may have a smaller cross-sectional area than the cross-sectional area of the cavity 810. A membrane 814 may be disposed in the recess 804 in the wall 802 at the first end 812 of the cavity 810. One or more sensors may be disposed inside the cavity 810 as described above.

Figure 8F:
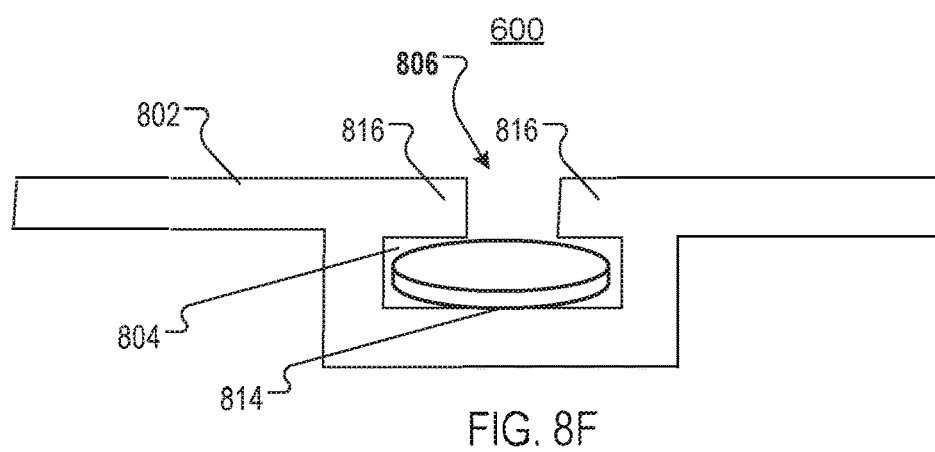
FIG. 8F illustrates a cross-sectional view of a recess of an electronic device, according to one embodiment.

FIG. 8F illustrates a cross-sectional view of a recess 804 in a wall 802 of an electronic device 600 (FIG. 6), according to one embodiment. Some components of the electronic device 600 of FIG. 8F are similar to some components of the electronic device 600 of FIG. 8C as noted by similar reference numbers unless expressly described otherwise. The electronic device 600 (FIG. 6) may include an opening 806 in a wall 802 (e.g., perimeter wall 603, top wall 602, bottom wall 601, and so forth). The electronic device 600 (FIG. 6) may include a recess 804 in the wall 602. The recess 804 may have a larger cross-sectional area than the cross-sectional area of the opening 806 creating a lip 816. A membrane 814 may be disposed in the recess 804 between the recess 804 and the lip 816.

FIG. 9A illustrates a top view of an electronic device 900, according to one embodiment. The electronic device 900 may have a top wall 902 that includes a display 910 on the exterior surface of the top wall 902. The top wall 902 may have a perimeter 904. The display 910 may provide relevant information to a user such as indicating battery level of the electronic device 902, indicating the user's hydration condition, and so forth. For example, the display 910 may signal when the electronic device 900 determines that the user is becoming dehydrated or is running the risk of becoming dehydrated. The electronic device 900 may include one or more ports such as a humidity, airflow, and/or temperature sensor port 930 on the top wall 902.

FIG. 9B illustrates a side view of an electronic device 900, according to one embodiment. Some components of the electronic device 900 of FIG. 9B are similar to some components of the electronic device 900 of FIG. 9A as noted by similar reference numbers unless expressly described otherwise. The electronic device 900 may include a bottom wall 901, a top wall 902, and a perimeter wall 903. The perimeter wall 903 may be disposed around a perimeter 904 of the electronic device 900 between the top wall 902 and the bottom wall 901. The top wall 902, bottom wall 901, and perimeter wall 903 may form an inner cavity. The bottom side 901 may be shaped to affix to a user. The second side 902 may be opposite the first side 901 and the second side 902 may not contact the user. The perimeter wall 903 may include an indentation 990 to affix a band, a sleeve, a clip, or other accessory to the electronic device 900.

FIG. 9C illustrates a perspective view of an electronic device 900, according to one embodiment. Some components of the electronic device 900 of FIG. 9C are similar to some components of the electronic device 900 of FIG. 9A as noted by similar reference numbers unless expressly described otherwise. The electronic device 900 may include a bottom wall 901, a top wall 902, and a perimeter wall 903. The perimeter wall may be disposed around a perimeter 904 of the electronic device 900 between the top wall 902 and the bottom wall 901. The top wall 902, bottom wall 901, and perimeter wall 903 may form an inner cavity. The top wall 902 may include a display 910 on the exterior surface of the top wall 902. The electronic device 900 may include one or more ports such as a humidity, airflow, and/or temperature sensor port 930 on the top wall 902.

FIG. 9D illustrates a perspective view of an electronic device 900, according to one embodiment. Some components of the electronic device 900 of FIG. 9D are similar to some components of the electronic device 900 of FIG. 9A as noted by similar reference numbers unless expressly described otherwise. The electronic device 900 may include a bottom wall 901, a top wall 902, and a perimeter wall 903. The perimeter wall may be disposed around a perimeter 904 of the electronic device 900 between the top wall 902 and the bottom wall 901. The top wall 902, bottom wall 901, and perimeter wall 903 may form an inner cavity. The bottom wall 901 may include a section that projects out from a first plane to a second plane to form a projection 915 on an external surface of the bottom wall 901. The bottom wall 901 may form a first recess 918 on a first side of the projection 915 between a first and second planes and the external surface of the bottom wall 915 in the first plane. The bottom wall 901 may form a second recess 919 on a second side of the projection 915 between the first and second planes and the external surface of the bottom wall 901 in the first plane. In one embodiment, impedance pad 950 may be disposed in first recess 918 and impedance pad 960 may be disposed in second recess 919. Impedance pad 950, impedance pad 960, and projection 915 may be substantially coplanar in the second plane. In one embodiment, one or more of a thermistor 975, an optical sensor 920, a first light source 930, a second light source 940, or a vibrator 960 may be located in or disposed proximate the bottom wall 901.

FIG. 10A illustrates a top perspective view of an electronic device 1000, according to one embodiment. The electronic device 1000 may include a top wall 1002. The electronic device 1000 may be coupled to a band 1092. In one embodiment, the band 1092 may stretch to be positioned around the electronic device 1000. In one embodiment, the band 1092 may be removed from and reattached (e.g., removably attachable) to an electronic device 1000. In one embodiment, the band 1092 may be formed around the electronic device 1000. In one embodiment, the band 1092 may be affixed to the electronic device 1000. In one embodiment, a portion of the band 1092 may only cover the perimeter wall 903 of the electronic device 1000. In another embodiment, a portion of the band 1092 may cover the entire electronic device 1000 except for the display. In another embodiment, a portion of the band 1092 may cover a portion of the top wall 1002 of the electronic device 1000.

The portion of the band 1092 that covers a portion of the top wall 1002 may hold the electronic device 1000 in place and allow the user to see the display.

FIG. 10B illustrates a top view of an electronic device 1000, according to one embodiment. The electronic device 1000 may include a top wall 1002. The electronic device 1000 may be coupled to a band 1092. In one embodiment, the band 1092 may stretch to be positioned around the electronic device 1000. In one embodiment, the band 1092 may be removed from and reattached (e.g., removably attachable) to an electronic device 1000. In one embodiment, the band 1092 may be formed around the electronic device 1000. In one embodiment, the band 1092 may be affixed to the electronic device 1000. A portion of the band 1092 may cover a portion of the top wall 1002 of the electronic device 1000. In one embodiment, a portion of the band 1092 may form a frictional fit (e.g., apply pressure) around a perimeter wall 1003 of the electronic device 1000. In another embodiment, a portion of the band 1092 may be disposed proximate the perimeter wall 1003 of the electronic device 1000.

FIG. 10C illustrates a side view of an electronic device 1000, according to one embodiment. The electronic device 1000 may include a bottom wall 1001, a top wall 1002, and a perimeter wall 1003. The electronic device 1000 may be coupled to a band 1092. In one embodiment, the band 1092 may stretch to be positioned around the electronic device 1000. In one embodiment, the band 1092 may be removed from and reattached (e.g., removably attachable, and so forth) to an electronic device 1000. In one embodiment, the band 1092 may be formed around the electronic device 1000. In one embodiment, the band 1092 may be affixed to the electronic device 1000. A portion of the band 1092 may cover a portion of the top wall 1002 of the electronic device 1000. A portion of the band 1092 may be disposed adjacent to the perimeter wall 1003 of the electronic device 1000. In one embodiment, a portion of the band 1092 may cover a portion of the electronic device 1000 to hold the electronic device in place. In another embodiment, the band 1092 may not cover any portion of the bottom of the electronic device 1000. The band 1092 may be held in place by friction (e.g., pressure exerted by the band 1092 on the electronic device 1000). In another embodiment, the band 1092 covers a portion of the bottom wall 1001 of the electronic device but does not cover any sensors on the bottom wall 1001 of the device.

FIG. 10D illustrates a bottom perspective view of an electronic device 1000, according to one embodiment. The electronic device 1000 may include a bottom wall 1001. The electronic device 1000 may be coupled to a band 1092. In one embodiment, the band 1092 may stretch to be positioned around the electronic device 1000. In one embodiment, the band 1092 may be removed from and reattached (e.g., removably attachable) to an electronic device 1000. In one embodiment, the band 1092 may be formed around the electronic device 1000. In one embodiment, the band 1092 may be affixed to the electronic device 1000. A portion of the band 1092 may cover a portion of the bottom wall 1001 of the electronic device 1000. The band 1092 may have openings to be positioned adjacent to the components in the bottom wall 1001. The electronic device 1000 may be integrated into the band 1092. In one embodiment, the band 1092 may be affixed to the electronic device. The electronic device may not be removably attachable to the band 1092. The sensors are not covered by the band 1092 when the electronic device 1092 is integrated into the band 1092. For example, the band 1092 may have openings or windows for the optical components. For another example, the band 1092 may have openings for the impedance pads. In one embodiment, one or more of a thermistor 1075, an optical sensor 1020, a first light source 1030, a second light source 1040, or a vibrator 1060 may be located in or disposed proximate the bottom wall 1001. In another embodiment, a third light source 1042 and a fourth light source 1044 may be located in the bottom wall 1001. The first light source 1030 and second light source 1040 may be equidistant from the optical sensor 1020. The third light source 1042 and fourth light source 1044 may be equidistant from the optical sensor 1020.

FIG. 11A illustrates a side view of an electronic device 1100, according to one embodiment. The electronic device 1100 may include a bottom wall 1101, a top wall 1102, and a perimeter wall 1103. The perimeter wall 1103 may have an indentation 1190. In one embodiment, the indentation 1190 may include a full cylindrical indentation that goes completely around the electronic device 1100. In another embodiment, the indentation 1190 may not completely surround the electronic device 1100 (e.g., the indentation 1190 may be intermittent around the electronic device so that there are multiple indentations instead of one continuous indentation, and so forth). In one embodiment, the indentation 1190 may be shaped to align the electronic device 1100 with a band.

FIG. 11B illustrates a top view of an electronic device 1100, according to one embodiment. The electronic device 1100 may include a top wall 1102. The electronic device 1100 may be coupled to a band 1192. The band 1192 may have an overlapping ring portion 1194 that covers a portion of the top wall 1102. The overlapping ring portion 1194 may avoid covering the components (e.g., display, power indicator 1105, one or more humidity, airflow, and/or temperature ports 1104, and so forth) on the top wall 1102 of the electronic device 1100. In one embodiment, the top wall diameter 1106 may be 1.4 inches. In one embodiment, the band 1192 may have an opening for the electronic device 1100. The opening diameter 1107 may be 0.8 inches.

FIG. 11C illustrates a view of the bottom surface of an electronic device 1100, according to one embodiment. The electronic device 1100 may include a bottom wall 1101, a top wall 1102, and a perimeter wall 1103. The perimeter wall 1103 may have an indentation 1190. The electronic device 1100 may be coupled to a band 1192. The band 1192 may have a snapping ring 1196 that couples with the indentation 1190. The band 1192 may have an outer casing 1198 that may be disposed adjacent to a substantial portion of the perimeter wall 1103. In one embodiment, the band 1192 does not cover the bottom wall 1101. In one embodiment the bottom wall diameter 1108 may be 1.4 inches.

Figure 12A:
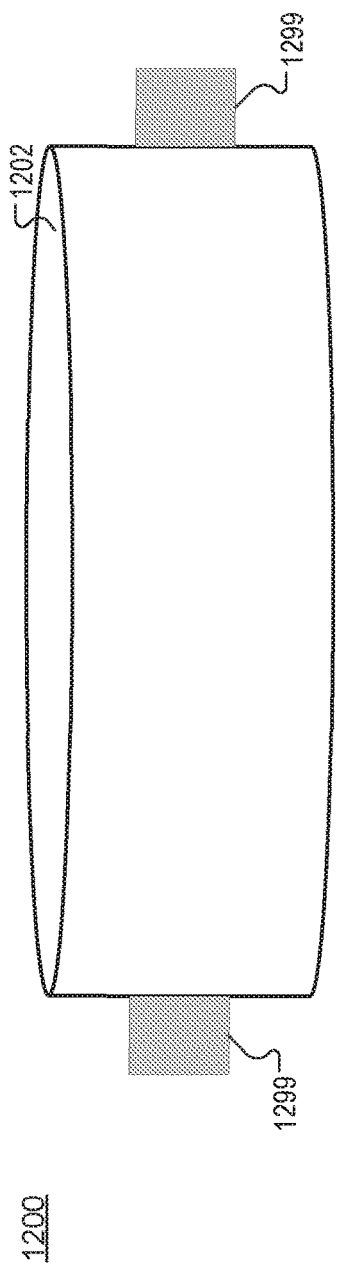
FIG. 12A illustrates a perspective bottom view of an electronic device, according to one embodiment.

FIG. 12A illustrates a top perspective view of an electronic device 1200, according to one embodiment. The electronic device 1200 may include a top wall 1202. Connector arms 1299 may be integrated into the electronic device 1200. The connector arms 1299 may couple with a band, sleeve, or other device to affix the electronic device 1200 to a user.

Figure 12B:
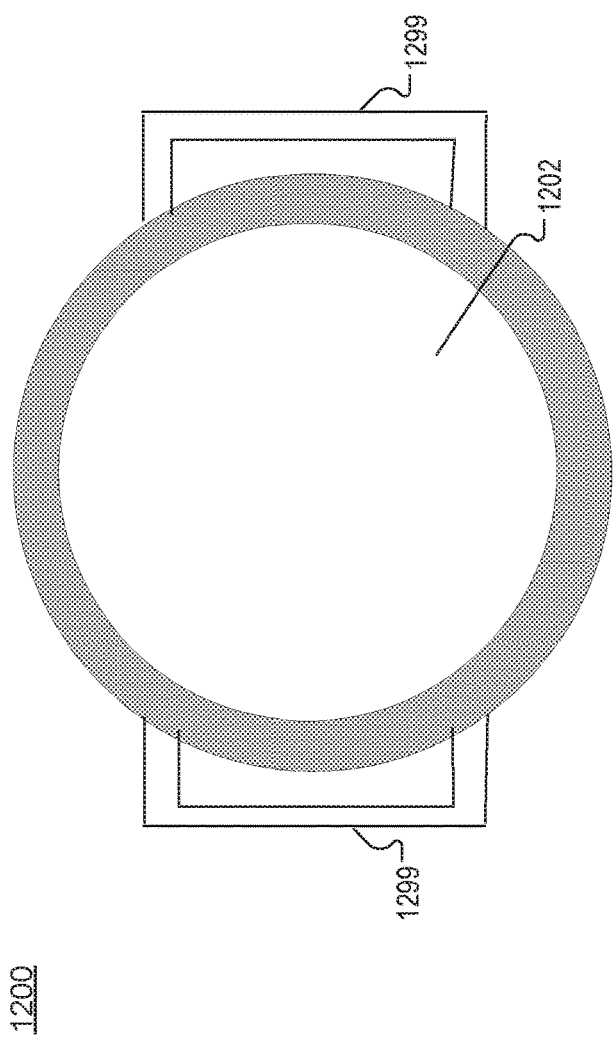
FIG. 12B illustrates a top view of an electronic device, according to one embodiment.

FIG. 12B illustrates a top view of an electronic device 1200, according to one embodiment. The electronic device 1200 may include a top wall 1202. The electronic device 1200 may include one or more connector arms 1299. The connector arms 1299 may couple with a band, sleeve, or other device to affix the electronic device 1200 to a user.

FIG. 13A illustrates a view of the top perspective surface of an electronic device 1300, according to one embodiment. The electronic device 1300 may include a top wall 1302. The electronic device 1300 may be coupled to a band 1392. The band 1392 may have an overlapping ring portion 1394 that covers a portion of the top wall 1302. The overlapping ring portion 1394 may avoid covering the components (e.g., display, power indicator, one or more humidity, airflow, and/or temperature ports, and so forth) on the top wall 1302 of the electronic device 1300. The band 1392 may have a first end 1322 and a second end 1324. The first end 1322 and second end 1324 may be a clasp. In one embodiment, the first end 1322 may be a loop and hook fastener and the second end 1324 may be a ring. In another embodiment, the first end 1322 may have holes and the second end 1324 may have a buckle to engage with the holes. In another embodiment, the first end 1322 may have holes and the second end 1324 may have a projection to engage with the holes.

FIG. 13B illustrates a view of a bottom surface of an electronic device 1300, according to one embodiment. The electronic device 1300 may include a bottom wall 1301 that includes an optical sensor, impedance pads, and other components. The electronic device 1300 may be coupled to a band 1392. The band 1392 may have an outer casing 1398 that may be disposed adjacent to a substantial portion of the perimeter wall of the electronic device. In one embodiment, the band 1392 may not cover the bottom wall 1301. In one embodiment, the band 1392 may avoid covering the optical sensor 1320, impedance pads 1350 and 1360, light sources 1330 and 1340, or other components on the projection 1315 of the bottom wall 1301.

Figure 14:
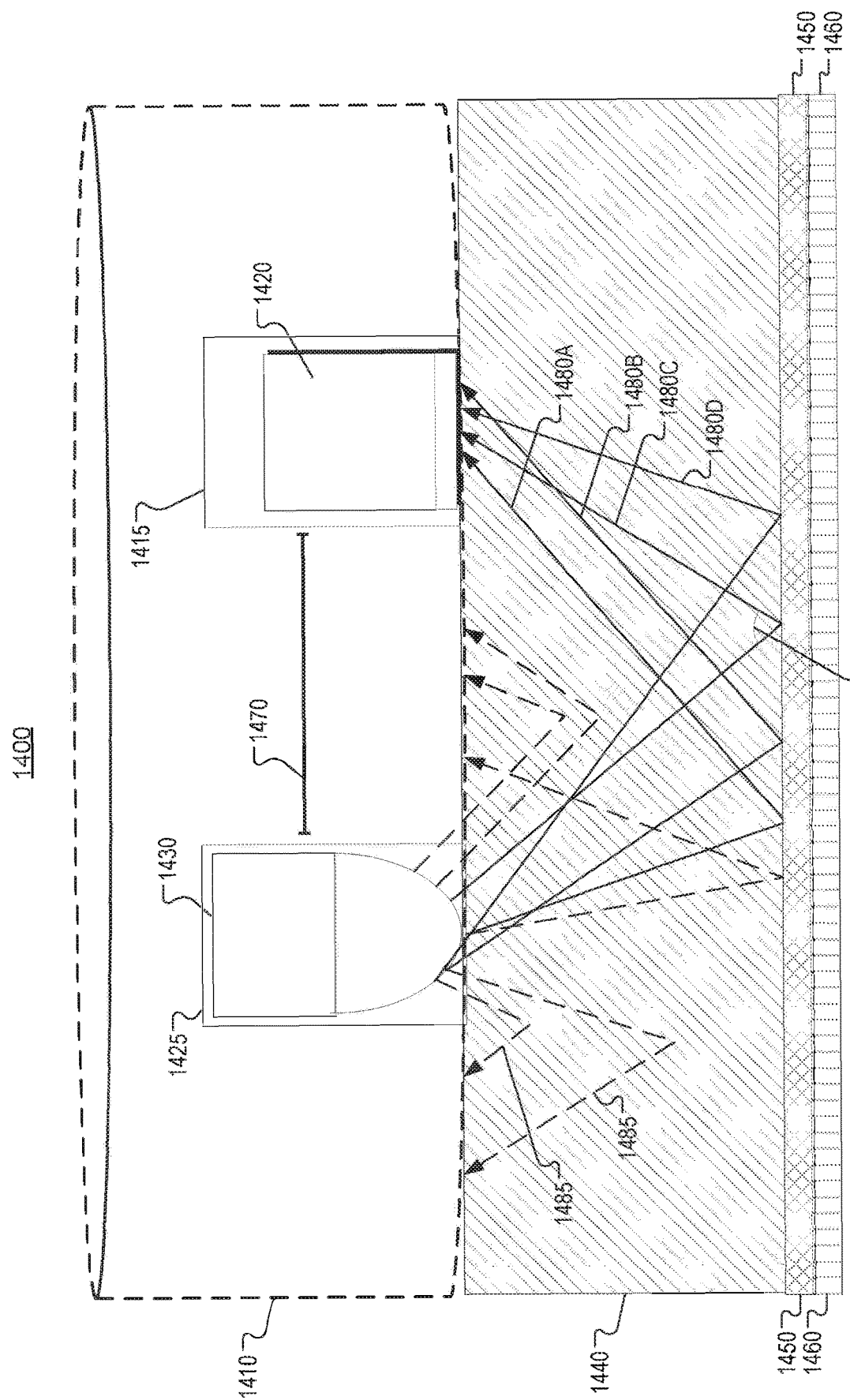
FIG. 14 illustrates a cross-sectional side view of an electronic device, according to one embodiment.

FIG. 14 illustrates a cross sectional side view of an electronic device 1400 interacting with a user, according to one embodiment. The electronic device 1400 includes a housing 1410 with cavities 1415 and 1425. The electronic device 1400 may further include a light source 1430 embedded in cavity 1425. In one example, the light source 530 may emit a full spectrum of wavelengths between 400 nanometers and 1800 nanometers. In another example, the light source 1430 is an LED emitting a discrete wavelength corresponding to a wavelength absorbed by a particular substance. In another example, the LED may emit a discrete wavelength between 535 nanometer and 735 nanometers to correspond to the wavelengths absorbed by sodium in the body. In another example, the LED may emit a discrete wavelength between 680 nanometers and 880 nanometers to correspond to the wavelengths absorbed by potassium in the body.

The electronic device 1400 further includes an optical sensor 1420. The optical sensor 1420 may receive backscatter 1480A-D that has been reflected by tissue in the body. The optical sensor may be equipped with a lens 1490. The lens 1490 may be any shape or thickness, and may focus, narrow, or direct the emitted light. Backscatter may be discrete or full spectrum waveforms that have been reflected off bodily tissue. In some examples, when the wavelengths hit body tissue or a substance in the body, the wavelengths are scattered by the tissue or substance. The sensor interface unit 506 may measure the amount of light that has scattered by causing the optical sensor 1420 to detect the amount of light that is scattered off body tissue. The processing device may determine the sodium or potassium level by comparing the amount of light emitted with the amount of light that is received at the optical sensor 1420. The amount of light received by the optical sensor can be compared to a previous amount of backscatter to determine if the level of the substance in the body is increasing or decreasing.

The optical sensor 1420 is separated from light source 1430 by a fixed distance 1470. Due to the angle of reflection 1475 of light waves entering the body, the fixed distance 1470 is fixed at a distance that allows the optical sensor 1420 to detect backscatter of light that has been reflected by a desired depth of body tissue. If, for example, the optical sensor 1420 is separated from the light source 1430 by 1 millimeter (mm) to 3 mm, the optical sensor 1420 may detect backscatter that has reflected off body tissue close to the surface, such as the epidermis and dermis layers 1440, of the skin (e.g. shallow backscatter 1485). As the optical sensor 1420 is increasingly separated from light source 1430, the optical sensor may detect light that has penetrated and been reflected off deeper parts of bodily tissue. However, if the optical sensor 1420 is separated from light source 1430 by too great of a fixed distance, the optical sensor 1420 will fail to detect enough light to take a measurement.

In one embodiment, optical sensor 1420 and the light source 1430 may be separated by a fixed distance 1470 for measuring waveforms that have reflected off a muscular-walled tube of the body such as an artery 1450 or vein 1460. Veins and arteries of the body contain concentrations of substances such as potassium and sodium that correlate with the hydration condition of a body. When a person becomes dehydrated, the skin pulls fluid from the blood causing the blood to become more concentrated with substances such as sodium and potassium. When a person has a higher than normal sodium content in the blood stream, it may be an indicator that the person is becoming dehydrated. Similarly, when a person has a higher than normal potassium content in the blood stream, it may be an indicator that the person is dehydrated. Thus, by measuring backscatter of wavelengths of light that are absorbed by sodium and potassium, the concentration of these substances in the blood stream can be determined. In another embodiment, it may be desirable to separate the optical sensor 1420 from the light source 1430 by between 6 millimeters and 8 millimeters to measure the backscatter from vein 1450 or artery 1460. In one embodiment, to prevent light that has been emitted from light source 1430 but that has not entered the body from reaching the optical sensor 1420, light piping or a barrier may be placed between the light source 1430 and optical sensor 1420.

Figure 15:
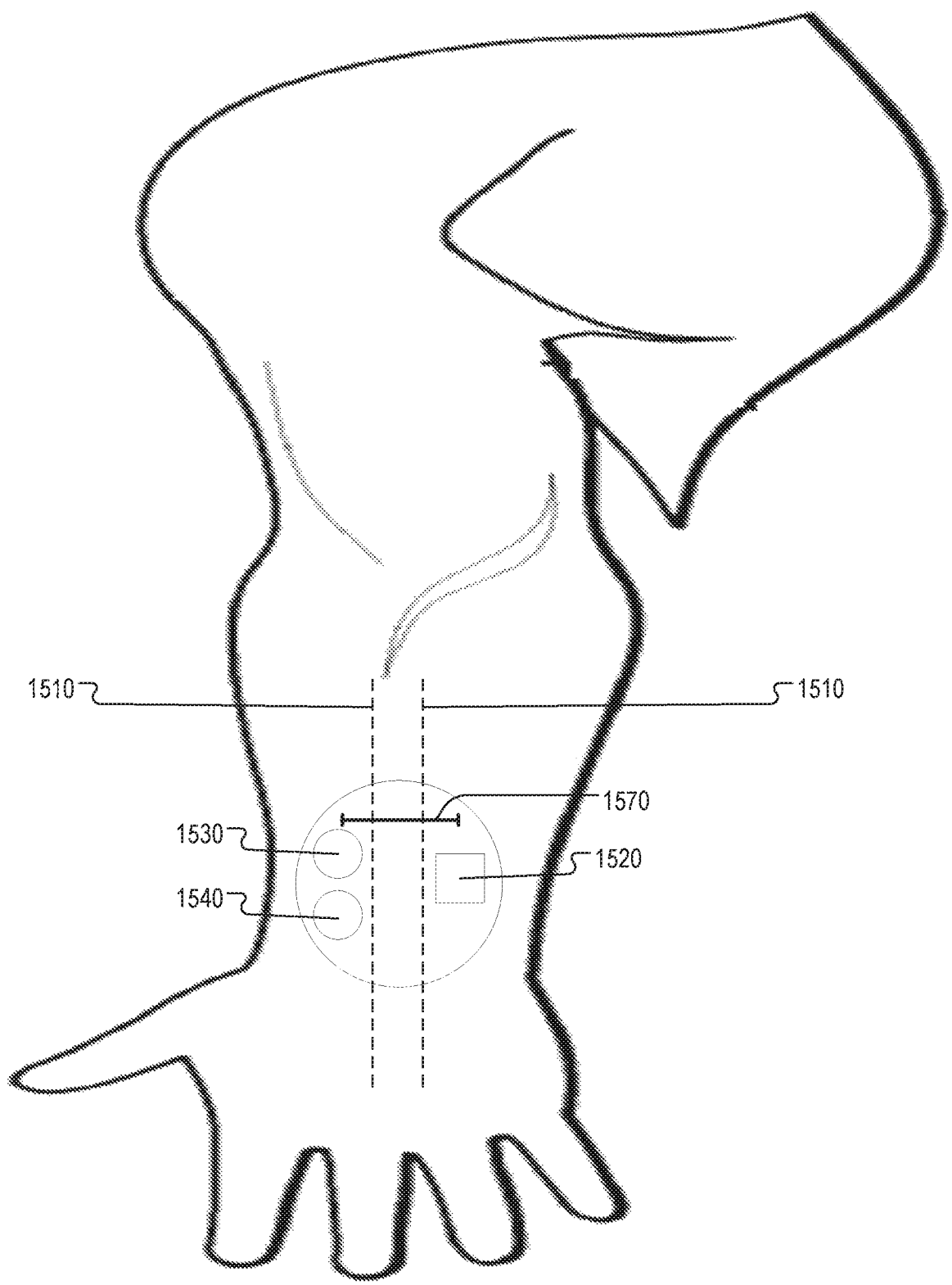
FIG. 15 illustrates an electronic device, according to one embodiment.

FIG. 15 illustrates, an electronic device 1500 oriented above the radial artery 1510 of a user, according to one embodiment. The electronic device 1500, as depicted, is oriented above the radial artery 1510 of a user's arm to measure physiological data, such as a hydration condition. The electronic device may be oriented above the radial artery 1510 to determine a concentration of substances such as potassium and sodium in a user's blood stream through a vein or artery. In one example, the electronic device is oriented above the radial artery 1510 because the radial artery 1510 is near the surface of the user's body. Measuring at a location that is near the surface of the skin minimizes the amount of backscatter that the optical sensor 1520 detects from light that has been scattered by structures or substances in the body other than the intended artery or vein. To measure waveforms that have reflected off the radial artery 1510, it may be desirable to position light sources 1530 and 1540 on one side of the radial artery 1510 and the optical sensor 1520 on the other side of the radial artery. This orientation allows the optical sensor 1520 to measure backscatter off the radial artery 1510. For example, when optical sensor 1520 is positioned on one side of the radial artery 1510 and light sources 1530 and 1540 are positioned on the other side of the radial artery 1510, light that is emitted from the light sources 1530 and 1540 is scattered off the blood or blood constituents in radial artery 1510 and detected by optical sensor 1520. However, if the electronic device was not positioned over an artery or vein, such as the radial artery 1510, there would not be a main conduit of blood between the light sources 1530 and 1540 and the optical sensor 1520 for the optical sensor 1520 to measure backscatter from. Moreover, optical sensor 1520 and light sources 1530, 1540 are spaced at fixed distance 1570 such that the optical sensor 1520 detects backscatter that has penetrated bodily deep enough to have reflected off the radial artery 1510. The radial artery 1510 is an example of a muscular-walled tube of the body.

In one embodiment, the electronic device 1500 measures the level of potassium, sodium, or another substance in the radial artery 1510 to determine a hydration condition of the body. Sodium and potassium, individually or in combination, regulate the water balance in the blood and tissues of a user. Potassium best absorbs light wavelengths between 680 nanometers and 880 nanometers. In one example, optical sensor 1520 detects wavelengths of 770 nanometers that have been reflected by potassium in the radial artery or other muscular-walled tube of the body to determine a potassium concentration in the blood stream. An increasing concentration of potassium in the blood stream may indicate that the body is becoming dehydrated.

In another embodiment, the electronic device 1500 measures the level of sodium in the body. In one example, excess sodium in the blood stream can cause an increase in the blood pressure of a user. In another example, a lack of sodium can cause a user to suffer nausea, vomiting, exhaustion, and dizziness. Additionally, sodium, along with potassium, is an electrolyte that when measured can be an indicator as to the hydration condition of the body. In one embodiment, sodium may absorb wavelengths between 535 nanometers and 735 nanometers. In one example, optical sensor 1520 may detect wavelengths of 620 nanometers that have been reflected by sodium in the radial artery 1510 or other muscular-walled tube of the body to determine a sodium concentration in the blood stream.

Figure 16:
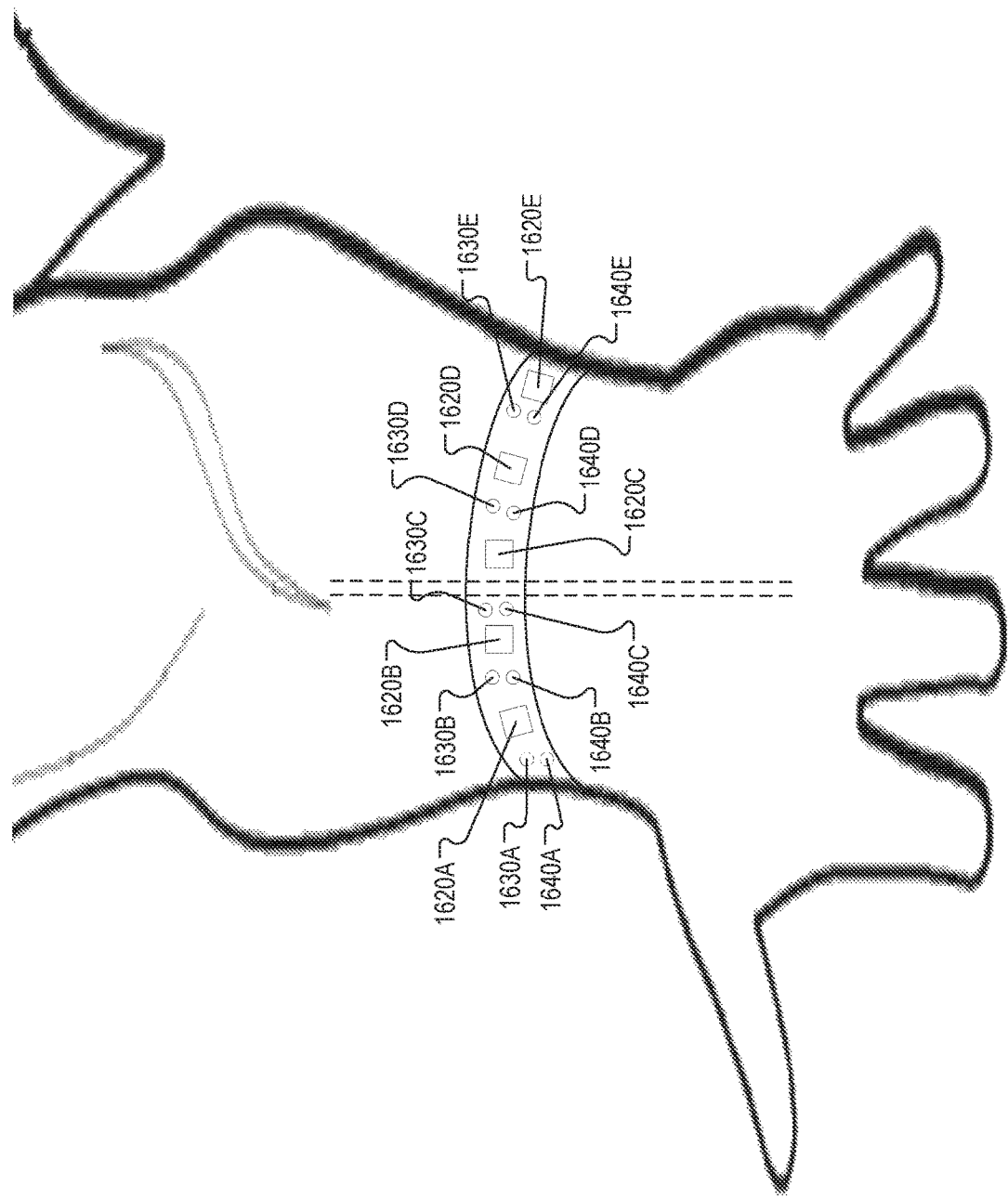
FIG. 16 illustrates an electronic device, according to one embodiment.

FIG. 16 illustrates, an electronic device 1600 having multiple optical sensors 1620A-E and light sources 1630A-E and 1640A-E affixed to a user, according to one embodiment. Electronic device 1600 may have multiple light source 1630A-E and 1640A-E and optical sensor 1620A-E configurations spaced around a wrist band, head band, torso band, or the like. In one embodiment, having multiple light source 1630A-E and 1640A-E and optical sensor 1620A-E configurations may improve measurement accuracy if the electronic device 1600 shifts on the body. For example, a user exercising may cause the electrical device 1600 to shift around on the user's wrist. In this example, each set of optical sensor 1620A-E and light sources 1630A-E and 1640A-E may be taking measurements of different locations around the wrist. The sensor interface may analyze the data from each set (e.g. optical sensor 1620C and light sources 1630C and 1640C) to determine which optical sensor and light source set is over the radial artery 1610 at any given time, and utilize that set's measurements to determine a hydration condition of the user. In one example, each optical sensor and light source set is concurrently taking measurements. When a set (e.g. optical sensor 1620C and light sources 1630C and 1640C) is reading measurement data within a specific range known to be within the measurement range of a user's baseline hydration level or within the range of previous measurement taken from the user's radial artery, that specific set is used to determine a hydration condition. Further, optical sensor and light source sets that are detecting measurements outside of the user's known range may be presumed to not be measuring from the radial artery and these measurements may be discarded. In another example, if multiple optical sensor and light source sets are within the range known to be within the range of previous measurements taken from the user's radial artery, each of these measurements will be aggregated and used to determine the hydration condition of the user. Each light source of a set of light sources (e.g., 1630A and 1640A, 1630B and 1640B, and so forth) may be equidistant from the corresponding optical sensor (e.g., 1630A and 1640B both equidistant from 1620A, and so forth). In one embodiment, one set of light sources may emit light at the same time to avoid an optical sensor 1620 sensing light from multiple sets of light sources. In another embodiment, multiple optical sensors 1620 may sense light emitted from one set of light sensors. For example, optical sensors 1620A and 1620B may be taking measurements of light sources 1630B and 1640B. In one embodiment, optical sensors 1620A and 1620B may concurrently be taking measurements of light sources 1630B and 1640B.

Figure 17:
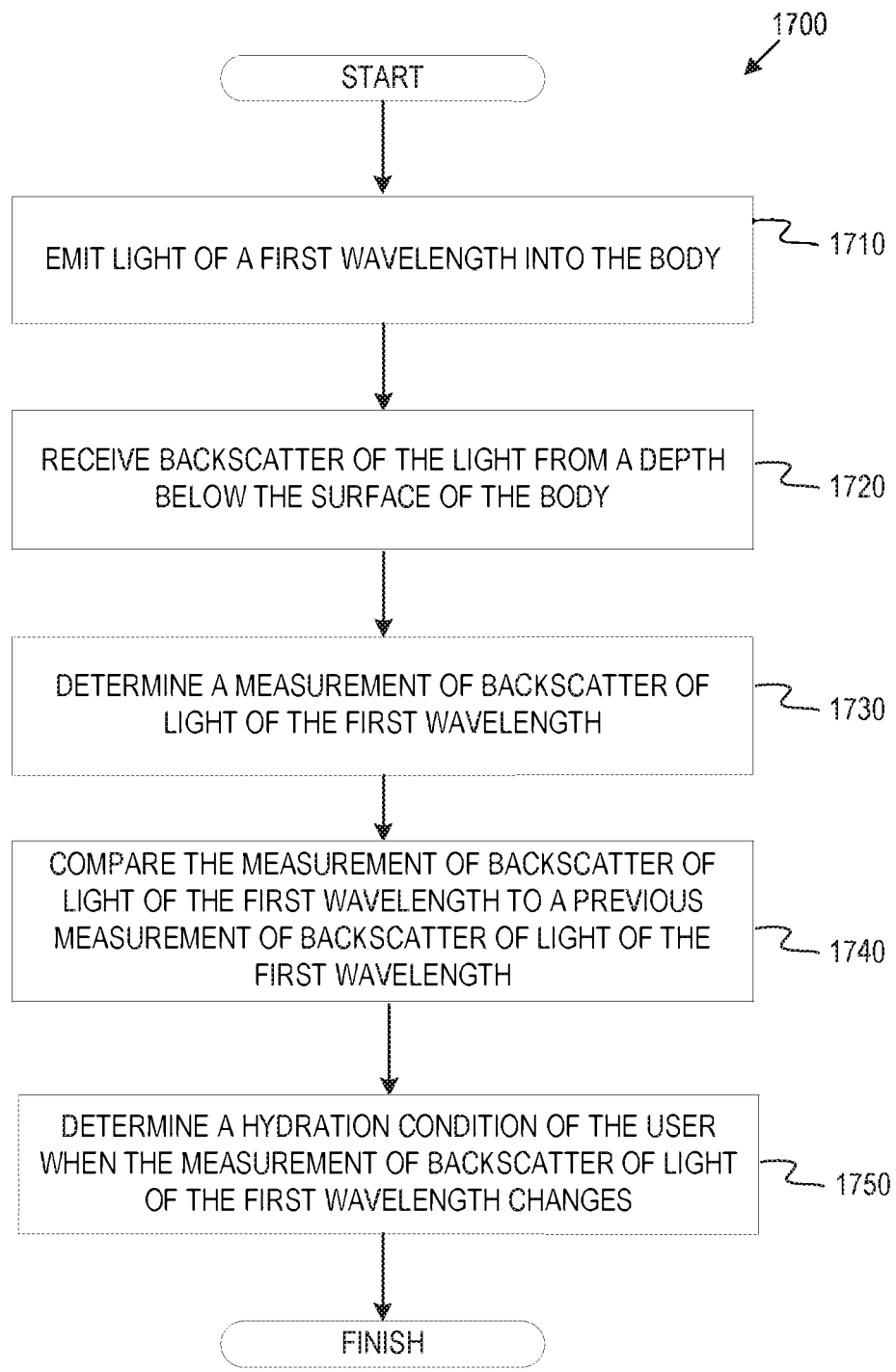
FIG. 17 illustrates a flow diagram of a method of determining a hydration condition, according to one embodiment.

FIG. 17 illustrates a flow diagram of a method 1700 of determining a hydration condition, according to one embodiment. The method 1700 may be performed by processing logic that may include hardware (e.g., circuitry, dedicated logic, programmable logic, microcode, and so forth), software (such as instruction run on a processing device, a general purpose computer system, or a dedicated machine, firmware, or a combination thereof. In one embodiment, the method 1700 may be performed, in part, by processing logic of processing device 804.

For simplicity of explanation, the method 1700 is depicted and described as a series of acts. However, acts in accordance with this disclosure can occur in various orders and/or concurrently and with other acts not presented as described herein. Furthermore, not all illustrated acts may be performed to implement the method 1700 in accordance with the disclosed subject matter. In addition, those skilled in the art will understand and appreciate that the method 1700 could alternatively be represented as a series of interrelated states via a state diagram or events.

The method can include, emitting light, from a first light source (1710). In one embodiment, the first light source can be coupled to a sensor interface, where the sensor interface can turn the first light source on to emit light at a first location into the user. In another embodiment, the first light source can emit the light at a first wavelength. In another embodiment, the light source can be affixed to a body of a user to emit into a body of the user. The first wavelength may be a discrete wavelength or a full spectrum of wavelengths. In one embodiment, the discrete wavelength may be between 535 nanometers and 735 nanometers. The discrete wavelength 535 nanometers and 735 nanometers may correspond to a wavelength that is absorbed by sodium. In another embodiment, a discrete wavelength may be between 680 nanometers and 880 nanometers. The discrete wavelength 680 nanometers and 880 nanometers may correspond to a wavelength that is absorbed by potassium. In another embodiment, the electronic device can include multiple light sources that emit light at different wavelengths. For example, the electronic device can include a first light source to emit light at a wavelength between 535 nanometers and 735 nanometers and a second light source to emit light at a wavelength between 680 nanometers and 880 nanometers.

The method can include receiving, by the optical sensor, backscatter of the light from a depth below the surface of the body (1720). In one embodiment, the optical sensor may be positioned at a fixed distance from the light source to detect backscatter from a muscular-walled tube of the body. A muscular-walled tube may be an artery or vein of the body.

The backscatter may be emitted from one or more light sources in block 1720 emitting one or more wavelengths.

The method can include, determining, by the processing device, an amount of backscatter of the light at the first wavelength (1730). In one embodiment, the processing device or sensor interface may receive the detected backscatter from the optical sensor to perform the determination. In one embodiment, the processing device or optical sensor may measure light of one or more wavelengths corresponding to one or more substances in the blood stream or other tissue from one or more light sources. In one embodiment, the processing device or sensor interface will measure the amount of received backscatter of light of a wavelength between 535 nanometers and 735 nanometers corresponding to a measurement of a wavelength that is absorbed by sodium in the body. In another embodiment, the processing device or sensor interface will measure the amount of received backscatter of light of a wavelength between 680 nanometers and 880 nanometers corresponding to a measurement of a wavelength that is absorbed by potassium in the body.

The method can include comparing, by the processing device or sensor interface, the amount of backscatter of light of the first wavelength to a previous amount of backscatter of light of the first wavelength (1740). In one embodiment, if the backscatter measurement of light of the first wavelength is greater than a previous measurement of backscatter of light of the first wavelength, it may indicate that that a concentration of a substance in the body that corresponds to the light of the first wavelength, such as sodium or potassium, has increased. In one example, an increase in the backscatter of light of the first wavelength may indicate that the level of potassium or sodium in the bloodstream or other tissue has decreased.

The method can include, determining, by the processing device or sensor interface, a hydration condition of the user when the amount of light that has backscattered changes (1750). The hydration condition of a user is affected by the concentration of electrolytes in the body including potassium and sodium. For example, the processing device may determine that the hydration condition of the user is a dehydration condition when the amount of sodium backscatter decreases from one measurement to the next. In another example, the processing device may determine that the hydration condition of the user is a hydrated condition when the amount of sodium backscatter increases. Alternatively, the processing device may determine that the hydration condition of a user is stable if there has not been a change in backscatter.

FIG. 18A illustrates an optical sensor 1810, a thermistor 1875, and multiple light sources 1822 and 1824 embedded into the electronic device 1800, according to one embodiment. In one embodiment, the electronic device 1800 may include light sources 1822 and 1824 that are equidistant from the optical sensor 1810. In some embodiments, the light sources 1822 and 1824 may be hermetically sealed, e.g. airtight, waterproof, sweat proof, dust proof, and so forth. Waterproofing rings 1830 and 1832 or other sealants may be used to hermetically seal the interior of the electronic device 1800. In some embodiments, other components such as the optical sensor 1810 may be hermetically sealed using waterproofing rings or other sealants to prevent water, sweat, dust, and other debris from entering the interior of the electronic device 1800.

FIG. 18B illustrates a cross sectional view of multiple light sources 1826 and 1828 embedded into an electrical device 1800, according to one embodiment. In one embodiment, light sources 1826 and 1828 may be positioned on one side of an artery or vein and may emit light of a wavelength corresponding to a wavelength absorbed by a substance of the body into the body of a user. In this example, light sources 1826 and 1828 may be hermetically sealed using waterproofing rings 1834 and 1836. Waterproofing ring 1834 and 1836 may prevent moisture from entering into the electrical device and reaching a circuit board 1840.

Figure 19A:
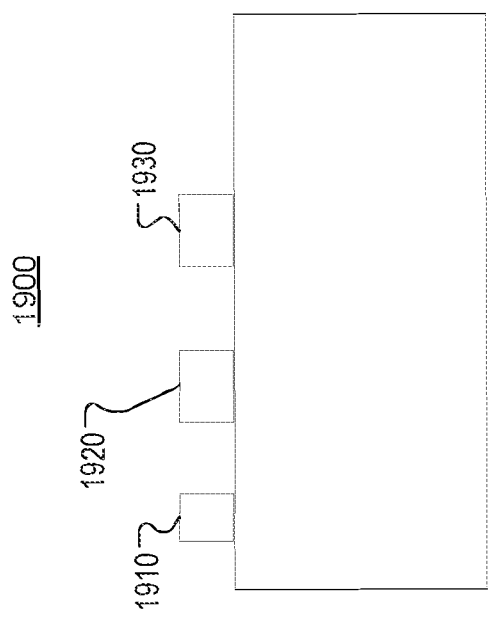
FIG. 19A illustrates an airflow sensor, according to one embodiment.
Figure 19B:
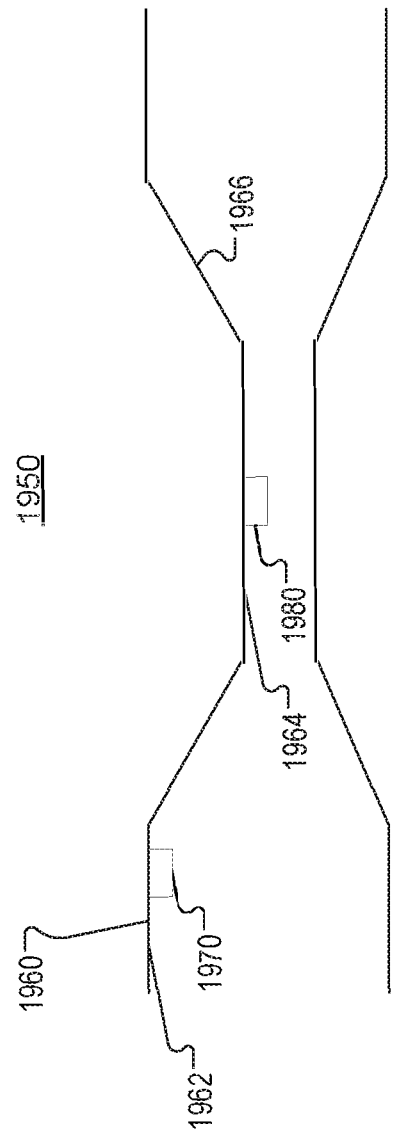
FIG. 19B illustrates an airflow sensor, according to another embodiment.

FIG. 19 illustrates an airflow sensor 1900, according to one embodiment. The electronic device 600 (FIG. 6) may include an airflow sensor 1900. The airflow sensor 1900 may include a micro-heating element 1910. The micro-heating element 1910 may be thermistor, a heated wire, a piezometer, a piezometer ring, and so forth. The airflow sensor 1900 may include a first heat sensor 1920 at a first location and a second heat sensor 1930 at a second location. The first heat sensor 1920 may determine a first temperature measurement at the first location and the second heat sensor 1930 may determine a second temperature measurement at the second location. As air passes over the micro-heating element 1910, a temperature gradient (e.g., a difference in temperature over a distance, and so forth) may form in the air passing by the first heat sensor 1920 and the second heat sensor 1930. As the velocity of the air passing by the first heat sensor 1920 and the second heat sensor 1930 increases, the difference in temperature measured at the first heat sensor 1920 and second heat sensor 1930 may increase. The processing device 504 (FIG. 5) may determine an air speed measurement from the first temperature measurement and the second temperature measurement. In one embodiment, the processing device 504 (FIG. 5) may determine the air speed measurement from a database in view of the first temperature measurement and the second temperature measurement. In one embodiment, the processing device 504 (FIG. 5) may calculate the air speed measurement from the first temperature measurement and the second measurement as described below.

In one embodiment, the processing device 504 (FIG. 5) may determine the air speed measurement from a voltage or current of the micro-heating element 1910. The processing device 504 (FIG. 5) may heat the micro-heating element 1910 electrically by delivering an electrical signal (e.g., voltage, electrical current, and so forth). The micro-heating element may have a resistance. The heat generated at the micro-heating element 1910 may be dependent on the electrical signal (e.g., voltage or electrical current) and the resistance of the micro-heating element 1910. The air passing by the micro-heating element 1910 may have a cooling effect on the micro-heating element 1910. The resistance of the micro-heating element may be dependent upon the temperature of the micro-heating element 1910. As the resistance changes due to the change in temperature caused by the airflow, the processing device 504 (FIG. 5) may determine a voltage output as the electronic device 600 (FIG. 6) attempts to maintain a specific variable (e.g., current, voltage, temperature, and so forth) constant following Ohm's law (current equals voltage divided by resistance). The processing device 504 (FIG. 5) can determine the airflow from the change in temperature at the micro-heating element 1910. In one embodiment, the processing device 504 (FIG. 5) may determine a change in ambient temperature from a temperature sensor (e.g., the ambient temperature sensor, and so forth) to determine a change in temperature at the micro-heating element due to airflow and not due to change in ambient temperature.

As the airflow changes, the feels-like temperature may change. Airflow can be created by the user moving, wind, or some other factor. In one embodiment, airflow can facilitate sweat evaporation and create a lower feels-like temperature. In another embodiment, airflow can transfer heat from the user to the air through convection causing a lower feels-like temperature.

The processing device 504 (FIG. 5) may combine the airflow measurement determined by an airflow sensor 1900 with an ambient temperature measurement to determine an adjusted baseline (e.g., wind chill factor, and so forth). The processing device may combine the airflow measurement, the ambient temperature measurement, and an ambient humidity measurement to determine an adjusted baseline (e.g., feels-like temperature, and so forth). The processing device 504 (FIG. 5) may compare the adjusted baseline with one or more other measurements (e.g., skin temperature measurement, previous sweat rate measurements, and so forth) to determine at least one of a current sweat rate, a predicted sweat rate, a change in sweat rate, and so forth.

Figure 20:
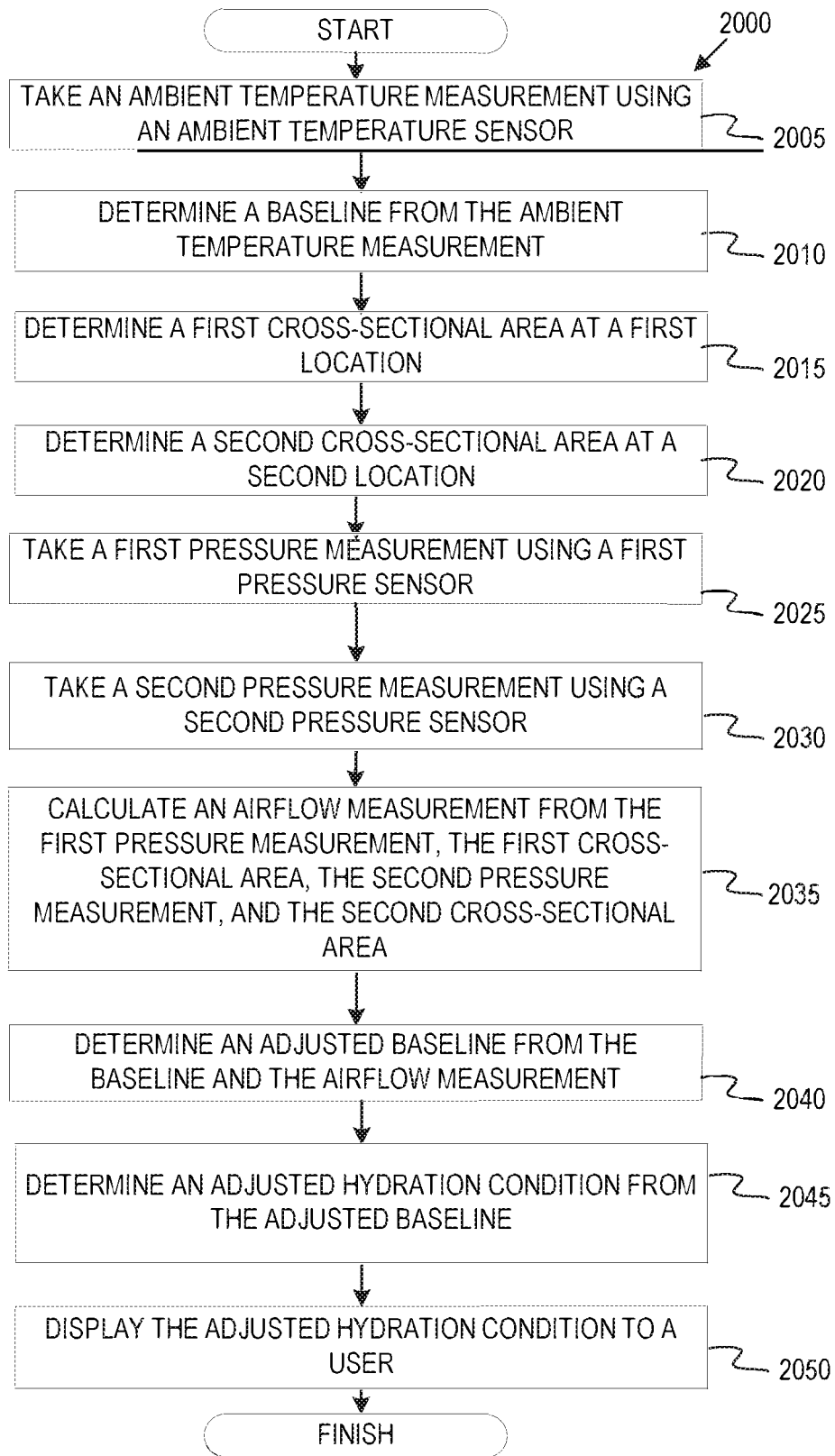
FIG. 20 illustrates a flow diagram of a method of determining a hydration condition, according to one embodiment.

FIG. 20 illustrates a flow diagram of a method 2000 of determining a hydration condition, according to one embodiment. The method 2000 may be performed by processing logic that may include hardware (e.g., circuitry, dedicated logic, programmable logic, microcode, and so forth), software (such as instruction run on a processing device, a general purpose computer system, or a dedicated machine, firmware, or a combination thereof. In one embodiment, the method 2000 may be performed, in part, by processing logic of processing device 504 (FIG. 5).

For simplicity of explanation, the method 2000 is depicted and described as a series of acts. However, acts in accordance with this disclosure can occur in various orders and/or concurrently and with other acts not presented as described herein. Furthermore, not all illustrated acts may be performed to implement the method 2000 in accordance with the disclosed subject matter. In addition, those skilled in the art will understand and appreciate that the method 2000 could alternatively be represented as a series of inter-related states via a state diagram or events.

The method can include, taking an ambient temperature measurement using an ambient temperature sensor (2005). The method can include, determining a baseline from the ambient temperature measurement (2010). For example, if the ambient temperature measurement is 75 degrees Fahrenheit (° F.), the baseline may also be 75° F.

The method can include, heating a heating element (2015). The heating element may be a micro-heating element 1910 (FIG. 19) such as a thermistor, a heated wire, a piezometer, a piezometer ring, or other type of heating element. The heating element may be located on the electronic device 600 (FIG. 6) to be exposed to airflow when the user is moving, when the wind is blowing, and so forth.

The method can include, taking a first temperature measurement using a first heat sensor (2020). The first heat sensor may be similar to first heat sensor 1920 (FIG. 19). The first heat sensor may be located on the electronic device 600 (FIG. 6) to be exposed to airflow when the user is moving, when there is wind, and so forth. The first heat sensor may be located on the electronic device 600 (FIG. 6) to be exposed to heat generated by the heating element.

The method can include, taking a second temperature measurement using a second heat sensor (2025). The second heat sensor may be located on the electronic device 600 (FIG. 6) to be exposed to airflow when the user is moving, when there is wind, and so forth. The second heat sensor may be located on the electronic device 600 (FIG. 6) to be exposed to heat generated by the heating element. The first heat sensor and second heat sensor may be located on the electronic device 600 (FIG. 6) to determine a difference in temperature depending on the velocity of the airflow.

The method can include, determining a temperature gradient from the first temperature measurement and the second temperature measurement (2030). In one embodiment, the temperature gradient may be in all three of the x-, y-, and z-directions. In another embodiment, the temperature gradient may be two of the x-, y-, and z-directions. In another embodiment, the temperature gradient may be in one of the x-, y-, and z-directions. The temperature gradient may be the change in temperature in one direction between the first heat sensor and the second heat sensor.

The method can include, determining an airflow measurement from the temperature gradient (2035). The processing device 504 (FIG. 5) may calculate the airflow measurement in view of the first and second temperature measurements. In one embodiment, the processing device 504 (FIG. 5) may use a root-mean-square speed equation (e.g., $v_{rms}$=sqrt(3*R*T/Mm), $v_{rms}$=sqrt(3*k*T/m), and so forth (where $v_{rms}$ is the root mean square of speed, Mm is the molar mass of the gas, R is the molar gas constant, T is the temperature, m is the mass of one molecule of gas, and k is the Boltzmann constant)). In one embodiment, the processing device 504 (FIG. 5) may use the Mach number (e.g., V=a*Ma*sqrt(T/To), where Vis the airspeed, a is the speed of sound at standard sea level, Ma is the Mach number, T is the temperature, and To is the standard seal level temperature, and so forth). In one embodiment, the processing device 504 (FIG. 5) may use some other equation (e.g., V=sqrt((To−T)/(2*cp)), V=sqrt(k*R*T), and so forth (where To is the stagnation temperature, cp is the air specific heat, Vis the velocity, k is the ratio of specific heats, R is the gas constant, and so forth)).

The method can include, determining an adjusted baseline from the baseline and the airflow measurement (2040). In one embodiment, the processing device 504 (FIG. 5) may calculate a wind chill factor. For example, the wind chill in degrees Fahrenheit (° F.) may be calculated by Wind Chill (° F.)=35.74+0.6215*T−35.75*(V0.16)+0.4275 T*(V0.16), where V is the wind speed value in miles per hour (mph) and T is the temperature in ° F. For example, if the baseline is 75° F. and the airflow measurement is 50 mph, the adjusted baseline may be 53° F.

The method can include, determining an adjusted hydration condition from the adjusted baseline (2045). The adjusted hydration condition may be a current hydration condition, a future hydration condition, a hydration condition rate (e.g., a sweat rate, and so forth), and so forth. In one embodiment, the processing device 504 (FIG. 5) may determine an adjusted hydration condition in view of previous hydration conditions of the user at a similar adjusted baseline. In another embodiment, the processing device 504 (FIG. 5) may determine an adjusted hydration condition in view of an average hydration condition stored in a database at a similar adjusted baseline. In another embodiment, the processing device 504 (FIG. 5) may determine an adjusted hydration condition in view of the adjusted baseline and one or more other measurements (e.g., ambient humidity measurement, skin temperature measurement, one or more physiological measurements, or other measurement).

The method can include, displaying the adjusted hydration condition to a user (2050). In one embodiment, the adjusted hydration condition may be displayed on a display device integrated into the housing (e.g., LEDs or GUI 630, and so forth). In one embodiment, LEDs may provide an indication of the user's hydration level (e.g., different colors for dehydrated, normal hydration, and overhydrated, amount of LEDs activated indicates the amount of hydration, activating an LED when the user is becoming dehydrated, and so forth). In one embodiment, a GUI may display a hydration level (e.g., percent hydrated, amount of water that the user needs to consume, time until dehydration, and so forth). In one embodiment, the adjusted hydration condition may be communicated to another device (e.g., a smart phone, a computer, and so forth). The other device may display the adjusted hydration condition.

Figure 21:
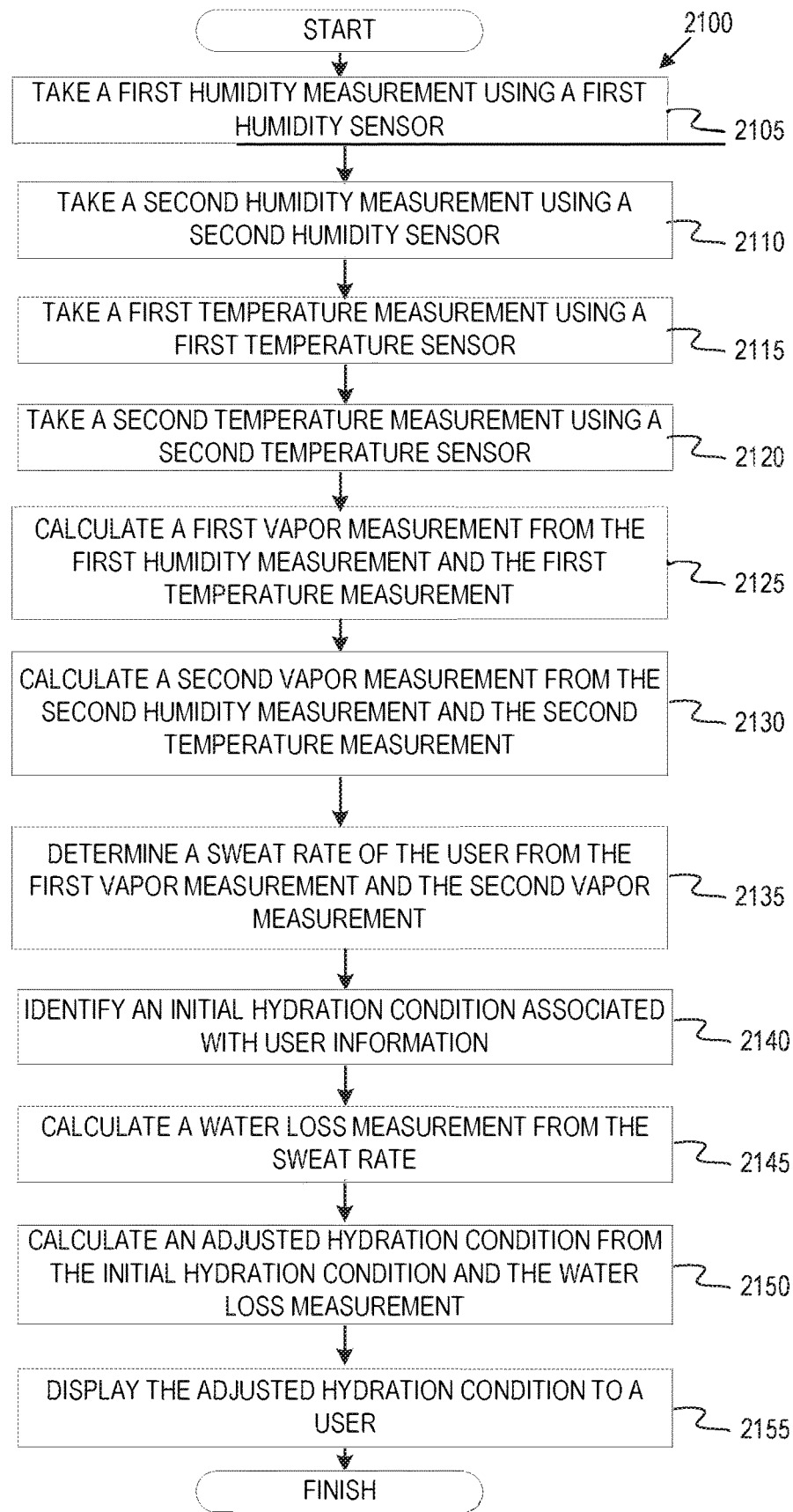
FIG. 21 illustrates a flow diagram of a method of determining a hydration condition, according to one embodiment.

FIG. 21 illustrates a flow diagram of a method 2100 of determining a hydration condition, according to one embodiment. The method 2100 may be performed by processing logic that may include hardware (e.g., circuitry, dedicated logic, programmable logic, microcode, and so forth), software (such as instruction run on a processing device, a general purpose computer system, or a dedicated machine, firmware, or a combination thereof. In one embodiment, the method 2100 may be performed, in part, by processing logic of processing device 504 (FIG. 5).

For simplicity of explanation, the method 2100 is illustrated and described as a series of acts. However, acts in accordance with this disclosure can occur in various orders and/or concurrently and with other acts not presented as described herein. Furthermore, not all illustrated acts may be performed to implement the method 2100 in accordance with the disclosed subject matter. In addition, those skilled in the art will understand and appreciate that the method 2100 could alternatively be represented as a series of interrelated states via a state diagram or events.

The method can include, taking a first humidity measurement using a first humidity sensor (2105). The first humidity measurement may be a relative humidity measurement of the air in the flume 610 (FIG. 6) at a first location.

The method can include, taking a second humidity measurement using a second humidity sensor (2110). The second humidity measurement may be a relative humidity measurement of the air in the flume 610 (FIG. 6) at a second location.

The method can include, taking a first temperature measurement using a first temperature sensor (2115). The first temperature measurement may be a dry bulb temperature measurement of the air in the flume 610 (FIG. 6) at a first location. Dry bulb temperature may be temperature of air measured by a sensor freely exposed to the air but shielded from radiation and moisture.

The method can include, taking a second temperature measurement using a second temperature sensor (2120). The second temperature measurement may be a dry bulb temperature measurement of the air in the flume 610 (FIG. 6) at a second location.

The method can include, calculating a first vapor pressure measurement from the first humidity measurement and the first temperature measurement (2125). In one embodiment, the processing device 504 (FIG. 5) may calculate a water vapor saturation pressure for the first temperature measurement. The processing device 504 (FIG. 5) may use the equation $P_{ws}=e1'(77.3450+0.0057*T-7235/T))/(TA8.2)$, where $P_{ws}$ is the water vapor saturation pressure (Pa), e is a constant 2.718, and T is the dry bulb temperature of the moist air (K). For example, if the temperature is 25 degrees Celsius (77 degrees Fahrenheit), the water vapor saturation pressure may be calculated at 3130 Pa (0.454 psi). In another embodiment, the processing device 504 (FIG. 5) may look up the water vapor saturation pressure in a database by the first temperature measurement. In another embodiment, the processing device 504 (FIG. 5) may calculate the first vapor pressure measurement directly from the first humidity measurement and the first temperature measurement. For example, the processing device 504 (FIG. 5) may calculate a first vapor pressure measurement by multiplying the water vapor saturation pressure (calculated using the first temperature measurement) by the first humidity measurement. For example, when the relative humidity is 50% and the water vapor saturation pressure is 3130 Pa at 25 degrees Celsius, the calculated first vapor pressure measurement is 1565 Pa.

The method can include, calculating a second vapor pressure measurement from the second humidity measurement and the second temperature measurement (2130). The second vapor pressure measurement may be calculated in the same or similar manner or in a different manner as the first vapor pressure measurement.

The method can include, determining a sweat rate of the user from the first vapor pressure measurement and the second vapor pressure measurement (2135). The processing device 504 (FIG. 5) may calculate the difference in time between the first vapor pressure measurement and the second vapor pressure measurements. The processing device 504 (FIG. 5) may obtain the difference in time from the time reference unit 516 (FIG. 5).

In one embodiment, the sweat rate may be a change in vapor pressure over time. The processing device 504 (FIG. 5) may calculate a change in vapor pressure rate at the flume by taking the difference between the first vapor pressure measurement and the second vapor pressure measurement and dividing by the difference in time.

In another embodiment, the sweat rate may be a mass flow rate. The processing device 504 (FIG. 5) may determine a first density of the air at the first vapor pressure measurement and a second density of the air at the second vapor pressure measurement. The density of air may be determined from a database given the vapor pressure of the air. The processing device 504 (FIG. 5) may determine a volume of the flume. The processing device 504 (FIG. 5) may calculate a change in mass flowrate by determining a change in density, multiplying by the volume, and dividing by the difference in time.

In another embodiment, the sweat rate may be a volume flow rate. In another embodiment, the sweat rate may be some other calculation or determination.

The processing device 504 (FIG. 5) may determine a sweat rate of the user from the sweat rate at the flume. The sweat rate at the flume may be the sweat rate measured in a defined size of flume of an electronic device located in a specific location on the user. In one embodiment, the processor 504 (FIG. 5) may determine a ratio of sweat rate at the flume to the sweat rate of the user. The processor 504 (FIG. 5) may use the sweat rate at the flume and the ratio of sweat rate at the flume to sweat rate of the user to determine the sweat rate of the user (e.g., entire body sweat rate, and so forth). For example, if the ratio of sweat rate at the flume to the sweat rate of the user were determined to be 0.01%, that sweat rate at the flume could be multiplied by 10,000 to calculate the total sweat rate.

The method can include, identifying an initial hydration condition associated with user information (2140). In one embodiment, the user information may include one or more of a height of the user, a weight of the user, or a gender of the user. In another embodiment, the user information may also include one or more of medical history, cardiovascular condition, past measurements, activity level, or recent liquid intake. In another embodiment, the initial hydration condition may be a volume or weight of water in the user. In another embodiment, the volume or weight of water in the user may be limited to the interstitial fluid or tissue water in the skin tissue of the user. In another embodiment, the initial hydration condition may be obtained from a database that includes average hydration information for a user by weight, height, gender and/or other user information. In another embodiment, the initial hydration condition may be received from an input device. The input device could be a GUI or touch screen display of the device, a smart phone, a weight scale, and so forth. In another embodiment, the initial hydration condition may be calculated from the user information. For example, given the user information, it may be determined that 60% of the weight of a user is body water, that ⅓ of the body water is extracellular fluid, and that ⅘ of the extracellular fluid is interstitial fluid. Therefore, it may be determined that 16% of the body weight of the user is interstitial fluid. The initial hydration condition may be determined to be 16% of the weight of the user or may be the water volume equivalent of 16% of the weight of the user.

The method can include, calculating a water loss measurement from the sweat rate (2145). The processing device 504 (FIG. 5) may calculate a water loss measurement from the sweat rate of the user and a time measurement from the time reference unit 516 (FIG. 5). For example, if the total sweat rate is 1 liter per hour, it may be calculated that over the course of one hour, the user had one liter or one kilogram of water loss. The total water loss measurement may be a total volume of water loss, a total mass of water loss, or some other determination.

The method can include, calculating an adjusted hydration condition from the initial hydration condition and the water loss measurement (2150). In one embodiment, the initial hydration condition may be a total mass or volume of water in the interstitial fluid or skin tissue water. In another embodiment, the initial hydration condition may be a total mass or volume of water of the user. In one embodiment, the adjusted hydration condition may be the difference between the initial hydration condition and the water loss measurement. In another embodiment, the adjusted hydration condition may be a percentage of interstitial fluid or skin tissue water that is remaining given the water loss measurement (e.g., adjusted hydration condition=(initial hydration condition−water loss measurement)/(initial hydration condition), and so forth). In another embodiment, the processor 504 (FIG. 5) may receive user input of water intake and water discharge (e.g., urination, vomiting, and so forth). The processor 504 (FIG. 5) may calculate the adjusted hydration condition by subtracting water loss and water discharge from the initial hydration condition and adding water intake. In another embodiment, a hydration of the individual can include a hypo-hydrated level (dehydrated or under hydrated condition), a euhydrated level (normal hydration condition), or a hyper-hydrated level (over hydrated condition). In one embodiment, the adjusted hydration condition may indicate that the individual is trending towards a dehydrated condition. In another embodiment, the adjusted hydration condition may indicate a user is trending towards a normal hydration condition. In another embodiment, the adjusted hydration condition may indicate that the individual is trending towards an over hydrated condition.

The method can include, displaying the adjusted hydration condition to a user (2155). In one embodiment, the adjusted hydration condition may be displayed on a display device integrated into the housing (e.g., LEDs or GUI 630, and so forth). In one embodiment, LEDs may provide an indication of the user's hydration level (e.g., different colors for dehydrated, normal hydration, and overhydrated, amount of LEDs activated indicates the amount of hydration, activating an LED when the user is becoming dehydrated, and so forth). In one embodiment, a GUI may display a hydration level (e.g., percent hydrated, amount of water that the user needs to consume, time until dehydration, and so forth). In one embodiment, the adjusted hydration condition may be communicated to another device (e.g., a smart phone, a computer, and so forth). The other device may display the adjusted hydration condition.

Figure 22:
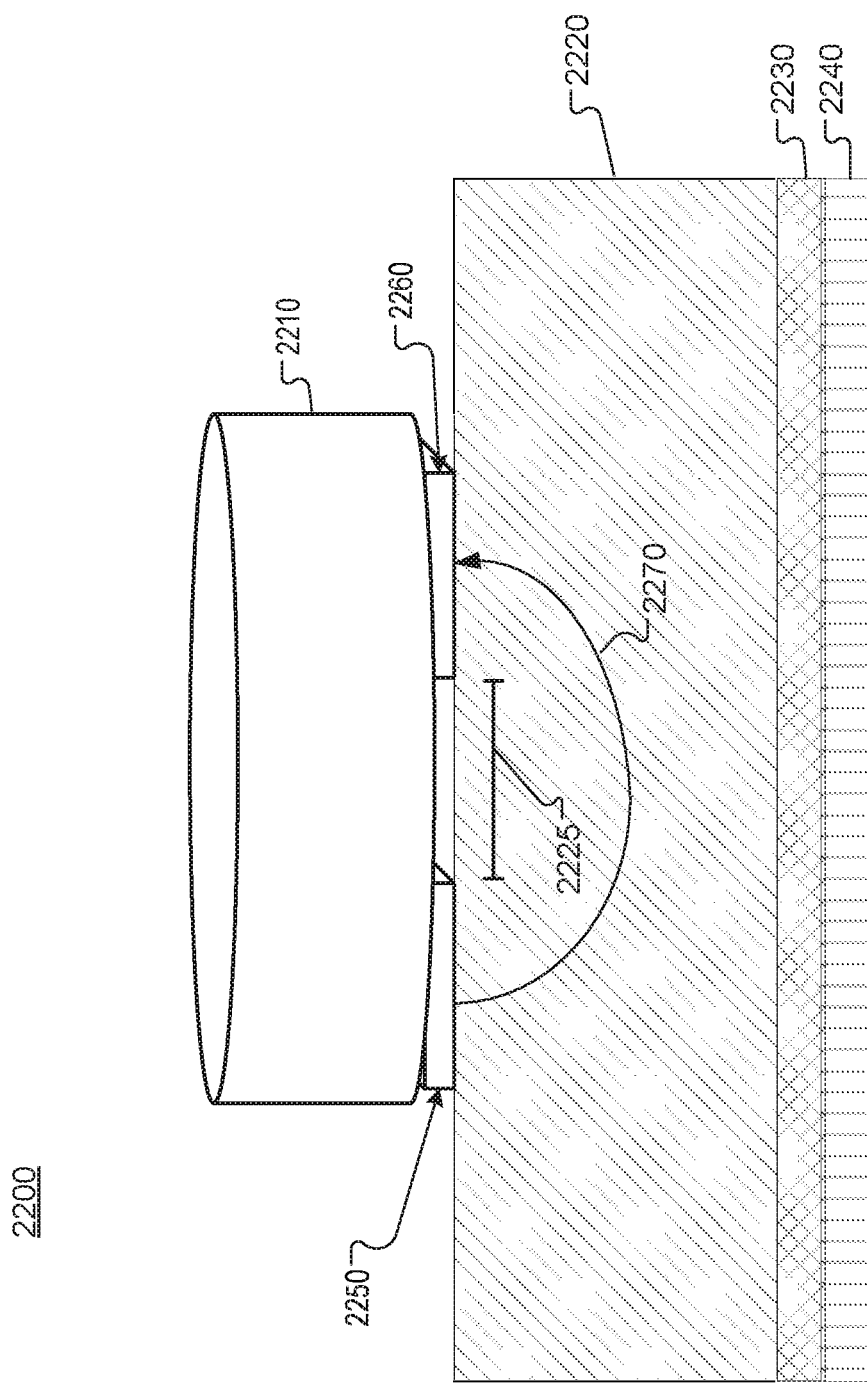
FIG. 22 illustrates an electronic device, according to one embodiment.

FIG. 22 illustrates an electronic device 2200 interacting with a user, according to one embodiment. Electronic device 2200 may include housing 2210. Housing 2210 may be embedded with impedance pads 2250 and 2260. The second impedance pad 2260 may be separated from the first impedance pad 2250 by a fixed distance 2225 to measure a portion of the electric signal that has passed through the dermis or epidermis layers of the skin. In one example, sensor interface unit 806 uses impedance pad 2250 to transmit an electric signal into the skin of a user. The sensor interface unit 806 uses the second impedance pad 2260 to receive electric signals. The second impedance pad 2260 may receive a portion of the electric signal transmitted by impedance pad 2250. The level of electricity of the electric signal that is received at the second impedance pad 2260 depends in part on the fixed distance 2225 between the first impedance pads 2250 and the second impedance pad 2260. For example, if the impedance pads 2250 and 2260 are separated by between approximately 1 millimeters (mm) and 4 mm, the second impedance pad 2260 will receive a portion of the electric signal that has travelled through a shallow portion of the skin, such as the epidermis layer of the skin. In another example, when impedance pads 2250 and 2260 are separated by a fixed distance of approximately 12 mm to approximately 18 mm, the second impedance pad 2260 may receive a portion of the transmitted electric signal that has travelled through the dermis layer 2220 of the skin. Alternatively, if impedance pad 2250 is separated from second impedance pad 2260 by a distance of greater than 20 mm, the second impedance pad 2260 may not receive the portion of the electric signal or may receive a portion of the electric signal that has been transmitted to a depth below the dermis layer such as a layer of veins 2230 or arteries 2240 and the measurement may be inaccurate. Blood constituents in the veins 2230 or the arteries 2240 may interfere with the electric signal that was transmitted into the veins or artery layer because the blood constituents may absorb a portion of the electric signal or create noise within the electric current or absorb all of the electric current.

In another embodiment, the portion of the electric signal received by the second impedance pad 2260 depends in part on the size of the impedance pads 2250 and 2260 and the power level of the electric signal transmitted from the first impedance pad 2250. For instance, a second impedance pad 2260 with a surface area of 5 mm2 may receive a larger portion of the electric current transmitted by the first impedance pad 2250 than when the second impedance pad 2260 has a surface area of 3 mm2. In one embodiment, the size and spacing of the impedance pads may be different depending on the part of the body where the measurement is taking place. In one example, when an impedance measurement is being taken at the wrist, a shallow measurement may be taken to avoid veins and arteries that are close to the surface of the skin. In this example, the fixed distance may be spaced closer together when measuring at the wrist location than the fixed distance would be when measuring at the arm to take a shallow measurement. In a second example, the impedance pads may have less surface area to take a measurement at a location, such as the wrist, where a more shallow measurement would provide a more accurate measurement. In another example, when an impedance measurement is being taken at the arm, a deeper measurement may be taken because the veins 2230 and arteries 2240 are located further below the surface of the skin. In this example, impedance pads 2250, 2260 may have more surface area and/or the fixed distance may be larger. The electric signal strength may also be enhanced by adding water or conductive gel to the impedance pads 2250 and 2260. For example, if a user puts water or conductive gel on the bottom surface of the electronic device 2200 before putting the electronic device 2200 in contact with the skin, the second impedance pad 2260 may receive a larger portion of the electric current transmitted by the first impedance pad 2250 than when the user does not put water or conductive gel on the bottom surface of the electronic device 2200.

Figure 23:
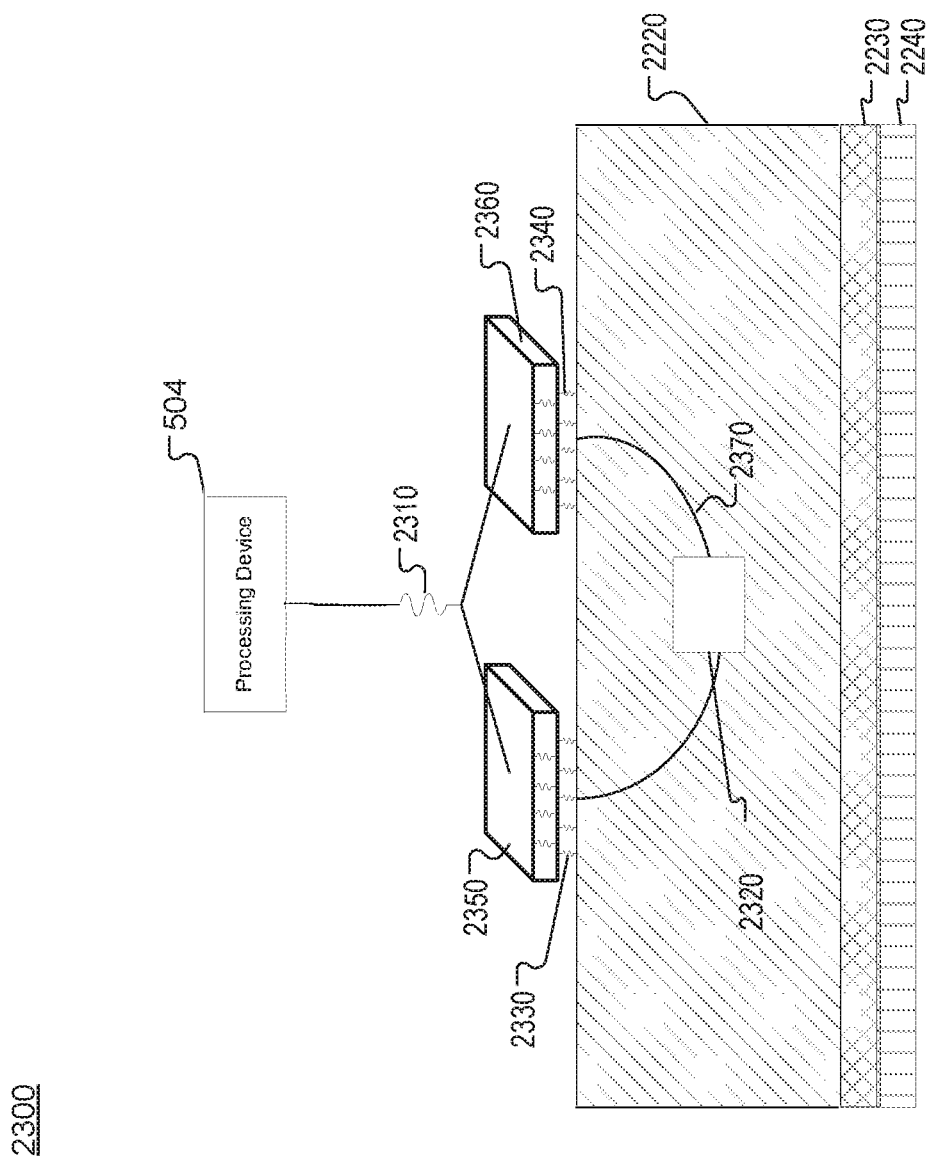
FIG. 23 illustrates a processing device taking an impedance measurement, according to one embodiment.

FIG. 23 illustrates a processing device 504 (FIG. 5) taking an impedance measurement 2320 from the body of a user, according to one embodiment. In one embodiment, impedance sensor may transmit electric signal 2370 from a first impedance pad 2350 into the skin of a user. The human skin includes an epidermis layer, a dermis layer 2220 (FIG. 22), and a subcutaneous fat layer. Below the skin are veins 2230 and arteries 2240 (FIG. 22). In one embodiment, an electric signal may be transmitted into the dermis or epidermis layer of the skin. An impedance measurement 2320 may be taken from the dermis layer 2220 (FIG. 22) or epidermis layer because these layers develop sweat when a body perspires.

The impedance measurement may be effected by one or more resistances or impedances in the measurement process. In one embodiment, air resistance 2330 and 2340 may interrupt the impedance measurement 2320 performed by the electronic device 2300. In one example, sweat, electrocardiogram gel, water, spit, or other conductive solution may be used to minimize any air gaps between the surface of the skin and the impedance pads 2350 and 2360. In one embodiment, first impedance pad 2350 and second impedance pad 2360 are recessed into the housing to reduce or minimize the air resistance 2330 and 2340 between the impedance pads 2350 and 2360 and the skin. Further, the impedance pads 2350 and 2360 may be constructed out of a conductive material with a resistance quality of equal to or less than 10 mega ohms to minimize the resistance in the impedance pads themselves.

Figure 24:
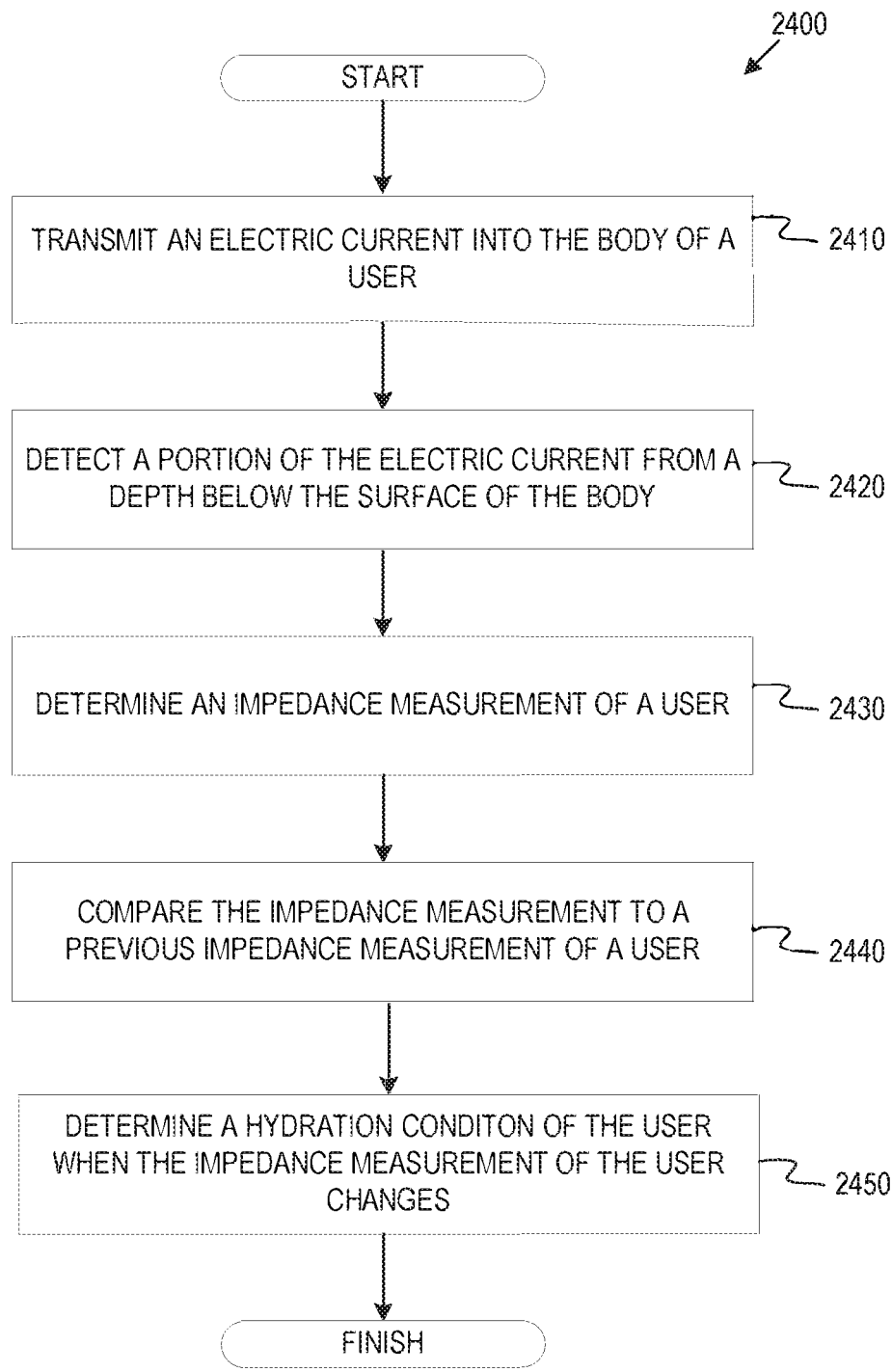
FIG. 24 illustrates a flow diagram of a method of determining a hydration condition, according to one embodiment.

FIG. 24A illustrates a flow diagram of a method 2400 of determining a hydration condition, according to one embodiment. The method 2400 may be performed by processing logic that may include hardware (e.g., circuitry, dedicated logic, programmable logic, microcode, and so forth), software (such as instruction run on a processing device, a general purpose computer system, or a dedicated machine, firmware, or a combination thereof. In one embodiment, the method 2400 may be performed, in part, by processing logic of processing device 804.

For simplicity of explanation, the method 2400 is depicted and described as a series of acts. However, acts in accordance with this disclosure can occur in various orders and/or concurrently and with other acts not presented as described herein. Furthermore, not all illustrated acts may be performed to implement the method 2400 in accordance with the disclosed subject matter. In addition, those skilled in the art will understand and appreciate that the method 2400 could alternatively be represented as a series of interrelated states via a state diagram or events.

The method can include the sensor interface using the first contact terminal of an impedance sensor to transmit an electric current into the body of a user (2410). In one embodiment, the first contact terminal may be an electrode pad. The first contact terminal may be coupled to the sensor interface and the processing device.

The method can include, the sensor interface using the second contact terminal of the impedance sensor to receive a portion of the electric current from a depth below the surface of the body of the user (2420). In one embodiment, the second contact terminal is separated from the first contact terminal by a fixed distance. In one example of this embodiment, the first and second contact terminals are separated by a fixed distance of 12 mm to 18 mm to measure the portion of the electric current that has traveled through the dermis or epidermis layer of the skin. Alternatively, for areas of the body where the veins and arteries are near the surface of skin, the fixed distance may be less than 12 millimeters. Moreover, in areas of the body where the veins and arteries are further below the surface of the skin, the fixed distance may be greater than 18 millimeters. In another embodiment, the size of the contact terminals and the strength of the electric signal may affect the fixed distance that would be used to measure the portion of the electric signal that has traveled through the dermis or epidermis layer of the skin.

The method may include the processing device or sensor interface determining an impedance measurement of a user (2430). The processing device or sensor interface may use the received portion of the electric signal from the optical sensor to perform the impedance measurement. The impedance measurement will be based at least in part on the strength of the received portion of the electric current or the speed at which the received electric current travels between the first contact terminal and the second contact terminal.

The method may further include the processing device or sensor interface comparing the impedance measurement to a previous impedance measurement (2440). By comparing the impedance measurement to a previous impedance measurement, the processing device can determine if the impedance in the skin has increased or decreased. An increase in skim impedance may indicate that the skin is becoming dry. A decrease in skin impedance may indicate that the skin is perspiring or is otherwise becoming wet.

The method may further include the processing device or sensor interface determining that a hydration condition of the user has changed when the impedance measurement of the user changes (2450). In one example, the processing device or sensor interface may determine that a person is becoming more hydrated when the impedance measurement of the skin has decreased from a normal skin impedance level of the user. In another example, the processing device or sensor interface may determine that a person is becoming less hydrated when the impedance measuring of the skin has increased from the normal skin impedance level of the user.

Figure 25:
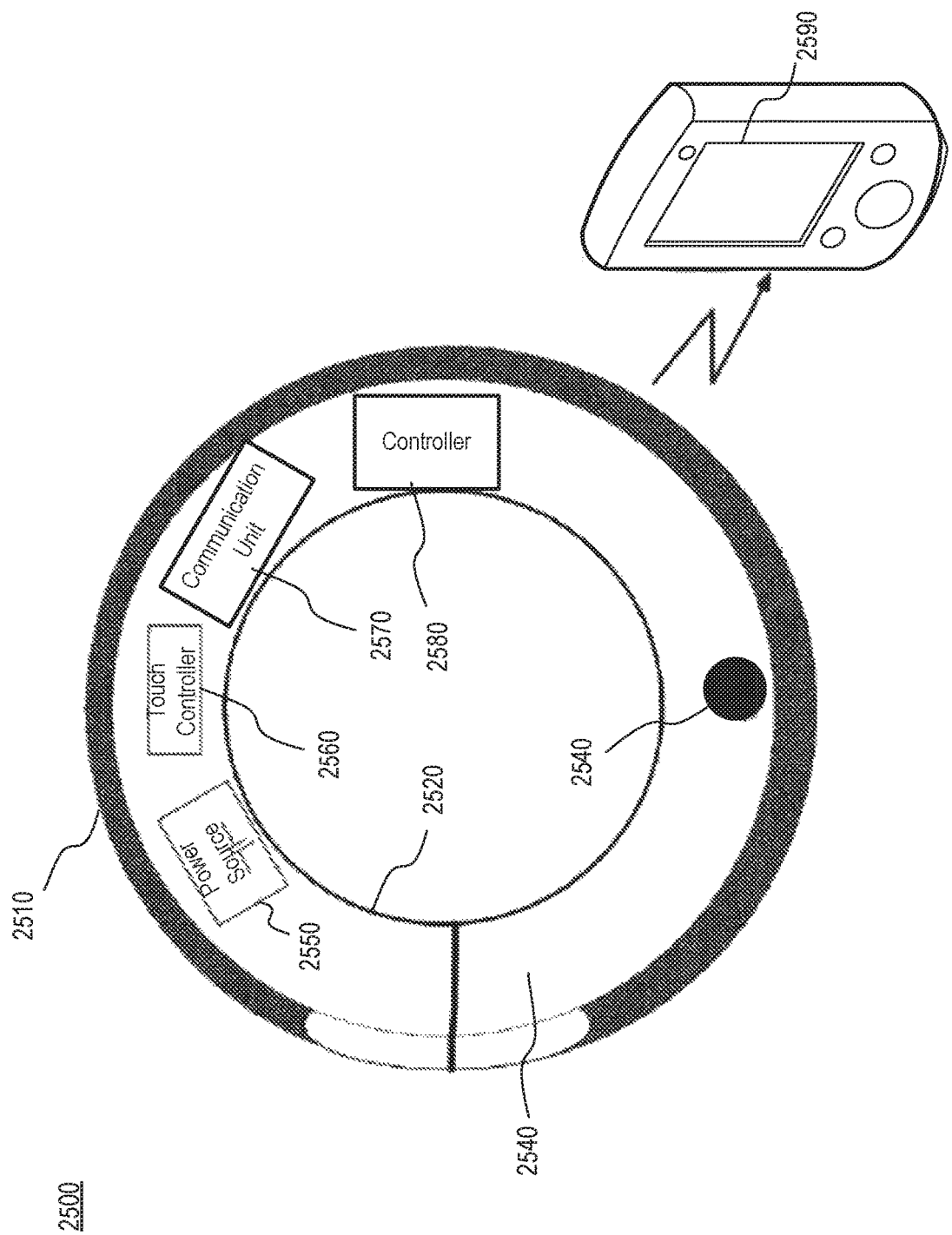
FIG. 25 illustrates an electronic device, according to one embodiment.

FIG. 25 illustrates an electronic device 2500 communicating with an external electronic device 2590, according to one embodiment. The electronic device 2500 can be a substantially circular band with an outer surface 2510 and an inner surface 2520. In one example, the outer surface 2510 or the inner surface 2520 can be made of flexible or non-rigid material, such as rubber, polyurethane, and so forth. In another example, the outer surface 2510 or the inner surface 2520 can be made of semi-rigid or rigid material, such as plastic, metal, and so forth. In another example, a portion of the outer surface 2510 or the inner surface 2520 can be the flexible or non-rigid material and a portion of the outer surface 2510 or the inner surface 2520 can be the semi-rigid or rigid material. In another example, a portion of the inner surface 2520 that contacts a body of the user is a conductive material. For example, one or more sensors 2540 are bio-impedance sensors that are conductive rubber pads that contact the body of the user and are used by processing logic to make bio-impedance measurements.

In one example, a cavity or chamber 2540 can be between the outer surface 2510 and an inner surface 2520. The cavity or chamber 2540 can include modules, units, systems, subsystems, or devices of the electronic device 2500. For example, the cavity or chamber 2540 can house a power source 2550, a graphical user interface or touch controller 2560, a communication unit 2570, a controller 2580, one or more sensors 2540, and/or other units. In one example, the communication unit 2570 can wirelessly communicate with an external electronic device 2590. In another example, the power source 2550 can provide power to other units or modules of the electronic device 2500. In one example the touch controller 2560 can receive user input from an input device. In one example, the input device can be a graphical user interface (GUI) or a touch display and be operable to receive input via the GUI or the touch display. In another example, the input device can receive communications from other devices via a communication network (e.g., a wireless network) or a communication connection (such as a universal serial bus). In another example, the controller 2560 can control systems and subsystems of the electronic device 2500.

In another example, the power source 2550 can be a battery, such as a rechargeable battery. The power source 2550 can receive power from another power source such as via a cord plugged into a power source or using wireless power such as inductive wireless charging or resonant wireless charging. In another example, the electronic device 2500 can have one or multiple sensors 2540 (e.g., a sensor array). In one example, the multiple sensors 2540 can be different types of sensors.

In one example, the electronic device 2500 can receive physiological information such as a hydration condition and/or an environmental condition of a user of the electronic device 2500 from another device. In another example, the electronic device 2500 can have a touch controller 2560 to receive user input physiological information and/or environmental information. In one example, a power source 2550, a touch controller 2560, a communication unit 2570, a controller 2580, one or more sensors 2540 can be in direct or indirect communication with each other. For example, the touch controller 2560 receives user input information from the input device and communicates the user input information to the controller 2580. In this example, the controller 2580 can include a processor or processing device to analyze or process the user input information. In another example, the sensor 2540 can take a physiological measurement and communicate physiological information to the external electronic device 2590 via the communication unit 2570. In one embodiment, the external electronic device 2590 is an electronic device with a processor, such as a smartphone, electronic tablet, or personal computer. In another embodiment, the external electronic device 2590 is a cloud computing system or a server. The external electronic device 2590 can analyze or process data or information received from the electronic device 2500. In one example, the external electronic device 2590 can store the processed data or information. In another example, the external electronic device 2590 can send the processed data or information back to the electronic device 2500.

Figure 26:
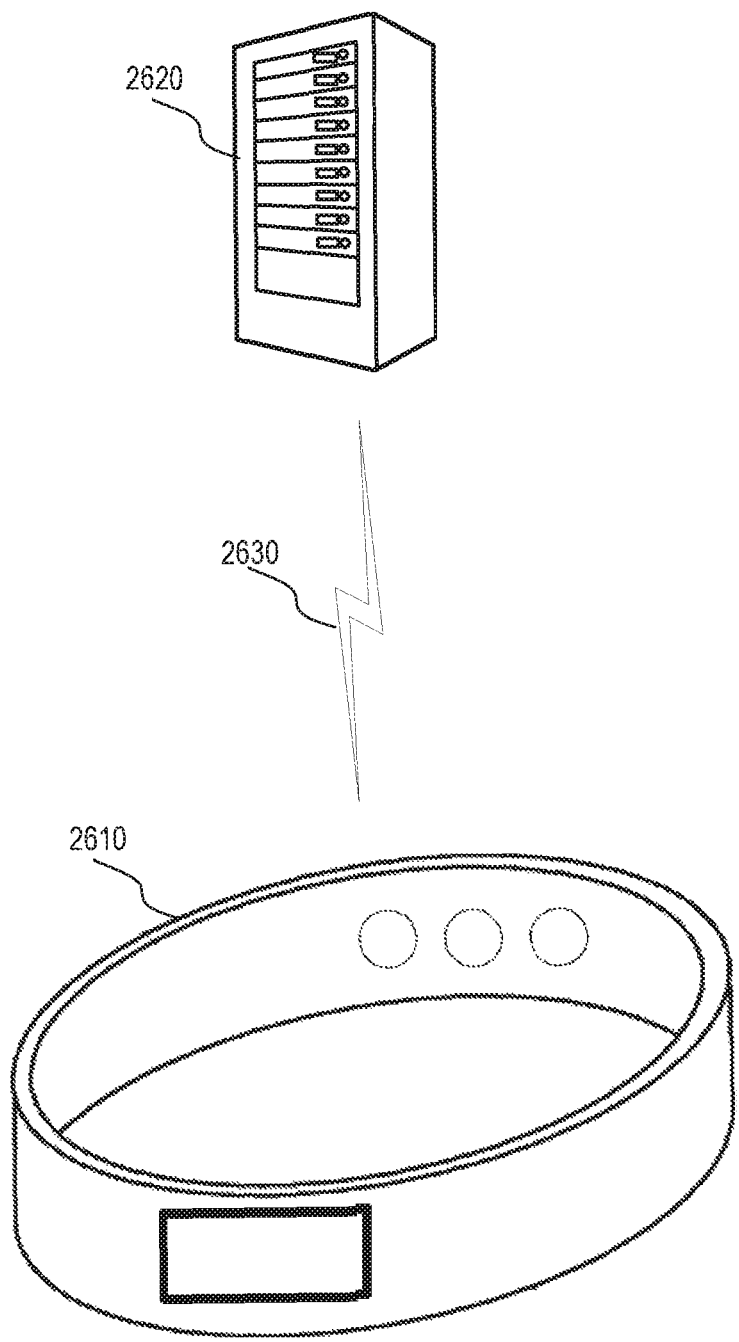
FIG. 26 illustrates an electronic device in direct communications with a computing device, according to one embodiment

FIG. 26 illustrates an electronic device 2600 in direct communications with a computing device 2620, according to one embodiment. In one example, sensor measurements collected and/or stored by the electronic device 2610 can be processed or analyzed by a processor or processing device of the electronic device 2600 and/or by a computing device 2620 in communication with the electronic device 2600. The electronic device 2600 can be in direct communication 2630 with the computing device 2620. In one example, the direct communication 2630 can be a communication link using BLUETOOTH® technology, a communication link using ZIGBEE® technology, radio signal, or other direct communication systems. In another example, the other computing device 2620 can be a server that stores information, such as sensor measurements or hydration condition information previously taken by the electronic device 2610 or sensor measurements or hydration condition information taken from a group of individuals, as discussed herein. In another example, the computing device 2620 can be a mobile computer device, such as a laptop computer, tablet, or a smartphone. The electronic device 2600 can communicate information, such as sensor measurements or hydration condition information, to the computing device 2620. In one example, the computing device 2620 can process and/or analyze the sensor measurements and/or information received from the electronic device 2600. In another example, the computing device 2620 can send processed data, analyzed data, measurement results, and/or other information to the electronic device 2600. In another example, the computing device 2620 can communicate calibration information to the electronic device 2610.

Figure 27:
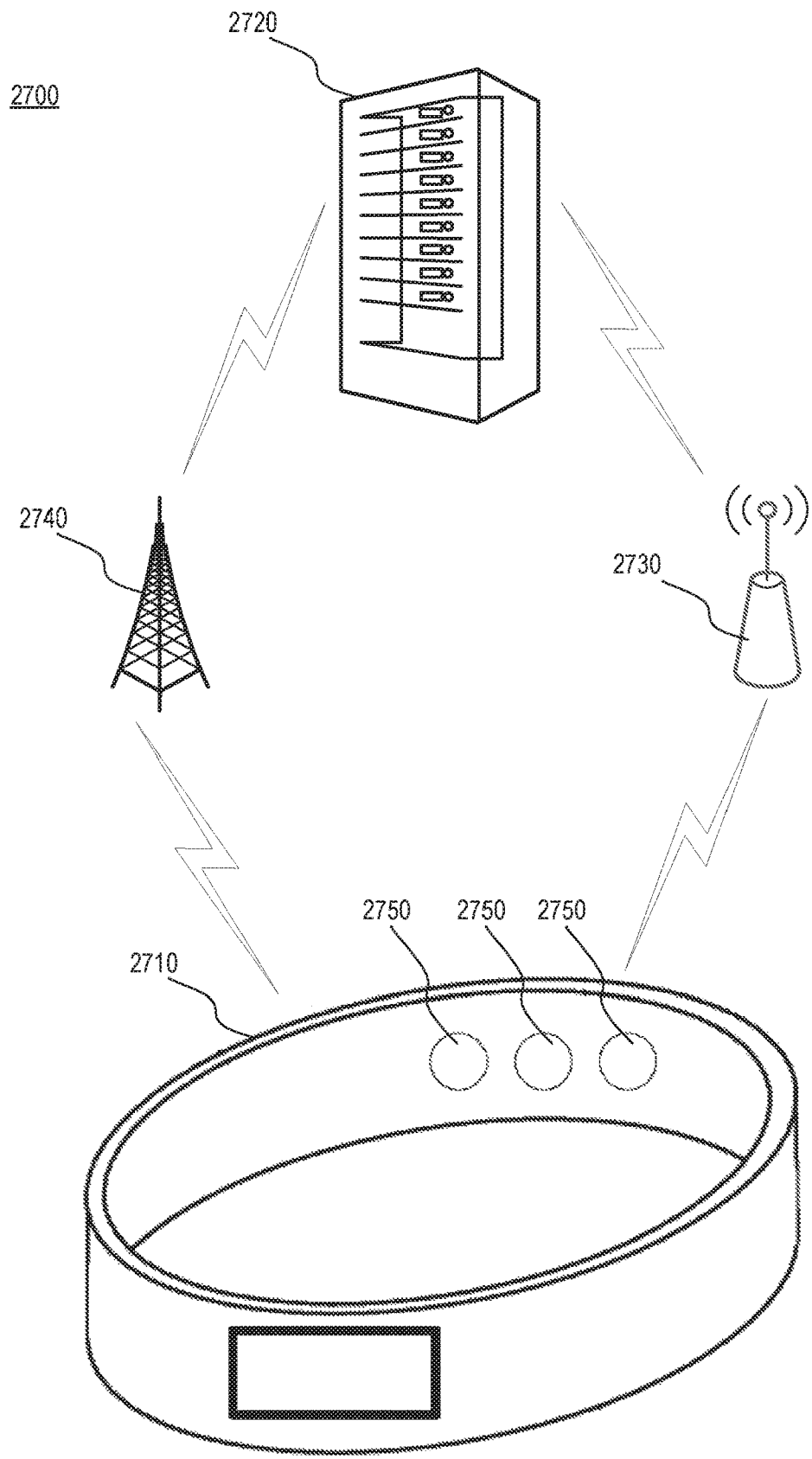
FIG. 27 illustrates an electronic device and a computing device in indirect communication using a communications network, according to one embodiment.

FIG. 27 illustrates an electronic device 2700 and a computing device 2720 in indirect communication using a communications network, according to one embodiment. In one embodiment, the electronic device 2700 can be a standalone device with a processing device to analyze or process: information taken from one or more sensors 2750 of the electronic device 2700; information received from other devices; and/or information stored in a memory of the electronic device 2700.

In another embodiment, the electronic device 2700 communicates locally with the computing device 2720 use a wireless communication network 2730 or a cellular communication network 2740. The local computing device 2720 can be a smartphone, tablet device, personal computer, laptop, a local server, and so forth. In another embodiment, the electronic device 2700 communicates with a non-local or remote computing device 2720 using a wireless communication network 2730 or a cellular communication network 2740. The non-local or remote computing device 2720 can be a remote server, a cloud-based server, a back-end server, or other remote electronic devices.

In one example, the wireless communication network 2730 is a cellular network employing a third generation partnership project (3GPP®) release 8, 9, 10, 11, or 12 or Institute of Electronics and Electrical Engineers (IEEE®) 802.16p, 802.16n, 802.16m-2011, 802.16h-2010, 802.16j-2009, 802.16-2009. In another example, the electronic device 2700 may provide a secure wireless area network (WLAN), secure PAN, or Private Wide Area Network (PWAN) to communicate with the computing device 2720. The electronic device 2700 in the WLAN may use the WI-FI® technology and IEEE® 802.11 standards defined by the WI-FI ALLIANCE® such as the IEEE® 802.11-2012, IEEE® 802.11ac, or IEEE® 802.11ad standards. Alternatively, the electronic device 2700 and the computing device 2720 in the WLAN may use other technologies and standards. Similarly, the electronic device 2710 in the PAN or WPAN may use a BLUETOOTH® technology and IEEE® 802.15 standards defined by the BLUETOOTH® Special Interest Group, such as BLUETOOTH® v1.0, BLU- ETOOTH® v2.0, BLUETOOTH® v3.0, or BLUETOOTH® v4.0 (including BLUETOOTH® low energy). Alternatively, the electronic device 2700 in the secure PAN may use other technologies and standards. In another embodiment, the communications network may be a ZIGBEE® connection developed by the ZIGBEE® Alliance such as IEEE® 802.15.4-2003 (ZIGBEE® 2003), IEEE® 802.15.4-2006 (ZIGBEE® 2006), IEEE® 802.15.4-2007 (ZIGBEE® Pro). The WAN or PWAN can be used to transmit data over long distances and between different LANs, WLANs, metropolitan area networks (MANs), or other localized computer networking architectures.

The electronic device 2700 and the computing device 2720 can be in indirect communication using a communications network such as wireless communication network 2730 (such as a network using WI-FI® technology) and/or using a cellular communication network 2740 (e.g., a network using 3rd Generation Partnership Project (3GPP®), and so forth) to communicate data or measurement information. In one example, the electronic device 2700 can take sensor measurements using sensors 2750 and communicate the sensor measurements to the computing device 2720 via the wireless communication network 2730 and/or the cellular communication network 2740. In another example, the computing device 2720 can receive sensor measurements from the electronic device 2700 via the wireless communication network 2730 and/or the cellular communication network 2740 and process the sensor measurements and/or analyze the sensor measurements. When the computing device 2720 has processed the sensor measurements and/or analyzed the sensor measurements, the computing device 2720 can communicate the processed sensor measurements, analyzed sensor measurements, sensor measurement results, or other information to the electronic device 2700 via the wireless communication network 2730 and/or the cellular communication network 2740.

FIG. 28 illustrates body area network (BAN) devices 2862-2876 communicating using a BAN, according to one embodiment. In one embodiment, the BAN can include a wired body area network, a wireless body area network (WEAN), and/or a body sensor network (BSN). The BAN can include multiple wearable computing devices or wearable sensor devices 2862-2876 that are in communication with each other to send and receive data and information. In one example, the BAN devices can include: a BAN device 2860 that is attached or coupled to the body of the user; an BAN device 2862 that is implanted into the body of the user; a BAN device 2868 that is embedded into the body of a user; a BAN device 2870 that is mounted on a surface of the body, and so forth. In another example, the BAN devices can include devices adjacent the user including: a BAN device 2864 shaped to fit in a clothes pockets of the user, a BAN device 2866 that a user can carry, such as a handheld device; a BAN device 2872 that is integrated into clothes of the user; a BAN device 2876 located in a user's bag, a BAN device 2874 integrated into a user's bag, and so forth. In one embodiment, an electronic device is a BAN device. In another embodiment, the BAN devices 2862-2876 can be body sensor units (BSUs) that include a processing device, a sensor, and a communication device. The BSUs can communicate with a body central unit (BCU) 2878 that is a hub for the BAN devices. The BCU 2878 can be located at any of the locations discussed above for the BAN devices 2862-2876. The BCU 2878 can include a processing device, memory, a communication device, and a display. The BCU 2878 can receive data from a BAN device 2862-2876 and analyze the data. In one example, the BCU 2878 can display the analyzed data using the display of the BCU 2878. In another example, the BCU 2878 can send the analyzed data to a BAN device 2862-2876 or another device. In one embodiment, the BAN devices 2862-2878 can be configured to be minimal sensor devices with low power consumption and a compact design where the BCU 2878 performs the processing of the data.

In another embodiment, the BCU 2878 can be a data hub or data gateway to manage the BAN devices 2862-2876. In another embodiment, the BCU 2878 can provide a user interface to control the BAN devices 2862-2876. In another embodiment, the BAN devices 2862-2876 and/or the BCU 2878 can use wireless private area networks (WPAN) technology as a gateway or relay to reach longer ranges. In one example, the BCU 2878 can us a WPAN to connect the BAN device 2862-2876 on the body to the internet. For example, medical professionals can access patient data from the BAN devices 2862-2876 online using the internet independent of a location of a patient.

Figure 29:
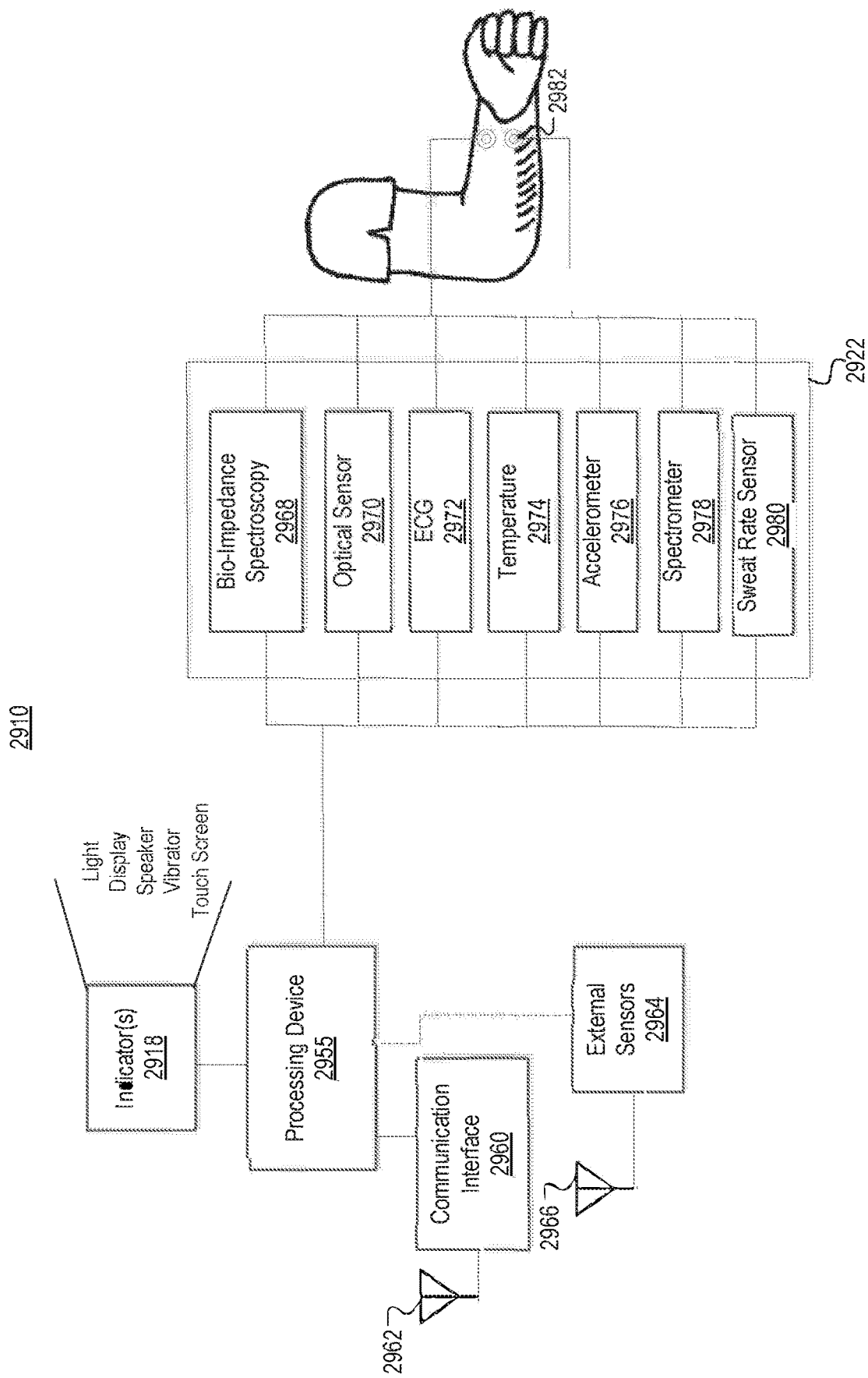
FIG. 29 illustrates a schematic view of an electronic device, according to one embodiment

FIG. 29 illustrates a schematic view of an electronic device 2910, according to one embodiment. The electronic device 2910 may include the indicators 2918, a sensor array 2922 (to include at least one of the sensors in FIG. 1, 2, 4, 5, or 7), a processing device 2955, a communications interface 2960, an antenna 2962 coupled with the communications interface 2960, external sensors 2964, and accompanying antenna(s) 2966. In one example, the sensor array 2922 may include one or more physiological sensors to take physiological measurements (e.g., measurements related to the body of the user or animal). The sensor array 2922 may include one or more sensors to engage a user of the electronic device to take measurements. In various examples, the sensor array 2922 may include, without limitation: a bioimpedance spectroscopy sensor 2968 (or simply impedance sensor 2968), an optical sensor 2970, an electrocardiogram (ECG) sensor 2972, a temperature sensor 2974 (such as a thermometer or thermistor), an accelerometer 2976, a spectrometer 2978, a sweat rate sensor 2980, and so forth. In one example, the sensor array 2922 can contact or engage the body of the user at a location 2982.

Figure 30:
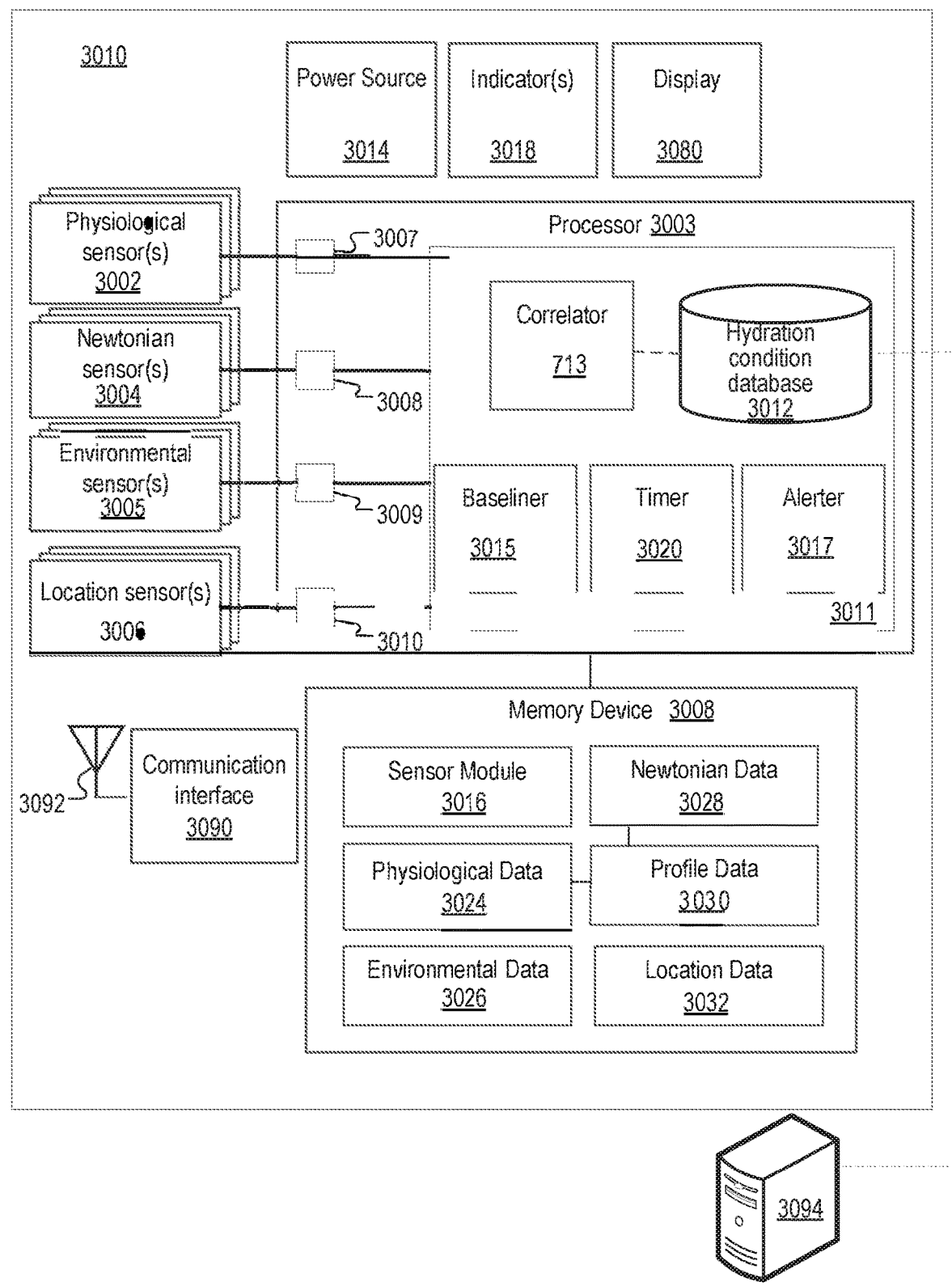
FIG. 30 is a block diagram of an electronic device with a correlator, a baseliner, and an alerter, according to one embodiment.

FIG. 30 illustrates a block diagram of the electronic device 3010 with a correlator 3013, a baseliner 3015, and an alerter 3017, according to one embodiment. The electronic device 3010 may include, without limitation, one or more physiological sensor(s) 3002, one or more Newtonian sensor(s) 3004, one or more environmental sensor(s) 3005, one or more location sensor(s) 3004, a processing device 504, a memory device 3008, a display 3080, a communication interface 1090 (such as a radio frequency (RF) circuit), and an antenna 3092 coupled to the communication interface 3090.

In one embodiment, the communication interface 3090 may communicate, via the antenna 3092, with an external electronic device 2590 (illustrated in FIG. 25), a computing device 1320 or 1420 (illustrated in FIGS. 13 and 14), and with other wireless devices such as electronic device 3010 of other users. In one example, the communication interface 3090 may communicate the information using a cellular network, a wireless network, or a combination thereof. In one example, the communications network can be a cellular network employing a third generation partnership project (3GPP) release 8, 9, 10, 11, or 12 or Institute of Electronics and Electrical Engineers (IEEE®) 802.16p, 802.16n, 802.16m-2011, 802.16h-2010, 802.16j-2009, 802.16-2009. In another example, the electronic device 3010 may provide a secure wireless area network (WLAN), secure PAN, or private wireless Wide Area Network (WAN) to communicate with a device. The electronic device 3010 in the WLAN may use the WI-FI® technology and IEEE® 802.11 standards defined by the WI-FI ALLIANCE® such as the IEEE® 802.11-2012, IEEE® 802.11ac, or IEEE® 802.11ad standards. Alternatively, the devices in the WLAN may use other technologies and standards. Similarly, the electronic device 3010 in the PAN or WPAN may use the BLUETOOTH® technology and IEEE® 802.15 standards defined by the BLUETOOTH® Special Interest Group, such as BLUETOOTH® v1.0, BLUETOOTH® v2.0, BLUETOOTH® v3.0, or BLUETOOTH® v4.0. Alternatively, the electronic device 3010 in the secure PAN may use other technologies and standards. In another embodiment, the communications network may be a ZIGBEE® connection developed by the ZIGBEE® Alliance such as IEEE® 802.15.4-2003 (ZIGBEE® 2003), IEEE® 802.15.4-2006 (ZIGBEE® 2006), IEEE® 802.15.4-2007 (ZIGBEE® Pro). The WAN or PWAN can be used to transmit data over long distances and between different LANs, WLANs, metropolitan area networks (MANs), or other localized computer networking architectures.

In one embodiment, the electronic device 3010 can communicate data with the other devices via another device, such as a smartphone or tablet computing device. For example, the communication interface 3090 can pair with a smartphone via the wireless network. The smartphone can receive data using the wireless network and can communicate the data to the other device. In another embodiment, the electronic device 3010 may communicate information with the other device via repeaters or a relay system. For example, a user of the electronic device 3010 can be outside a coverage area for the cellular network or the wireless network, e.g., a farm worker out in the field. In this example, the electronic device 3010 can determine that it is outside the coverage area and switch to communicating via the repeaters or the relay system.

In one embodiment, the electronic device 3010 can determine it is outside a coverage area when it does not receive a signal from the cellular network or the wireless network. In another embodiment, the electronic device 3010 can ping the cellular network or the wireless network (such as a tower within the cellular network or the wireless network) and determine that it is outside the coverage area when the electronic device 3010 does not receive a reply to the ping. In another embodiment, multiple electronic devices 3010 can communicate with each other to form a piconet. In this embodiment, a first electronic device can determine it is outside the coverage area and can scan for a second electronic device, where the second electronic device is in the coverage area or in communication with another electronic device in the coverage area. When the first wearable safety finds the second electronic device, the electronic device can communicate information to an end device or to the cellular network or the wireless network via the second electronic device.

The processor 3003 may include a first sensor interface 3007 for receiving sensor data from the physiological sensor(s) 3002, a second sensor interface 3008 for receiving sensor data from the Newtonian sensor(s) 3004, a third sensor interface 3009 for receiving sensor data from the environmental sensor(s) 3005, a fourth sensor interface 3010 for receiving sensor data from the location sensor(s) 3006, and a processing element 3011. The processing element 3011 in turn may include a correlator 3013, a baseliner 3015 and/or an alerter 3017. The memory device 3008 may also include, without limitation, a sensor module 3016, physiological data 3024, environmental data 3026, Newtonian data 3028, and profile data 3030, location data 3032.

The electronic device 3010 may include the sensor array 120 (FIG. 1) with two or more sensors. In the depicted embodiment, the electronic device 3010 may include one or more physiological sensors 3002, one or more Newtonian sensors 3004, one or more environmental sensors 3005, one or more location sensors 3006, or a combination thereof. In some instances, the Newtonian sensors 3004 may be physiological sensors. That is, in some embodiment, the activity level may be determined from one or more physiological measurements.

A physiological measurement may be any measurement related to a living body, such as a human's body or an animal's body. The physiological measurement is a measurement made to assess body functions. Physiological measurements may be simple, such as the measurement of body or skin temperature, or they may be more complicated, for example measuring how well the heart is functioning by taking an ECG (electrocardiograph) or determining a hydration condition of the body. Physiological measurements may also include motion and/or movement of the body. In some cases, these physiological measurements may be taken as an aggregate, e.g., as physiological data, with which to correlate to other physiological measurements, a physiological parameter, and/or an environmental parameter.

A parameter may be considered a measurable quantity (such as heart rate, temperature, altitude, and oxygen level, as just a few examples). When measurements of parameters are taken in the aggregate, the measurements may form data which may be analyzed and correlated to other data or parameters, to identify trends or to identify when meeting (or exceeding) certain thresholds that trigger alerts or other actions and the like.

The physiological sensors 3002 may include a pulse oximeter sensor, an electrocardiography (ECG) sensor, a fluid level sensor, an oxygen saturation sensor, a body core temperature sensor, a skin temperature sensor, a plethysmograph sensor, a respiration sensor, a breath rate sensor, a cardiac sensor (e.g., a blood pressure sensor, a heart rate sensor, a cardiac stress sensor, or the like), an impedance sensor (e.g., bio-impedance spectroscopy sensor), an optical sensor, a spectrographic sensor, an oxygen saturation sensor, or humidity and/or temperature sensors. Alternatively, other types of sensors may be used to measure physiological measurements, including measurements to determine activity levels of a person wearing the electronic device.

The Newtonian sensors 3004 may be any of the physiological sensors described above, but in some cases, the Newtonian sensors 3004 are activity or motion sensors, such as, for example, a gyroscope sensor, a vibration sensor, an accelerometer sensor (e.g., a sensor that measures acceleration and de-acceleration), a three dimensional (3D) accelerometer sensor (e.g., sensors that measure the acceleration and de-acceleration and the direction of such acceleration and de-acceleration), a force sensor, a pedometer, a strain gauge, a magnetometer, and a geomagnetic field sensor that may be used for activity level measurements; whereas the physiological sensors 3002 may be used for specific physiological measurements.

In one embodiment, an environmental measurement may be any measurement of an area approximate or adjacent a user. The environmental sensors 3005 may be a humidity sensor, an ambient temperature sensor, an altitude sensor, a barometer, and so forth. A location measurement may be any measurement of a location of the user or a movement of the user. The location sensor 3006 may be a global positioning system (GPS), a triangulation system, or a location sensor. One or a combination of the physiological data 3024, the environmental data 3026, the Newtonian data 3028, the profile data 3030, and the location data 3032 may be obtained from other sources such as through the network 1230 or 1240 from sources reachable in the cloud or online.

In another embodiment, the environmental measurement can be any measurement of a local or central location measurement of where a user is located. For example, one or more environmental sensors 3005 may be located at a location within a threshold radius of the user, such as a threshold radius from the user location. In this example, the environmental sensors 3005 can take environmental measurements and relay the information to the electronic device 3010 or to a communication hub that has a communication channel established with the electronic device 3010. Alternatively, the environmental sensors 3005 can take environmental measurements and relay the information to a processing hub that can analyze the environmental measurements to determine selected environmental factors (such as a humidity level, a heat index, and so forth) and can communicate the environmental factors to the electronic device 3010 or to another electronic device. In another embodiment, the processing hub can receive the environmental measurements from the environmental sensors 3005 and other measurements (such as physiological measurements) from the electronic device 3010. The processing hub can analyze the environmental measurements and the other measurements to determine selected result data, such as a hydration level of a user or a health level of the user. In another embodiment, the electronic device 3010 can take a first set of environmental measurements and the local environmental sensors 3005 can take a second set of environmental measurements. The first set of environmental measurements and the set of environmental measurements can be combined or aggregated and the processing hub and/or the electronic device 3010 can analyze the aggregated environmental measurements.

In another embodiment, the environmental measurements can be from an environmental information outlet or provider. For example, the environmental information outlet or provider is a weather station, a news station, a television station, an online website, and so forth. The electronic device 3010 or the processing hub can receive the environmental information from the environmental information outlet or provider can use the environmental information to determine selected physiological and/or environmental data or factors.

The first sensor interface 3007 may be coupled with the one or more physiological sensors 3002, a second sensor interface 3009 may be coupled with the one or more Newtonian sensors 3004, a third sensor interface 3009 may be coupled with the one or more environmental sensors 3005, and a fourth sensor interface 3010 may be coupled with the one or more location sensors 3006. The processing element 3011 may be operable to execute one or more instructions stored in the memory device 3008, which may be coupled with the processor 3003. In some cases, the processing element 3011 and memory device 3008 may be located on a common substrate or on a same integrated circuit die. Alternatively, the components described herein may be integrated in one or more integrated circuits as would be appreciated by one having the benefit of this disclosure. The memory device 3008 may be any type of memory device, including non-volatile memory, volatile memory, or the like. Although not separately illustrated the memory device may be one or more types of memory configured in various types of memory hierarchies.

The memory device 3008 may store physiological data 3024, such as current and past physiological measurements, as well as profile data 3030, including user profile data, bibliographic data, demographic data, and the like. The physiological data 3024, and in some cases the profile data 3030, may also include processed data regarding the measurements, such as statistical information regarding the measurements, as well as data derived from the measurements, such as predictive indicators, results, and/or recommendations.

In one example, the profile data 3030 may also include information connected to user profiles of the users that wear the electronic device 3010, such as a gender of the user, an age of the user, a body weight or mass of the user, a health status of the user, a fitness level of the user, or a family health history of the user. In another example, the profile data 3030 can include occupational information of the users that wear the electronic device 3010, such as a job type, a job title, whether the job is performed indoors or outdoors, a danger level of the job, and so forth. For example, the job types can include an elderly live-at-home job, an oil driller, a construction worker, a railroad worker, a coal mine worker, a job in confined spaces, a fireman, a construction worker, an outdoor worker, an office worker, a truck driver, a child, or a disabled individual.

In one example, the electronic device 3010 can receive the profile data 3030 via a touch screen device integrated into the electronic device 3010 or coupled to the electronic device 3010. In another example, the electronic device 3010 can receive the profile data 3030 via a communication port of the electronic device 3010. For example, the electronic device 3010 can receive profile data 3030 from another device via a wired communication connection (e.g., a universal serial bus) or via a wireless communication connection (e.g., a BLUETOOTH® communication technology).

The profile data 3030 may also be linked to various physiological data 3024 and Newtonian data 3028 and be tracked over time for the users. The profile data 3030 may also include baselines of physiological parameters for respective users. In one example, the baselines are of a heart rate, a blood pressure, bio-impedance, skin temperature, oxygen levels, hydration levels, electrolyte levels and so forth. When the baselines are included with the user profiles, the user profiles may be referred to as baseline profiles for the respective users.

The memory device 3008 may also store one or a combination of the environmental data 3026, the Newtonian data 3028, the profile data 3030, and the location data 3032. The Newtonian data 3028, environmental data 3026, or location data 3032 may be current and past measurements, as well predictive data for predictive modeling of activity levels, environmental levels, or locations. The memory device 3008 may store instructions of the sensor module 3016 and instructions and data related to the correlator 3013, the base liner 3015 and the alerter 3017, which perform various operations described below.

In particular, the sensor module 3016 may perform operations to control the physiological sensors 3002, Newtonian sensors 3004, environmental sensors 3005, and location sensors 3006, such as when to turn them on and off, when to take a measurement, how many measurements to take, how often to perform measurements, and so forth. For example, the sensor module 3016 may be programmed to measure a set of physiological measurements according to a default pattern or other adaptive patterns to adjust when and how often to take certain types of measurements. The measurements may be stored as the physiological data 3024, the environment data 3026, and the Newtonian data 3028, location data 3032, and some of them may also be integrated as a part of the profile data 3030, as discussed.

In the depicted embodiment, the processing element 3007 (e.g., one or more processor cores, a digital signal processor, or the like) executes the instructions of the sensor module 3016 and those related to the correlator 3013, the baseliner 3015, the alerter 3017 and possibly other modules or routines. Alternatively, the operations of the sensor module 3016 and the correlator 3013, the baseliner 3015, and the alerter 3017 may be integrated into an operating system that is executed by the processor 3003. In one embodiment, the processing element 3011 measures a physiological measurement via the first sensor interface 3007. The processing element 3011 may measure an amount of activity of the electronic device 3010 via the second sensor interface 3009. The amount of activity could be movement or motion of the electronic device 3010 (e.g., by tracking location), as well as other measurements indicative of the activity level of a user, such as heart rate, body temperature, skin luminosity, or the like. The processing element 3011 measures an environmental measurement via the third sensor interface 3009. The processing element 3011 measures a location measurement via the fourth sensor interface 3010.

In one embodiment, the Newtonian sensors 3004 may include a hardware motion sensor to measure at least one of movement or motion of the electronic device 3010. The processing element 3011 may determine the amount of activity based the movement or motion of the electronic device 3010. The hardware motion sensor may be an accelerometer sensor, a gyroscope sensor, a magnetometer, a GPS sensor, a location sensor, a vibration sensor, a 3D accelerometer sensor, a force sensor, a pedometer, a strain gauge, a magnetometer, and a geomagnetic field sensor.

The processor 3003 may further execute instructions to facilitate operations of the electronic device 3010 that receive, store and analyze measurement data, environmental data, location data, and profile data. The indicator(s) 3018 may include one or more of a light, a display, a speaker, a vibrator, and a touch display, useable to alert the user to take actions in response to trending levels of: physiological parameters during or after physical activity and/or prepare for undertaking anticipated physical activity; environmental parameters; activity parameters, or location parameters.

In some embodiments, for example, the correlator 3013 may analyze measurement data to correlate physiological data, environmental data, activity data, location data, or user experienced feedback with a physiological parameter, environmental parameter, activity parameter, a location parameter, or user experienced feedback to predict a change in a level of the physiological parameter, environmental parameter, activity parameter, or a location parameter. In one embodiment, the user experienced feedback can be physiological or psychological symptoms experienced by the user. For example, the physiological or psychological symptoms can include: headaches, dizziness, tiredness, mental fatigue, increased thirst, dry mouth, swollen tongue, physical weakness, confusion, sluggishness, and so forth.

Such prediction may enable timely and accurate recommendations to a user in terms of hydrating, adjusting effort levels or other specific actions to address a trend or a change in the physiological parameter, the environmental parameter, the activity parameter, or the location parameter. The recommendations may be displayed in the display 3080, sent via an alert through one of the indictor(s) 3018 or displayed in another device such as a smart phone or tablet or other computing device.

In another embodiment, the correlator 3013 may also track and analyze Newtonian data of the user related to physiological or determined parameters (such as heart rate, oxygenation, skin luminosity, hydration, and the like), related to location and type of activity (such as activity levels associated with being at the gym, riding a bike, attending class, working at a desk, sleeping, or driving in traffic, and the like) and/or related to scheduling information (such as appointments on a calendar, invites received from friends, or messages related to travel and/or activity plans, and the like). Through this analysis, the electronic device 3010 may track activity data over time, intelligently and continuously (or periodically) analyze all of this information and alert the user through the indicator(s) 3018 to take a specific action at a proper time before a start of a dehydration condition. The specific action may include to hydrate extra hours before physical activity and to eat at least two hours before any physical activity, or other such timing that may be general to most users or customized to a training or nutrition routine of a specific user.

In another embodiment, the correlator 3013 can build an individualized profile for the user. The correlator 3013 can receive the individualized profile information from an input device of the electronic device 3010. For example, the correlator 3013 can receive the individualized profile information from a touch screen of the electronic device 3010. In another example, the correlator 3013 can receive the individualized profile information from a device in communication with the electronic device (such as via a USB port or using a BLUETOOTH® technology). In another embodiment, the electronic device 3010 can include a memory that stores the individualized profile information for the user.

The individualized profile can include physiological information associated with the user. For example, the physiological information can include a hydration condition, an average heart rate of the user, an age of the user, a health level of the user, and so forth. The individualized profile can also include information associated with a location or environment that the user is located. For example, the individualized profile can include: humidity level information, such as when the user is located in a dry climate or in a humid climate; altitude level information, such as when the user is located at a relatively high altitude or a relatively low altitude; seasonal information, such as if it is winter where the user is located or summer. The correlator 3013 can also determine an environmental effect on the user for the location where the user is located at. For example, if the user is located at their home that is at a high altitude with a dry climate and it is a winter season, the correlator 3013 can determine that the user is acclimated to high altitudes, dry climates, and the winter season. The correlator 3013 can also update the user profile when the user changes location. For example, when the user leaves their home location and goes on a vacation to a location that is at a low altitude, a humid climate, and it is a summer season, the correlator 3013 can determine that the user is not acclimated to the low altitude, humid climate, and summer season.

In one embodiment, the electronic device 3010 can alert the user of the changes to the individualized profile. In another embodiment, the electronic device 3010 can alert the user of the changes to effects associated with the changes to the individualized profile. For example, the electronic device 3010 can access a table of predetermine effects of the user changing their user profile. In one example, the table can indicate that when the user switches from a low altitude to a high-altitude location, the user may experience altitude sickness. In another example, the table can indicate that when the user switches from a dry climate to a humid climate location, an ability of the user's body to cool itself down when an ambient temperature is relatively high. In another embodiment, the table can indicate when the current user profile indicates safety risks or physiological performance changes.

In another embodiment, the individualized profile can also include information associated with clothing or apparel worn by the user of the electronic device 3010. For example, the individualized profile can indicate that a user may wear different types of apparel for different environments including: a thickness of fabric; a type of a fabric, such as wool or cotton; a number of clothes layers worn by the client; accessories worn by the client, such as hard hats, steeled toed shoes, safety googles, safety belts, and so forth; and gender types of apparel, such as women and men's apparel. In one example, the correlator can adjust measurement information or measurement results based on the different types of clothing or apparel. For example, the correlator 3013 can determine that the user is a firefighter and is wearing multiple layers of clothing to protect against fire. In this example, the correlator 3013 can determine that a cause of a hydration level of the user decreasing is the multiple layers of clothing cause the firefighter to sweat more and loss more fluid than a typical number of layers of clothing worn by the user.

In one embodiment, the alerter 3017 may decide the most appropriate timing and mode of alert, whether through one of the indicator(s) 3018, the display 3080 or another device such as a smart phone, tablet or the like. The type of indicator used to alert the user may also be customized to or by the user.

In one embodiment, the correlator 3013 may determine a correlation between different data points or data sets of the input data (such as data collected from different sensors, devices, or obtained from the cloud or online). The correlator 3013 may determine different types of correlations of the data points or data sets. In one example, the correlator 3013 may execute a Pearson product moment correlation coefficient algorithm to measure the extent to which two variables of input data may be related. In another example, the correlator 3013 may determine relations between variables of input data based on a similarity of rankings of different data points. In another example, the correlator 3013 may use a multiple regression algorithm to determine a correlation between a data set or a data point that may be defined as a dependent variable and one or more other data sets or other data points defined as independent variables. In another example, the correlator 3013 may determine a correlation between different categories or information types in the input data.

In further examples, when the correlator 3013 determines a correlation between the different data points or data sets, the correlator 3013 may use the correlation information to predict when a first event or condition may occur based on a second event or condition occurring. In another example, when the correlator 3013 determines a correlation between the different data points or data sets, the correlator 3013 may use the correlation information to determine a hydration condition. As discussed in the preceding paragraphs, a hydration can be an event that negatively impacts a user's safety or health. In another example, when the correlator 3013 determines a correlation between the different data points or data sets, the correlator 3013 may use the correlation information to determine a cause of a condition and/or event, such as a hydration condition.

Additionally, or alternatively, the correlator 3013 may determine a correlation between physiological data 3024, environmental data 3026, Newtonian data 3028, profile data 3030, and location data 3032. For example, the input data may include hydration level data (physiological data) and ambient temperature data (environmental data). In this example, the correlator 3013 may identify a correlation between an increase in the ambient temperature, a decrease in a hydration level of a user, and a heat stroke. The correlator 3013 may identify the correlation between the ambient temperature, the hydration level, and the heat stroke by using a regression algorithm with the heat stroke as an independent variable and the ambient temperature and the hydration level as dependent variables. When the correlator 3013 has identified the correlation between the heat stroke, the ambient temperature, and the hydration level, the correlator 3013 may predict a heat stroke based on a change in a hydration level of a user or a rate of change of a hydration level of a user and a change in the ambient temperature or a rate of change in the ambient temperature.

Additionally, or alternatively, the correlator 3013 may determine a correlation between a fatigue event, an altitude level, and an oxygenation level of a user. For example, the correlator 3013 may determine a correlation between an increase in the altitude level, a decrease in the oxygenation level of the user, and an increase in a fatigue event. When the correlator 3013 determines the correlation between the altitude level, the oxygenation level, and the fatigue event, the correlator 3013 may predict an increase or decrease in a probability of a hydration condition change based on a change in the oxygenation level of user and the altitude level at which the user is currently at. In one example, the correlator 3013 can use the individualized profile information (as discussed in the preceding paragraphs) of the user to determine the predicted increase or decrease in the probability of a hydration condition change. For example, the correlator 3013 can determine a change in altitude level of the user from a relatively low altitude to a relatively high altitude. The correlator 3013 can use the individualized profile information to determine that the user is acclimated to the relatively high altitude (such as if they live at a high altitude) and adjust the predicted increase or decrease in the probability of a hydration condition change for the change in altitude in view of the individualized profile information. For example, the correlator 3013 can predict that the change from the low altitude to the high altitude will not increase or decrease the probability of a user becoming dehydrated.

In a further example, the correlator 3013 may identify a correlation between location information and physiological data of a user. For example, the correlator 3013 may determine a location of a user for at a period of time, such as by using GPS sensor data or triangulation sensor data. In this example, the correlator 3013 may receive physiological measurement data (such as heart rate measurement data, optical spectroscopy data, hydration level measurement data, blood pressure measurement data, and so forth). The correlator 3013 may correlate the location of the user with the physiological measurement data to increase an accuracy of data analysis, a diagnosis, or result data and/or provide additional details regarding a cause of a change in a hydration condition.

In one example, the correlator 3013 may determine that a user is at work in an office location. When the correlator 3013 detects an increase in a heart rate or a blood pressure of a user, the correlator 3013 may correlate heart rate or blood pressure data and the location information to determine a cause of the cognitive ability reduction event. For example, when a heart rate or blood pressure of a user increases while at a work in an office, the correlator 3013 may determine that the heart rate or blood pressure increase may be due to psychological causes (such as stress) rather than physiological causes (such as exercising or working out) because the user is at a location where the user is not likely to physically exert himself or herself.

In another example, the correlator 3013 may determine an occupation of the user, such as by using the profile data 3030. In one embodiment, the correlator 3013 can determinate that the occupation of the user is a higher risk occupation (e.g., a statistically more dangerous occupation). For example, the correlator 3013 can access a database or list (stored at the memory device 3008 or externally) that includes information associated with an occupation, such as environmental exposure. When the correlator 3013 detects that the occupation of the user is a higher risk occupation (e.g., an occupation with a risk level that exceeds a threshold value), the correlator 3013 may correlate heart rate data, blood pressure data, hydration level data, with the occupational information to determine a cause of a hydration condition change. For example, when a heart rate and blood pressure of a user increases and a hydration level of the individual decreases while the individual is working at an oil refinery or on a farm, the correlator 3013 may determine that the heart rate or blood pressure increase may be due to physiological influences of the occupation (such as strenuous labor or no breaks) rather than psychological causes (such as stress) because the occupation where the individual is working at is likely to include physical exertion.

In a further example, the correlator 3013 may use a multiple regression algorithm to determine a correlation between multiple data points or data sets and a hydration condition. For example, the correlator 3013 may receive heart rate data, skin temperature, bio-impedance data, skin luminosity and hydration level data of a user. In this example, the correlator 3013 may determine a correlation between these types of physiological data and a dehydration event of the individual. For example, the physiological data could be from optical spectroscopy (skin luminosity) and/or bio-impedance data. The correlator 3013 may then determine that as the bioimpedance of a user increases and skin luminosity decreases, a probability of a dehydration event occurring increases.

Additionally, or alternatively, the correlator 3013 may filter out a correlation determination (e.g., a determination that data points or data sets and a hydration condition may be correlated) when a correlation level is below a threshold level. For example, when the correlator 3013 determines that there may be a 30 percent correlation between a skin temperature or a bio-impedance level of a user and a fall event, the correlator 3013 may filter out or disregard the correlation information when determining a cause of the fall event. In another example, the correlator 3013 can use a learning algorithm or machine learning to determine when to filter out a correlation determination. For example, at a first instance of a fall, there may be a 30 percent correlation between a skin temperature or a bio-impedance level of a user and a fall event The correlator 3013 can monitor multiple fall events and use machine learning to determine that the initial 30 percent correlation is actually a 60 percent correlation and adjust the filter to not filter out the correlation between the skin temperature or the bio-impedance level of a user and a fall event or assign the correlation of the skin temperature or the bio-impedance level of a user and a fall event a different weight.

Additionally, or alternatively, the correlator 3013 may filter out the correlation determination based on a schedule of a user. For example, when the correlator 3013 determines that a user is taking a lunch break, off of work, or sleeping, the correlator 3013 may filter out environmental conditions that are associated with the occupation of the user, e.g., the correlator 3013 can filter out false positives.

Additionally, or alternatively, the correlator 3013 may discount or weight a correlation determination based on the correlation level of the correlation determination. For example, when the correlator 3013 determines that there may only be a 30 percent correlation between an occupation of a user and a hydration level of a user, the correlator 3013 may discount or assign a lower weight to the correlation determination (relative to a higher correlation percentage such as 90 percent) when determining a change in hydration condition.

Additionally, or alternatively, the correlator 3013 may assign weights to different factors, such as: physiological data 3024 (e.g., different types or qualities of physiological parameters), environmental data 3026 (e.g., different types or quality of environmental parameters), Newtonian data 3028 (e.g., different types or quality of Newtonian parameters), profile data 3030, location data 3032 (e.g., different types or quality of location parameters), a time of day, and so forth. In one example, the correlator 3013 may assign a first weight to hydration level data of a user and a second weight to profile data of a user when determining a probability of a change in hydration condition for a user. In this example, when determining the probability of a change in a hydration condition, the correlator 3013 may assign a higher weight to the hydration level data relative to the profile data, for example.

The correlator 3013 may additionally, or alternatively, use predetermined weights for the physiological data 3024, environmental data 3026, Newtonian data 3028, profile data 3030, and location data 3032. In another example, the correlator 3013 may receive user defined or predefined weights from an input device indicating the weights for the different physiological and/or environmental data. In another example, the correlator 3013 may determine the weights to assign to the physiological data 3024, environmental data 3026, Newtonian data 3028, profile data 3030, and location data 3032 based on correlation levels of the physiological data 1024, environmental data 3026, Newtonian data 3028, profile data 3030, and location data 3032. For example, when a correlation level between a hydration condition and a heart rate of a user may be relatively low over a threshold period of time and/or under a threshold number of different conditions, the correlator 3013 may assign a low weight to heart rate data when determining a cause of a change in hydration condition.

In one example, the correlator 3013 may assign different weights to one or more of the physiological data 3024, environmental data 3026, Newtonian data 3028, profile data 3030, and location data 3032 based on other physiological data 3024, environmental data 3026, Newtonian data 3028, profile data 3030, and location data 3032. For example, based on a location of a user, the correlator 3013 may assign a first weight to environmental data 3026 and a second weight to profile data 3030. In another example, the correlator 3013 may assign weights to different hydration conditions.

Additionally, or alternatively, the correlator 3013 may use environmental data 1726 or location data 3032 to determine a cause of a change in hydration condition. For example, when a user is located at a fitness facility working out, the correlator 3013 may increase a weight for a physical exertion related a change in a hydration condition occurring because of in physical exertion of a user (such as an increase in a heart rate or decrease in a hydration level of a user). In another example, when a user is located at home in bed resting or sleeping, the correlator 3013 may correlate a location of the user with the hydration condition of the user. In this example, the correlator 3013 may determine that a decrease in probability of a change in a hydration condition occurring due to a user being is located in their bedroom for a threshold period of time (e.g., a safer environment).

In one embodiment, the correlator 3013 can determine a weighting of measurement information or physiological information using medical evaluation information. In one example, the medical evaluation information includes medical evaluation information of the user, such as a medical physical. The medical evaluation information can include: medical history and health history information, such as whether the user is a smoker or a non-smoker; a user's blood pressure information; hereditary diseases information; a user's sexual health information; a user's dietary information, a user's exercise routine information, such as how often the user exercises; a user's heart or lung examine information; and so forth. In one example, the correlator 3013 can use the medical evaluation information to set initial weight for different data types. The correlator can update or adjust the weights for the different data types using machine learning. For example, the physiological data 3024, environmental data 3026, and Newtonian data 3028 is assigned a first set of weights based on the medical evaluation information. As the electronic device 3010 uses the sensors to collect the physiological data 3024, environmental data 3026, and the Newtonian data 3028, the correlator 3013 can use the physiological data 3024, the environmental data 3026, and the Newtonian data 3028 to customize the weighting of the measurement information or physiological information to the individual. For example, the correlator 3013 can receive medical evaluation information for the user input device of the electronic device 3010 using an input device of the electronic device 3010.

The correlator 3013 may track, sort and/or filter input data. The input data may include: user schedule information, such as a daily schedule of the user; survey information, such as information received from surveys of individuals; research information, such as clinical research information or academic research information associated with one or more hydration conditions of the electronic device; and so forth.

The correlator 3013 may use location-based tracking and/or scheduling information of the user in determining an expected or probable change in a hydration condition. For example, when a user is a member of a sports team, the user's schedule may include practice schedule information and/or game schedule information. In this example, the correlator 3013 may use the schedule information to anticipate that the user may be participating in physical activity and increase a probability that a change in hydration condition may occur.

The correlator 3013 may use timer information determining an expected or probable occurrence of a change in a hydration condition. For example, the correlator can monitor how long it may have been since a user took a break or consumed water. In this example, as the length of time increase between a break or water consumption, the probability that a change in hydration condition may occur increases. In another example, the correlator can use the timer information to periodically request a response from the user. For example, when a change in hydration condition has not occur within a threshold amount of time that would trigger a user response, the electronic device can request a user response from the user when the threshold amount of time has been exceeded.

In another example, the correlator 3013 can have a work mode (the user is at work) and a home mode (the user is at home), where a type of environmental condition that the electronic device monitors for and/or a probability of a change in a hydration condition occurring can increase or decrease when switching between the work mode and the home mode. For example, when the user has a high risk occupation, the correlator 3013 can monitor for change in hydration condition related to the high risk occupation when the correlator is in a work mode and switch to monitoring for changes in a hydration condition related to low risk activities when the correlator is in a home mode.

In another example, the correlator 3013 may use the scheduling information in correlation with a location of the user to determine an expected or probable change in a hydration condition. For example, the scheduling information may indicate that the user may be scheduled to attend a lecture at a physical fitness facility and the correlator 3013 may adjust the types or probabilities of a change in a hydration condition occurring in view of the scheduling information. In this example, while the correlator 3013 may typically increasing a probability of a change in hydration condition occurring for the user in anticipation of physical activity based on the location information (e.g., the physical fitness facility), the correlator 3013 may adjust the adjust the types or probabilities of a change in a hydration condition occurring in view of the scheduling information that the user may be attending a lecture rather than working out.

Additionally, or alternatively, the correlator 3013 may track and update activity levels of users and correlate these levels with hydration conditions over time. For example, the GPS sensor of the electronic device 3010 may indicate that the user usually works out at the gym on Monday, Wednesday and Friday at 7 a.m. and goes on a long bike ride on Saturday, usually starting about 8:30a.m. Although these activities may not be available within the scheduling information or data of the electronic device 3010 (or other tethered device), the correlator 3013 may execute machine learning to add to a user's activity data these events that normally occur.

The electronic device 3010 may store historical or previous hydration condition information of the user. In one example, the correlator 3013 may store the historical information on the memory device 3008 of the electronic device 3010. In another example, the correlator 3013 may use the communication device 170 (illustrated in FIG. 1), the communication unit 2570 (illustrated in FIG. 25), or the communication interface 3090 to store the hydration condition information on a memory device coupled to or in communication with the electronic device, such as a cloud-based storage device or a memory device of another computing device. In another example, the correlator 3013 may be part of a cloud-based system or the other computing device, as will be discussed in more detail with reference to FIGS. 26 and 27.

The correlator 3018 may filter and/or sort hydration condition information. In one example, the correlator 3018 may receive a filter or sort command from the electronic device or an input device to filter and/or sort the hydration information. In another example, the filter or sort command may include filter parameters and/or sort parameters.

In another example, the correlator 3013 may sort and/or filter the input data based on a trending of hydration conditions. For example, the correlator 3013 may sort hydration conditions that may be trending in an increasing direction or a decreasing direction and may sort the hydration conditions based on the trending. In this example, different hydration conditions for a user may be trending in different directions, such as a dehydration events of a user may be increasing in trending and fall events may be stable or stagnant.

In another embodiment, the baseliner 3015 may receive profile information from a new user to include any or a combination of gender, age, weight, health, fitness level, and family health histories. The health and fitness levels of the user may be based at least in part on physiological measurements received from the physiological sensor(s) 3002 and the activity data received from the Newtonian sensors 3004. The baseliner 3015 may then identify, from one or more baseline profiles of other users (e.g., a group of users), a baseline profile that is most similar to the user profile based on a correlation between the user profile information and baseline profile information. The baseline profiles can include baseline information of a probability of a change in hydration conditions occurring for a user. The user profiles can include information of the types of hydration conditions that may be probable to occur for user.

The baseliner 3015 may then be able to set a baseline against which to judge a hydration condition. In an alternate embodiment, the baseline profile that is most similar to the user profile is identified from an aggregated baseline profile for one or more individuals corresponding to the one or more baseline profiles. Alternatively, or additionally, the most similar profiles may look at a hydration condition that occurs for the individual as compared to a group. For example, the user may be most similar to another individual because they both react physiologically similarly to hot temperatures outside. In another example, the user may have a similar dehydration profile to the most-similar profile, meaning, when the user works out the user may reach a dehydration level at a certain point in time that substantially matches the timing of the most-similar profile.

The electronic device 3010 may further receive survey information and/or research information from an input device with which to build or add to the user and/or baseline profiles. For example, the electronic device 3010 may receive survey information that includes: gender information, age information, physical weight information, general health information, family information, fitness level information, and so forth. In one example, the correlator 3013 may determine a correlation between the survey information and user input data. For example, the correlator 3013 may correlate the age, weight, fitness level, and general health level of a user with survey information from other individuals to determine a correlation between the survey information for the individual and the other individuals. In this example, the baseliner 3015 may set a baseline for a measurement of the electronic device 3010 for the individual based on baselines for the other individuals with the same or similar survey information.

In another example, the correlator 3013 may correlate the user information with research information (such as research papers, clinical studies, and so forth). For example, the electronic device may retrieve research information related to a physiological parameter, the correlator 3013 may then correlate the research information with hydration conditions for the user to generate a research correlation. The baseliner 3015 may then adjust the baseline set for the user related to the hydration conditions in response to the research correlation.

The correlator 3013 can store hydration condition information in a hydration condition database 3012. In one embodiment, the correlator 3013 can determine parameters associated with hydration conditions. The parameters can include threshold values for measurements or data values, such as physiological sensor measurements, environmental sensor measurements, Newtonian sensor measurements, location sensor measurements, or profile data 3030. The correlator 3013 can store the hydration condition and the associated hydration parameters in the hydration condition database 3012. For example, the correlator 3013 can determine that parameters for a heat stroke event can be a skin temperature above a 100-degree temperature, blood pressure above 150 systolic, and a bio-impedance level above 15000 ohms (e.g., a dehydration level threshold). In this example, the correlator 3013 can determine these parameters can store the hydration condition with the associated parameters in the hydration condition database 3012. In another example, the store predetermined hydration conditions with the associated parameters. In another example, the hydration condition database 3012 can receive the hydration conditions and the associated parameters from another device or server 3094.

The preceding examples are intended for purposes of illustration and are not intended to be limiting. The correlator 3013 may identify a correlation between various data points, data sets, data types, and/or hydration conditions. After having a correlation that informs, for example, a heat stroke event, the hydration level, and/or oxygenation level of the user, and further in consideration of a present activity level of the user, the alerter 3017 may alert the user at the proper time when to hydrate or how to moderate activity levels to avoid or minimize a dehydrated condition.

Figure 31:
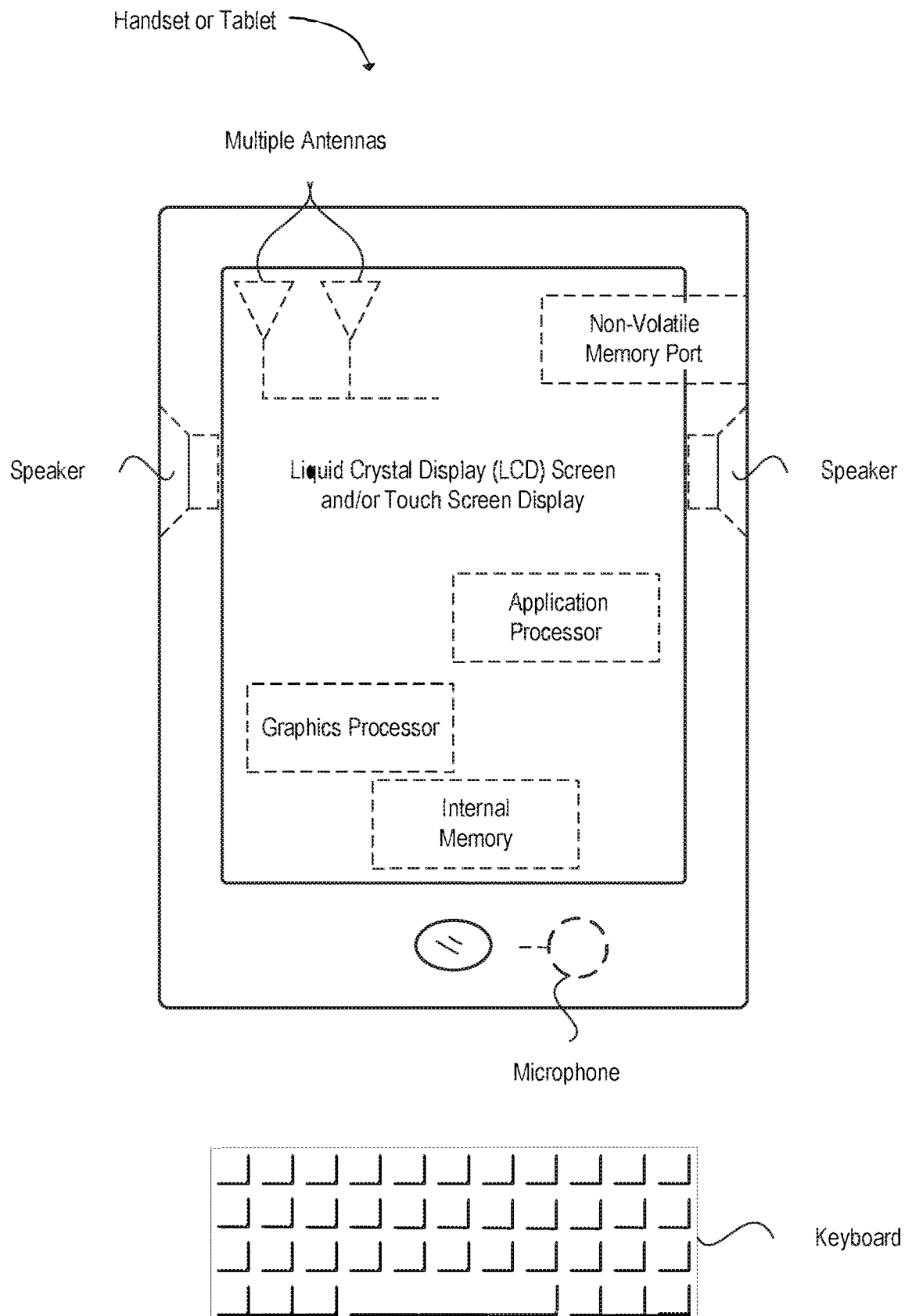
FIG. 31 is an example illustration of a processing device disclosed herein, such as a user equipment (UE), a base station, an electronic device (LIVID), a mobile wireless device, a mobile communication device, a tablet, a handset, or other type of wireless device, according to one embodiment.

FIG. 31 illustrates an example illustration of a processing device disclosed herein, such as user equipment (UE), a base station, an electronic device (UMD), a mobile wireless device, a mobile communication device, a tablet, a handset, or other type of wireless device, according to one embodiment. The device may include one or more antennas configured to communicate with a node or transmission station, such as a base station (BS), an evolved Node B (eNode B), a baseband unit (BBU), a remote radio head (RRH), a remote radio equipment (RRE), a relay station (RS), a radio equipment (RE), a remote radio unit (RRU), a central processing module (CPM), or other type of wireless wide area network (WWAN) access point. The device may be configured to communicate using at least one wireless communication standard including 3GPP® LTE, WiMAX, High Speed Packet Access (HSPA), BLUETOOTH®, and WI-FI®. The device may communicate using separate antennas for each wireless communication standard or shared antennas for multiple wireless communication standards. The device may communicate in a wireless local area network (WLAN), a wireless personal area network (WPAN), and/or a WWAN.

FIG. 31 also provides an illustration of a microphone and one or more speakers that may be used for audio input and output from the device. The display screen may be a liquid crystal display (LCD) screen, or other type of display screen such as an organic light emitting diode (OLED) display. The display screen may be configured as a touch screen. The touch screen may use capacitive, resistive, or another type of touch screen technology. An application processor and a graphics processor may be coupled to internal memory to provide processing and display capabilities. A non-volatile memory port may also be used to provide data input/output options to a user. The non-volatile memory port may also be used to expand the memory capabilities of the wireless device. A keyboard may be integrated with the wireless device or wirelessly connected to the wireless device to provide additional user input. A virtual keyboard may also be provided using the touch screen.

Various techniques, or certain embodiments or portions thereof, may take the form of program code (i.e., instructions) embodied in tangible media, such as floppy diskettes, CDROMs, hard drives, non-transitory computer readable storage medium, or any other machine-readable storage medium where, when the program code is loaded into and executed by a machine, such as a computer, the machine becomes an apparatus for practicing the various techniques. In the case of program code execution on programmable computers, the computing device may include a processor, a storage medium readable by the processor (including volatile and non-volatile memory and/or storage elements), at least one input device, and at least one output device. The volatile and non-volatile memory and/or storage elements may be a RAM, EPROM, flash drive, optical drive, magnetic hard drive, or other medium for storing electronic data. The base station and mobile station may also include a transceiver module, a counter module, a processing module, and/or a clock module or timer module. One or more programs that may implement or utilize the various techniques described herein may use an application programming interface (API), reusable controls, and the like. Such programs may be implemented in a high-level procedural or object oriented programming language to communicate with a computer system. However, the program(s) may be implemented in assembly or machine language. In any case, the language may be a compiled or interpreted language, and combined with hardware implementations.

It should be understood that many of the functional units described in this specification have been labeled as modules, in order to more particularly emphasize their implementation independence. For example, a module may be implemented as a hardware circuit including custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, include one or more physical or logical blocks of computer instructions, which may, for instance, be organized as an object, procedure, or function. Nevertheless, the executables of an identified module need not be physically located together but may include disparate instructions stored in different locations which, when joined logically together, include the module and achieve the stated purpose for the module.

Indeed, a module of executable code may be a single instruction, or many instructions, and may even be distributed over several different code segments, among different programs, and across several memory devices. Similarly, operational data may be identified and illustrated herein within modules and may be embodied in any suitable form and organized within any suitable type of data structure. The operational data may be collected as a single data set or may be distributed over different locations including over different storage devices, and may exist, at least partially, merely as electronic signals on a system or network. The modules may be passive or active, including agents operable to perform specific functions.

Reference throughout this specification to "an example" means that a particular feature, structure, or characteristic described in connection with the example is included in at least one embodiment of the present disclosure. Thus, appearances of the phrases "in an example" in various places throughout this specification are not necessarily all referring to the same embodiment.

As used herein, one or more items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present disclosure may be referred to herein along with alternatives for the various components thereof. It is understood that such embodiments, examples, and alternatives are not to be construed as de facto equivalents of one another but are to be considered as separate and autonomous representations of the present disclosure.

Furthermore, the described features, structures, or characteristics may be combined in any suitable manner in one or more embodiments. In the foregoing description, numerous specific details are provided, such as examples of layouts, distances, network examples, and so forth, to provide a thorough understanding of embodiments of the disclosure. One skilled in the art will recognize, however, that the disclosure may be practiced without one or more of the specific details, or with other methods, components, layouts, and so forth. In other instances, well-known structures, materials, or operations are not shown or described in detail to avoid obscuring embodiments of the disclosure.

While the foregoing examples are illustrative of the principles of the present disclosure in one or more particular applications, it will be apparent to those of ordinary skill in the art that numerous modifications in form, usage and details of implementation may be made without the exercise of inventive faculty, and without departing from the principles and concepts of the disclosure. Accordingly, it is not intended that the disclosure be limited, except as by the claims set forth below.

Figure 32:
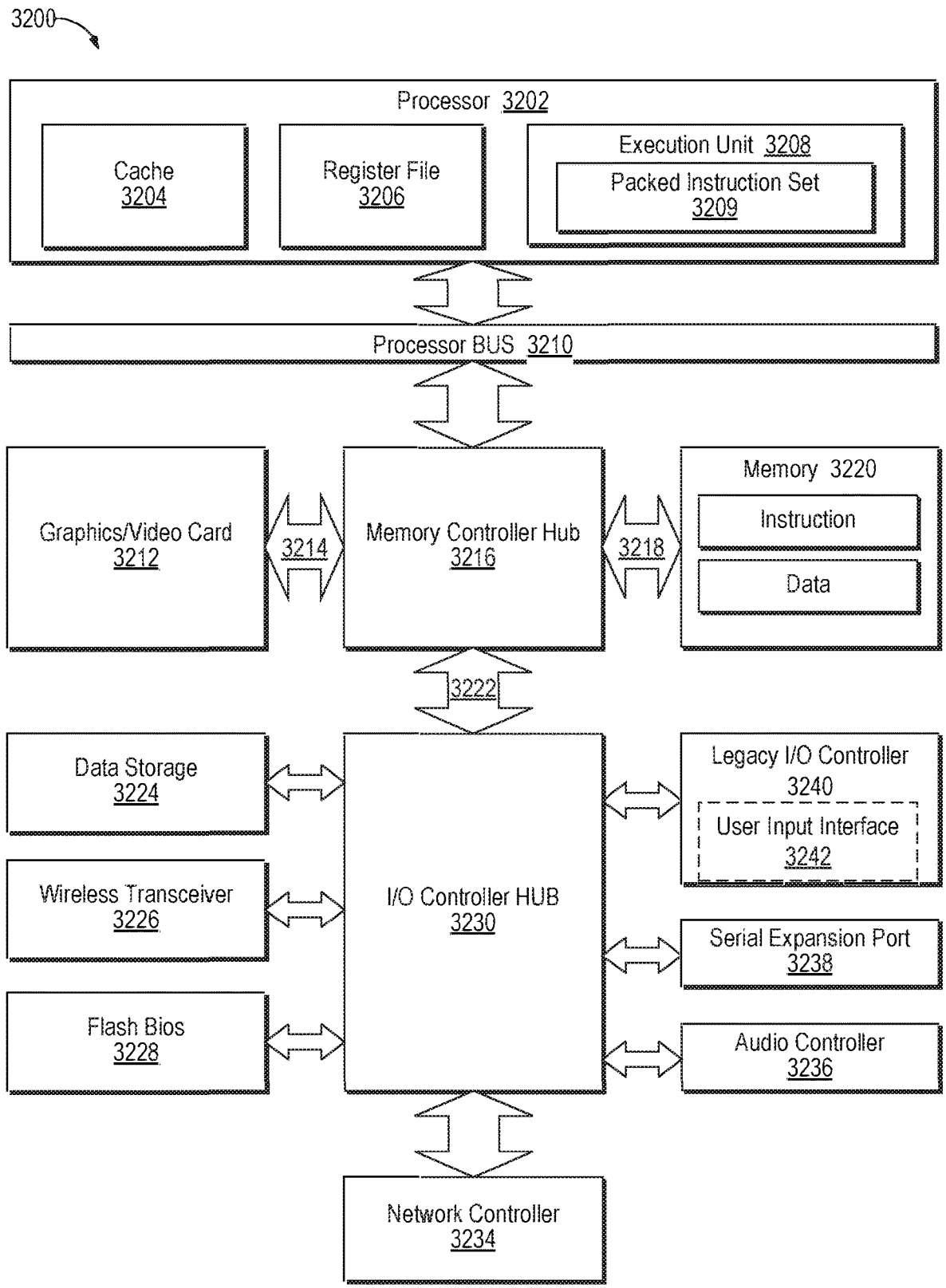
FIG. 32 is a block diagram of an exemplary computer system formed with a processor that includes execution units to execute an instruction, where one or more of the interconnects implement one or more features in accordance with one example implementation of the present disclosure is illustrated.

FIG. 32, a block diagram of an exemplary computer system formed with a processor that includes execution units to execute an instruction, where one or more of the interconnects implement one or more features in accordance with one example implementation of the present disclosure is illustrated, according to one embodiment. System 3200 includes a component, such as a processor 3202 to employ execution units including logic to perform algorithms for process data, in accordance with the present disclosure, such as in the example implementation described herein. System 3200 is representative of processing systems based on the PENTIUM® III, PENTIUM® 4, XEON®, Itanium, XSCALE™ and/or STRONGARM™ microprocessors available from Intel Corporation of Santa Clara, Calif., although other systems (including PCs having other microprocessors, engineering workstations, set-top boxes and the like) may also be used. In one example implementation, sample system 3200 executes a version of the WINDOWS® operating system available from Microsoft Corporation of Redmond, Wash., although other operating systems (UNIX and Linux for example), embedded software, and/or graphical user interfaces, may also be used. Thus, example implementations of the present disclosure are not limited to any specific combination of hardware circuitry and software.

Example implementations are not limited to computer systems. Alternative example implementations of the present disclosure can be used in other devices such as handheld devices and embedded applications. Some examples of handheld devices include cellular phones, Internet Protocol devices, digital cameras, personal digital assistants (PDAs), and handheld PCs. Embedded applications can include a micro controller, a digital signal processor (DSP), system on a chip, network computers (NetPC), set-top boxes, network hubs, wide area network (WAN) switches, or any other system that can perform one or more instructions in accordance with at least one example implementation.

Alternative example implementations of the present disclosure can be used in other devices, such as an electronic device. The electronic device may be connected (e.g., networked) to other machines in a LAN, an intranet, an extranet, or the Internet. The electronic device may operate in the capacity of a server or a client device in a client-server network environment, or as a peer device in a peer-to-peer (or distributed) network environment. The electronic device may be a personal computer (PC), a tablet PC, a set-top box (STB), a cellular telephone, a smartphone, a web appliance, a server, a network router, switch or bridge, or any electronic device capable of executing a set of instructions (sequential or otherwise) that specify actions to be taken by that electronic device. Further, while only a single electronic device is illustrated, the term "electronic device" shall also be taken to include any collection of electronic devices that individually or jointly execute a set (or multiple sets) of instructions to perform any one or more of the methodologies discussed herein.

The system 3200 may correspond to the processing device 150 (illustrated in FIG. 1), the processing device 504 (illustrated in FIG. 5), the controller 1080 (illustrated in FIG. 10), the processing device 1455 (illustrated in FIG. 14), or the processor 1503 (illustrated in FIG. 15). The system 3200 may correspond to at least a portion of a cloud-based computer system.

In this illustrated example implementation, processor 3202 includes one or more execution units 3208 to implement an algorithm that is to perform at least one instruction. One example implementation may be described in the context of a single processor desktop or server system, but alternative example implementations may be included in a multiprocessor system. System 3200 is an example of a 'hub' system architecture. The computer system 3200 includes a processor 3202 to process data signals. The processor 3202, as one illustrative example, includes a complex instruction set computer (CISC) microprocessor, a reduced instruction set computing (RISC) microprocessor, a very long instruction word (VLIW) microprocessor, a processor implementing a combination of instruction sets, or any other processor device, such as a digital signal processor, for example. The processor 3202 is coupled to a processor bus 3210 that transmits data signals between the processor 3202 and other components in the system 3200. The elements of system 3200 (e.g. graphics accelerator 3212, memory controller hub 3216, memory 3220, 1/0 controller hub 3224, wireless transceiver 3226, Flash BIOS 3228, Network controller 1334, Audio controller 3236, Serial expansion port 3238, 1/0 controller 3240, and so forth) perform their conventional functions that are well known to those familiar with the art.

In one example implementation, the processor 3202 includes a Level 1 (L1) internal cache memory 3204. Depending on the architecture, the processor 3202 may have a single internal cache or multiple levels of internal caches. Other example implementations include a combination of both internal and external caches depending on the particular implementation and needs. Register file 3206 is to store different types of data in various registers including integer registers, floating point registers, vector registers, banked registers, shadow registers, checkpoint registers, status registers, and instruction pointer register.

Execution unit 3208, including logic to perform integer and floating-point operations, also resides in the processor 3202. The processor 3202, in one example implementation, includes a microcode (ucode) ROM to store microcode, which when executed, is to perform algorithms for certain macroinstructions or handle complex scenarios. Here, microcode is potentially updateable to handle logic bugs/fixes for processor 3202. For one example implementation, execution unit 3208 includes logic to handle a packed instruction set 3209. By including the packed instruction set 3209 in the instruction set of a general-purpose processor 3202, along with associated circuitry to execute the instructions, the operations used by many multimedia applications may be performed using packed data in a general-purpose processor 3202. Thus, many multimedia applications are accelerated and executed more efficiently by using the full width of a processor's data bus for performing operations on packed data. This potentially eliminates the need to transfer smaller units of data across the processor's data bus to perform one or more operations, one data element at a time.

Alternate example implementations of an execution unit 3208 may also be used in micro controllers, embedded processors, graphics devices, DSPs, and other types of logic circuits. System 3200 includes a memory 3220. Memory 3220 includes a dynamic random-access memory (DRAM) device, a static random access memory (SRAM) device, flash memory device, or other memory device. Memory 3220 stores instructions and/or data represented by data signals that are to be executed by the processor 3202.

A system logic chip 3216 is coupled to the processor bus 3210 and memory 3220. The system logic chip 3216 in the illustrated example implementation is a memory controller hub (MCH). The processor 3202 can communicate to the MCH 3216 via a processor bus 3210. The MCH 3216 provides a high bandwidth memory path 3218 to memory 3220 for instruction and data storage and for storage of graphics commands, data and textures. The MCH 3216 is to direct data signals between the processor 3202, memory 3220, and other components in the system 1300 and to bridge the data signals between processor bus 3210, memory 3220, and system 1/0 3222. In some example implementations, the system logic chip 3216 can provide a graphics port for coupling to a graphics controller 3212. The MCH 3216 is coupled to memory 3220 through a memory interface 3218. The graphics card 3212 is coupled to the MCH 3216 through an Accelerated Graphics Port (AGP) interconnect 3214.

System 3200 uses a proprietary hub interface bus 3222 to couple the MCH 1316 to the 1/0 controller hub (ICH) 3230. The ICH 3230 provides direct connections to some 1/0 devices via a local 1/0 bus. The local 1/0 bus is a high-speed 1/0 bus for connecting peripherals to the memory 3220, chipset, and processor 3202. Some examples are the audio controller, firmware hub (flash BIOS) 3228, wireless transceiver 3226, data storage 3224, legacy 1/0 controller containing user input and keyboard interfaces, a serial expansion port such as Universal Serial Bus (USB), and a network controller 3234. The data storage device 3224 can include a hard disk drive, a floppy disk drive, a CD-ROM device, a flash memory device, or other mass storage device.

For another example implementation of a system, an instruction in accordance with one example implementation can be used with a system on a chip. One example implementation of a system on a chip includes of a processor and a memory. The memory for one such system is a flash memory. The flash memory can be located on the same die as the processor and other system components. Additionally, other logic blocks such as a memory controller or graphics controller can also be located on a system on a chip.

In the following description, numerous specific details are set forth, such as examples of specific types of processors and system configurations, specific hardware structures, specific architectural and micro architectural details, specific register configurations, specific instruction types, specific system components, specific measurements/heights, specific processor pipeline stages and operation and so forth in order to provide a thorough understanding of the present disclosure. It will be apparent, however, to one skilled in the art that these specific details need not be employed to practice the present disclosure. In other instances, well known components or methods, such as specific and alternative processor architectures, specific logic circuits/code for described algorithms, specific firmware code, specific interconnect operation, specific logic configurations, specific manufacturing techniques and materials, specific compiler implementations, specific expression of algorithms in code, specific power down and gating techniques/logic and other specific operational details of computer system haven't been described in detail in order to avoid unnecessarily obscuring the present disclosure.

Although the following example implementations may be described with reference to energy conservation and energy efficiency in specific integrated circuits, such as in computing platforms or microprocessors, other example implementations are applicable to other types of integrated circuits and logic devices. Similar techniques and teachings of example implementations described herein may be applied to other types of circuits or semiconductor devices that may also benefit from better energy efficiency and energy conservation. For example, the disclosed example implementations are not limited to desktop computer systems or ULTRA-BOOK®. And may be also used in other devices, such as handheld devices, tablets, other thin notebooks, systems on a chip (SOC) devices, and embedded applications. Some examples of handheld devices include cellular phones, Internet protocol devices, digital cameras, personal digital assistants (PDAs), and handheld PCs. Embedded applications typically include a microcontroller, a digital signal processor (DSP), a system on a chip, network computers (NetPC), set-top boxes, network hubs, wide area network (WAN) switches, or any other system that can perform the functions and operations taught below. Moreover, the apparatus', methods, and systems described herein are not limited to physical computing devices but may also relate to software optimizations for energy conservation and efficiency. As will become readily apparent in the description below, the example implementations of methods, apparatus', and systems described herein (whether in reference to hardware, firmware, software, or a combination thereof) are vital to a 'green technology' future balanced with performance considerations.

It is described that the system may be any kind of computer or embedded system. The disclosed embodiments may especially be used for electronic device, electronic implants, sensory and control infrastructure devices, controllers, supervisory control and data acquisition (SCADA) systems, or the like. Moreover, the apparatuses, methods, and systems described herein are not limited to physical computing devices but may also relate to software optimizations for energy conservation and efficiency. As will become readily apparent in the description below, the embodiments of methods, apparatuses, and systems described herein (whether in reference to hardware, firmware, software, or a combination thereof).

Although the following example implementations are described with reference to a processor, other example implementations are applicable to other types of integrated circuits and logic devices. Similar techniques and teachings of example implementations of the present disclosure can be applied to other types of circuits or semiconductor devices that can benefit from higher pipeline throughput and improved performance. The teachings of example implementations of the present disclosure are applicable to any processor or machine that performs data manipulations. However, the present disclosure is not limited to processors or machines that perform 512 bit, 256 bit, 128 bit, 64 bit, 32 bit, or 16 bit data operations and can be applied to any processor and machine in which manipulation or management of data is performed. In addition, the following description provides examples, and the accompanying drawings show various examples for the purposes of illustration. However, these examples should not be construed in a limiting sense as they are merely intended to provide examples of example implementations of the present disclosure rather than to provide an exhaustive list of all possible implementations of example implementations of the present disclosure.

Although the below examples describe instruction handling and distribution in the context of execution units and logic circuits, other example implementations of the present disclosure can be accomplished by way of a data or instructions stored on a machine-readable, tangible medium, which when performed by a machine cause the machine to perform functions consistent with at least one example implementation of the present disclosure. In one example implementation, functions associated with example implementations of the present disclosure are embodied in machine-executable instructions. The instructions can be used to cause a general-purpose or special-purpose processor that is programmed with the instructions to perform the steps of the present disclosure. Example implementations of the present disclosure may be provided as a computer program product or software which may include a machine or computer-readable medium having stored thereon instructions which may be used to program a computer (or other electronic devices) to perform one or more operations according to example implementations of the present disclosure. Alternatively, steps of example implementations of the present disclosure might be performed by specific hardware components that contain fixed-function logic for performing the steps, or by any combination of programmed computer components and fixed-function hardware components.

Instructions used to program logic to perform example implementations of the present disclosure can be stored within a memory in the system, such as DRAM, cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, Compact Disc, Read-Only Memory (CD-ROMs), and magneto-optical disks, Read-Only Memory (ROMs), Random Access Memory (RAM), Erasable Programmable Read-Only Memory (EPROM), Electrically Erasable Programmable Read-Only Memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, and so forth). Accordingly, the computer-readable medium includes any type of tangible machine-readable medium suitable for storing or transmitting electronic instructions or information in a form readable by a machine (e.g., a computer).

The embodiments of methods, hardware, software, firmware or code set forth above may be implemented via instructions or code stored on a machine-accessible, machine readable, computer accessible, or computer readable medium which are executable by a processing element. A non-transitory machine-accessible/readable medium includes any mechanism that provides (i.e., stores and/or transmits) information in a form readable by a machine, such as a computer or electronic system. For example, a non-transitory machine-accessible medium includes random-access memory (RAM), such as static RAM (SRAM) or dynamic RAM (DRAM); ROM; magnetic or optical storage medium; flash memory devices; electrical storage devices; optical storage devices; acoustical storage devices; other form of storage devices for holding information received from transitory (propagated) signals (e.g., carrier waves, infrared signals, digital signals); and so forth, which are to be distinguished from the non-transitory mediums that may receive information there from.

Instructions used to program logic to perform embodiments of the disclosure may be stored within a memory in the system, such as DRAM, cache, flash memory, or other storage. Furthermore, the instructions may be distributed via a network or by way of other computer readable media. Thus a machine-readable medium may include any mechanism for storing or transmitting information in a form readable by a machine (e.g., a computer), but is not limited to, floppy diskettes, optical disks, Compact Disc, Read-Only Memory (CD-ROMs), and magnetooptical disks, Read-Only Memory (ROMs), Random Access Memory (RAM), Erasable Programmable Read-Only Memory (EPROM), Electrically Erasable Programmable Read-Only Memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, and so forth). Accordingly, the computer-readable medium includes any type of tangible machine-readable medium suitable for storing or transmitting electronic instructions or information in a form readable by a machine (e.g., a computer)

The computer-readable storage medium may also be used to store instructions utilizing logic and/or a software library containing methods that call the above applications. While the computer-readable storage medium can be a single medium, the term "computer-readable storage medium" should be taken to include a single medium or multiple media (e.g., a centralized or distributed database, and/or associated caches and servers) that store the one or more sets of instructions. The term "computer-readable storage medium" shall accordingly be taken to include, but not be limited to, solid-state memories, optical media, and magnetic media.

A design may go through various stages, from creation to simulation to fabrication. Data representing a design may represent the design in a number of manners. First, as is useful in simulations, the hardware may be represented using a hardware description language or another functional description language. Additionally, a circuit level model with logic and/or transistor gates may be produced at some stages of the design process. Furthermore, most designs, at some stage, reach a level of data representing the physical placement of various devices in the hardware model. In the case where conventional semiconductor fabrication techniques are used, the data representing the hardware model may be the data specifying the presence or absence of various features on different mask layers for masks used to produce the integrated circuit. In any representation of the design, the data may be stored in any form of a machine readable medium. A memory or a magnetic or optical storage such as a disc may be the machine readable medium to store information transmitted via optical or electrical wave modulated or otherwise generated to transmit such information. When an electrical carrier wave indicating or carrying the code or design is transmitted, to the extent that copying, buffering, or re-transmission of the electrical signal is performed, a new copy is made. Thus, a communication provider or a network provider may store on a tangible, machine-readable medium, at least temporarily, an article, such as information encoded into a carrier wave, embodying techniques of example implementations of the present disclosure.

In modern processors, a number of different execution units are used to process and execute a variety of code and instructions. Not all instructions are created equal as some are quicker to complete while others can take a number of clock cycles to complete. The faster the throughput of instructions, the better the overall performance of the processor. In one embodiment, as many instructions may execute as fast as possible. However, there are certain instructions that have greater complexity and require more in terms of execution time and processor resources. For example, there are floating point instructions, load/store operations, data moves, and so forth.

As more computer systems are used in internet, text, and multimedia applications, additional processor support has been introduced over time. In one example implementation, an instruction set may be associated with one or more computer architectures, including data types, instructions, register architecture, addressing modes, memory architecture, interrupt and exception handling, and external input and output (110).

In one example implementation, the instruction set architecture (ISA) may be implemented by one or more microarchitectures, which includes processor logic and circuits used to implement one or more instruction sets. Accordingly, processors with different microarchitectures can share at least a portion of a common instruction set. For example, INTEL® PENTIUM® 4 processors, INTEL® CORE™ processors, and processors from Advanced Micro Devices, Inc. of Sunnyvale Calif. implement nearly identical versions of the x86 instruction set (with some extensions that have been added with newer versions) but have different internal designs. Similarly, processors designed by other processor development companies, such as ARM Holdings, Ltd., MIPS, or their licensees or adopters, may share at least a portion a common instruction set, but may include different processor designs. For example, the same register architecture of the ISA may be implemented in different ways in different microarchitectures using new or well-known techniques, including dedicated physical registers, one or more dynamically allocated physical registers using a register renaming mechanism (e.g., the use of a Register Alias Table (RAT), a Reorder Buffer (ROB) and a retirement register file. In one example implementation, registers may include one or more registers, register architectures, register files, or other register sets that may or may not be addressable by a software programmer.

In one example implementation, an instruction may include one or more instruction formats. In one example implementation, an instruction format may indicate various fields (number of bits, location of bits, and so forth) to specify, among other things, the operation to be performed and the operand(s) on which that operation is to be performed. Some instruction formats may be further broken defined by instruction templates (or sub formats). For example, the instruction templates of a given instruction format may be defined to have different subsets of the instruction format's fields and/or defined to have a given field interpreted differently. In one example implementation, an instruction is expressed using an instruction format (and, if defined, in a given one of the instruction templates of that instruction format) and specifies or indicates the operation and the operands upon which the operation will operate.

Scientific, financial, auto-vectorized general purpose, RMS (recognition, mining, and synthesis), and visual and multimedia applications (e.g., 2D/3D graphics, image processing, video compression/decompression, voice recognition algorithms and audio manipulation) may require the same operation to be performed on a large number of data items. In one example implementation, Single Instruction Multiple Data (SIMD) refers to a type of instruction that causes a processor to perform an operation on multiple data elements. SIMD technology may be used in processors that can logically divide the bits in a register into a number of fixed-sized or variable-sized data elements, each of which represents a separate value. For example, in one example implementation, the bits in a 64-bit register may be organized as a source operand containing four separate 16-bit data elements, each of which represents a separate 16-bit value. This type of data may be referred to as 'packed' data type or 'vector' data type, and operands of this data type are referred to as packed data operands or vector operands. In one example implementation, a packed data item or vector may be a sequence of packed data elements stored within a single register, and a packed data operand or a vector operand may a source or destination operand of a SIMD instruction (or 'packed data instruction' or a 'vector instruction'). In one example implementation, a SIMD instruction specifies a single vector operation to be performed on two source vector operands to generate a destination vector operand (also referred to as a result vector operand) of the same or different size, with the same or different number of data elements, and in the same or different data element order.

SIMD technology, such as that employed by the INTEL® CORE™ processors having an instruction set including x86, MMX™, Streaming SIMD Extensions (SSE), SSE2, SSE3, SSE4.1, and SSE4.2 instructions, ARM processors, such as the ARM CORTEX® family of processors having an instruction set including the Vector Floating Point (VFP) and/or NEON instructions, and MIPS processors, such as the Loongson family of processors developed by the Institute of Computing Technology (ICT) of the Chinese Academy of Sciences, has enabled a significant improvement in application performance (CORE® and MMX® are registered trademarks or trademarks of Intel Corporation of Santa Clara, Calif.).

In one example implementation, destination and source registers/data are generic terms to represent the source and destination of the corresponding data or operation. In some example implementations, they may be implemented by registers, memory, or other storage areas having other names or functions than those depicted. For example, in one example implementation, "DEST1" may be a temporary storage register or other storage area, whereas "SRC1" and "SRC2" may be a first and second source storage register or other storage area, and so forth. In other example implementations, two or more of the SRC and DEST storage areas may correspond to different data storage elements within the same storage area (e.g., a SIMD register). In one example implementation, one of the source registers may also act as a destination register by, for example, writing back the result of an operation performed on the first and second source data to one of the two source registers serving as a destination register.

A module as used herein refers to any combination of hardware, software, and/or firmware. As an example, a module includes hardware, such as a micro-controller, associated with a non-transitory medium to store code adapted to be executed by the micro-controller. Therefore, reference to a module, in one embodiment, refers to the hardware, which is specifically configured to recognize and/or execute the code to be held on a non-transitory medium. Furthermore, in another embodiment, use of a module refers to the non-transitory medium including the code, which is specifically adapted to be executed by the microcontroller to perform predetermined operations. And as may be inferred, in yet another embodiment, the term module (in this example) may refer to the combination of the microcontroller and the non-transitory medium. Often module boundaries that are illustrated as separate commonly vary and potentially overlap. For example, a first and a second module may share hardware, software, firmware, or a combination thereof, while potentially retaining some independent hardware, software, or firmware. In one embodiment, use of the term logic includes hardware, such as transistors, registers, or other hardware, such as programmable logic devices.

Use of the phrase 'configured to,' in one embodiment, refers to arranging, putting together, manufacturing, offering to sell, importing and/or designing an apparatus, hardware, logic, or element to perform a designated or determined task. In this example, an apparatus or element thereof that is not operating is still 'configured to' perform a designated task if it is designed, coupled, and/or interconnected to perform said designated task. As a purely illustrative example, a logic gate may provide a 0 or a 1 during operation. But a logic gate 'configured to' provide an enable signal to a clock does not include every potential logic gate that may provide a 1 or 0. Instead, the logic gate is one coupled in some manner that during operation the 1 or 0 output is to enable the clock. Note once again that use of the term 'configured to' does not require operation, but instead focus on the latent state of an apparatus, hardware, and/or element, where in the latent state the apparatus, hardware, and/or element is designed to perform a particular task when the apparatus, hardware, and/or element is operating.

Furthermore, use of the phrases 'to,' 'capable of/to,' and or 'operable to,' in one embodiment, refers to some apparatus, logic, hardware, and/or element designed in such a way to enable use of the apparatus, logic, hardware, and/or element in a specified manner. Note as above that use of to, capable to, or operable to, in one embodiment, refers to the latent state of an apparatus, logic, hardware, and/or element, where the apparatus, logic, hardware, and/or element is not operating but is designed in such a manner to enable use of an apparatus in a specified manner.

A value, as used herein, includes any known representation of a number, a state, a logical state, or a binary logical state. Often, the use of logic levels, logic values, or logical values is also referred to as 1's and 0's, which simply represents binary logic states. For example, a 1 refers to a high logic level and 0 refers to a low logic level. In one embodiment, a storage cell, such as a transistor or flash cell, may be capable of holding a single logical value or multiple logical values. However, other representations of values in computer systems have been used. For example, the decimal number ten may also be represented as a binary value of 1010 and a hexadecimal letter A. Therefore, a value includes any representation of information capable of being held in a computer system.

Moreover, states may be represented by values or portions of values. As an example, a first value, such as a logical one, may represent a default or initial state, while a second value, such as a logical zero, may represent a non-default state. In addition, the terms reset and set, in one embodiment, refer to a default and an updated value or state, respectively. For example, a default value potentially includes a high logical value, i.e. reset, while an updated value potentially includes a low logical value, i.e. set. Note that any combination of values may be utilized to represent any number of states.

Reference throughout this specification to "one embodiment" or "an embodiment" means that a particular feature, structure, or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

In the foregoing specification, a detailed description has been given with reference to specific exemplary embodiments. It will, however, be evident that various modifications and changes may be made thereto without departing from the broader spirit and scope of the disclosure as set forth in the appended claims. The specification and drawings are, accordingly, to be regarded in an illustrative sense rather than a restrictive sense. Furthermore, the foregoing use of embodiment and other exemplarily language does not necessarily refer to the same embodiment or the same example, but may refer to different and distinct embodiments, as well as potentially the same embodiment.

Some portions of the detailed description are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here and generally, conceived to be a self-consistent sequence of operations leading to a specific result. The operations are those requiring physical manipulations of physical quantities. Usually, though not necessarily, these quantities take the form of electrical or magnetic signals capable of being stored, transferred, combined, compared and otherwise manipulated. It has proven convenient at times, principally for reasons of common usage, to refer to these signals as bits, values, elements, symbols, characters, terms, numbers or the like. The blocks described herein may be hardware, software, firmware or a combination thereof.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "defining," "receiving," "determining," "issuing," "linking," "associating," "obtaining," "authenticating," "prohibiting," "executing," "requesting," "communicating," or the like, refer to the actions and processes of a computing system, or similar electronic computing device, that manipulates and transforms data represented as physical (e.g., electronic) quantities within the computing system's registers and memories into other data similarly represented as physical quantities within the computing system memories or registers or other such information storage, transmission or display devices.

The words "example" or "exemplary" are used herein to mean serving as an example, instance or illustration. Any embodiment or design described herein as "example" or "exemplary" is not necessarily to be construed as preferred or advantageous over other embodiments or designs. Rather, use of the words "example" or "exemplary" is intended to present concepts in a concrete fashion. As used in this application, the term "or" is intended to mean an inclusive "or" rather than an exclusive "or." That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such. Also, the terms "first," "second," "third," "fourth," and so forth as used herein are meant as labels to distinguish among different elements and may not necessarily have an ordinal meaning according to their numerical designation.

The invention claimed is:

1. A device, comprising:
   a band, wherein the band is shaped to fit around a body part comprising a muscular-walled tube of a user;
   a first physiological sensor coupled to the band and positioned to face a first location on the body part when the user wears the band;
   a second physiological sensor coupled to the band and positioned to face a second location on the body part when the user wears the band;
   a processor communicatively coupled to the first physiological sensor and the second physiological sensor, the processor operable to:
      take a first biometric measurement by the first physiological sensor;
      take a second biometric measurement by the second physiological sensor;

compare the first biometric measurement and the second biometric measurement to a baseline biometric measurement; and determine:
- a closest sensor to a defined position relative to the muscular-walled tube, wherein the closest sensor is either the first physiological sensor or the second physiological sensor based on the comparison; or
- the first physiological sensor and the second physiological sensor are equidistant from the defined position relative to the muscular-walled tube.

2. The device of claim 1, wherein the processor is further operable to determine a physiological condition based on the biometric measurement of:
- the closest sensor when the first physiological sensor and the second physiological sensor are determined to be not equidistant from the defined position relative to the muscular-walled tube; or
- the first physiological sensor or the second physiological sensor when the first physiological sensor and the second physiological sensor are determined to be equidistant from the defined position relative to the muscular-walled tube.

3. The device of claim 2, wherein when the biometric measurement comprises a current biometric measurement of the user, the processor is further operative to:
- obtain a previous biometric measurement;
- determine a change between the previous biometric measurement and the current biometric measurement;
- determine a time between the previous biometric measurement and the current biometric measurement; and
- determine a rate of change of an overall physiological condition based on the time and the change between the previous biometric measurement and the current biometric measurement.

4. The device of claim 1, wherein:
- the first physiological sensor comprises a first impedance pad; and
- the second physiological sensor comprises a second impedance pad.

5. The device of claim 1, wherein:
- the first physiological sensor comprises a first light source and a first optical sensor; and
- the second physiological sensor comprises a second light source and a second optical sensor.

6. The device of claim 5, wherein the processor is further operable to:
- take a first backscatter measurement by the first optical sensor from light emitted by the first light source and light emitted by the second light source;
- take a second backscatter measurement by the second optical sensor from light emitted by the first light source and light emitted by the second light source;
- aggregate the first backscatter measurement and the second backscatter measurement; and
- determine a physiological condition based on the aggregation of the first backscatter measurement and the second backscatter measurement.

7. The device of claim 1, wherein the processor is further operable to:
- aggregate the first biometric measurement and the second biometric measurement when it is determined the first physiological sensor and the second physiological sensor are equidistant from the muscular-walled tube; and
- determine a physiological condition based on the aggregation of the first biometric measurement and second biometric measurement.

8. The device of claim 1, wherein the second physiological sensor is separated from the first physiological sensor by a fixed distance such that when a signal is transmitted by the first physiological sensor, at least a portion of the signal is transmitted through the muscular-walled tube of the body part before being received by the second physiological sensor.

9. The device of claim 8, wherein the fixed distance is determined based on:
- a first size of the first physiological sensor;
- a second size of the second physiological sensor;
- a power of the signal received by the second physiological sensor; or
- an average muscular-walled tube subcutaneous depth.

10. The device of claim 8, wherein:
- the signal comprises light having a spectrum of wavelengths between 400 nm and 1800 nm; or
- the light comprises a discrete wavelength corresponding to a substance found in a blood stream of the body part or a bodily tissue of the body part, wherein:
  - the discrete wavelength ranges from 535 nm to 735 nm and corresponds to a wavelength absorbed by sodium; or
  - the discrete wavelength ranges from 680 nm to 880 nm and corresponds to a wavelength absorbed by potassium.

11. The device of claim 8, wherein:
the band is shaped to fit around at least a portion of a wrist of the user;
a circulatory region of the wrist comprises a volar side of the wrist; and
the fixed distance ranges from 6 mm to 8 mm.

12. The device of claim 8, wherein:
the band is shaped to fit around at least a portion of a wrist of the user;
a circulatory region of the wrist comprises a volar side of the wrist; and
the fixed distance ranges from 1 mm to 4 mm, from 12 mm to 18 mm, or is greater than or equal to 20 mm.

13. The device of claim 1, wherein:
the body part comprises a wrist, a bicep, a thigh, an ankle, a neck, a head, or an earlobe.

14. A device, comprising:
a band, wherein the band is shaped to fit around a body part comprising a muscular-walled tube of a user;
a first physiological sensor coupled to the band and positioned to face a first location on the body part when the user wears the band;
a second physiological sensor coupled to the band and positioned to face a second location on the body part when the user wears the band;
a processor communicatively coupled to the first physiological sensor and the second physiological sensor, the processor operable to:
- take a first biometric measurement by the first physiological sensor;
- take a second biometric measurement by the second physiological sensor;
- compare the first biometric measurement and the second biometric measurement to a baseline biometric measurement; and
- determine, based on the comparison:
  - a closest sensor to a defined position relative to the muscular-walled tube, wherein the closest sensor is either the first physiological sensor or the second physiological sensor; or the first physiological sensor and the second physiological sensor are equidistant from the defined position relative to the muscular-walled tube.

15. The device of claim 14, wherein:
the first physiological sensor comprises a first light source and a first optical sensor; and
the second physiological sensor comprises a second light source and a second optical sensor.

16. The device of claim 14, wherein the second physiological sensor is separated from the first physiological sensor by a fixed distance such that when a signal is transmitted by the first physiological sensor, at least a portion of the signal is transmitted through the muscular-walled tube of the body part before being received by the second physiological sensor.

17. The device of claim 14, wherein the first physiological sensor and the second physiological senor are embedded in a volume of material of the band.

18. A device, comprising:
a band, wherein the band is shaped to fit around a body part comprising a muscular-walled tube of a user;
a first physiological sensor coupled to the band and positioned to face a first location on the body part when the user wears the band;
a second physiological sensor coupled to the band and positioned to face a second location on the body part when the user wears the band, the second physiological sensor is separated from the first physiological sensor by a fixed distance, the fixed distance is determined based on a first size of the first physiological sensor, a second size of the second physiological sensor, a power of a signal received by the second physiological sensor and emitted by the first physiological sensor, or an average muscular-walled tube subcutaneous depth;
a processor communicatively coupled to the first physiological sensor and the second physiological sensor, the processor operable to:
take a first biometric measurement by the first physiological sensor;
take a second biometric measurement by the second physiological sensor;
compare the first biometric measurement and the second biometric measurement to a baseline biometric measurement;
and determine, based on the comparison:
a closest sensor to a defined position relative to the muscular-walled tube based on the comparison, wherein the closest sensor is either the first physiological sensor or the second physiological sensor; or
the first physiological sensor and the second physiological sensor are equidistant from the defined position relative to the muscular-walled tube; and
determine a physiological condition based on the biometric measurement of:
the closest sensor when the first physiological sensor and the second physiological sensor are determined to be not equidistant from the defined position relative to the muscular-walled tube; or
the first physiological sensor or the second physiological sensor when the first physiological sensor and the second physiological sensor are determined to be equidistant from the defined position relative to the muscular-walled tube.

19. The device of claim 18,
wherein:
the first physiological sensor comprises a first light source and a first optical sensor; and
the second physiological sensor comprises a second light source and a second optical sensor; or
wherein:
the first physiological sensor comprises a first impedance pad; and
the second physiological sensor comprises a second impedance pad.

20. The device of claim 18, wherein when the physiological condition comprises a current biometric measurement of the user, the processor is further operative to:
obtain a previous biometric measurement;
determine a change between the previous biometric measurement and the current biometric measurement;
determine a time between the previous biometric measurement and the current biometric measurement; and
determine a rate of change of an overall physiological condition based on the time and the change between the previous biometric measurement and the current biometric measurement.

\* \* \* \* \*